(12) United States Patent
Woodbury

(10) Patent No.: US 11,205,139 B2
(45) Date of Patent: Dec. 21, 2021

(54) COMPUTATIONAL ANALYSIS TO PREDICT MOLECULAR RECOGNITION SPACE OF MONOCLONAL ANTIBODIES THROUGH RANDOM-SEQUENCE PEPTIDE ARRAYS

(71) Applicant: Arizona Board of Regents on behalf of Arizona State University, Scottsdale, AZ (US)

(72) Inventor: Neal Woodbury, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/637,369

(22) PCT Filed: Aug. 2, 2019

(86) PCT No.: PCT/US2019/044980
§ 371 (c)(1),
(2) Date: Feb. 7, 2020

(87) PCT Pub. No.: WO2020/033271
PCT Pub. Date: Feb. 13, 2020

(65) Prior Publication Data
US 2021/0248516 A1   Aug. 12, 2021

Related U.S. Application Data

(60) Provisional application No. 62/715,152, filed on Aug. 6, 2018.

(51) Int. Cl.
*G06N 20/10* (2019.01)
*G16B 5/00* (2019.01)
*G06N 3/08* (2006.01)

(52) U.S. Cl.
CPC ............... *G06N 20/10* (2019.01); *G06N 3/08* (2013.01); *G16B 5/00* (2019.02)

(58) Field of Classification Search
CPC ............. G06N 3/08; G06N 20/10; G16B 5/00
See application file for complete search history.

(56) References Cited

U.S. PATENT DOCUMENTS

| 8,821,703 B2 | 9/2014 | Hayes |
| 8,969,255 B2 | 3/2015 | Johnston |

(Continued)

FOREIGN PATENT DOCUMENTS

| WO | 2005108992 A1 | 11/2005 |
| WO | 2006138479 A2 | 12/2006 |

(Continued)

OTHER PUBLICATIONS

Gomes et al. "Atomic Convolutional Networks for Predicting Protein-Ligand Binding Affinity", 2017, p. 17, https://arxiv.org/abs/1703.10603.*

(Continued)

*Primary Examiner* — Li Wu Chang
(74) *Attorney, Agent, or Firm* — Quarles & Brady LLP

(57) ABSTRACT

Methods and systems, including those employing machine learning, utilizing one or more algorithms for relating the structure of a molecule in a library to its function are described. Embodiments described herein relate structure to function by considering the covalent structure of the molecule, the components of that structure that are common to many molecules in the library, and the properties of those components as they relate to the function in question. Applications include, for example, enhancement and amplification of the diagnostic and prognostic signals provided by (Continued)

peptide arrays for use in analyzing the profile of antibodies in the blood produced in response to a disease, condition or treatment.

2 Claims, 43 Drawing Sheets

Specification includes a Sequence Listing.

(56) References Cited

U.S. PATENT DOCUMENTS

| | | | |
|---|---|---|---|
| 9,709,558 | B2 | 7/2017 | Johnston |
| 9,970,932 | B2 | 5/2018 | Woodbury |
| 10,006,919 | B2 | 6/2018 | Woodbury |
| 10,046,293 | B2 | 8/2018 | Woodbury |
| 10,422,793 | B2 | 9/2019 | Johnston |
| 10,427,125 | B2 | 10/2019 | Woodbury |
| 10,578,623 | B2 | 3/2020 | Woodbury |
| 2003/0032065 | A1 | 2/2003 | Hilser |
| 2009/0042741 | A1 | 2/2009 | Northen |
| 2010/0056392 | A1 | 3/2010 | Greving |
| 2012/0094271 | A1 | 4/2012 | Fu |
| 2012/0190574 | A1 | 7/2012 | Johnston |
| 2013/0079250 | A1 | 3/2013 | Johnston |
| 2013/0203633 | A1 | 8/2013 | Jones |
| 2014/0087963 | A1 | 3/2014 | Johnston |
| 2015/0141296 | A1 | 5/2015 | Woodbury |
| 2015/0241420 | A1 | 8/2015 | Johnston |
| 2017/0106344 | A1 | 4/2017 | Woodbury |
| 2017/0343541 | A1 | 11/2017 | Johnston |
| 2018/0259510 | A1 | 9/2018 | Woodbury |
| 2018/0275136 | A1 | 9/2018 | Woodbury |
| 2019/0034580 | A1 | 1/2019 | Woodbury |
| 2019/0050524 | A1 | 2/2019 | Woodbury |
| 2019/0064177 | A1 | 2/2019 | Woodbury |
| 2019/0271692 | A1 | 9/2019 | Johnston |
| 2020/0016567 | A1 | 1/2020 | Woodbury |

FOREIGN PATENT DOCUMENTS

| | | | |
|---|---|---|---|
| WO | 2007109067 | A2 | 9/2007 |
| WO | 2008091378 | A2 | 7/2008 |
| WO | 2009009028 | A1 | 1/2009 |
| WO | 2009067657 | A2 | 5/2009 |
| WO | 2010027642 | A2 | 3/2010 |
| WO | 2010028214 | A2 | 3/2010 |
| WO | 2010148365 | A2 | 12/2010 |
| WO | 2012154594 | A1 | 11/2012 |
| WO | 2014036312 | A2 | 3/2014 |
| WO | 2014039718 | A1 | 3/2014 |
| WO | 2014062981 | A1 | 4/2014 |
| WO | 2014144383 | A1 | 9/2014 |
| WO | 2014145123 | A2 | 9/2014 |
| WO | 2018170003 | A1 | 9/2018 |
| WO | 2020033271 | A1 | 2/2020 |
| WO | 2020033271 | A9 | 2/2020 |

OTHER PUBLICATIONS

International Searching Authority, International Search Report and Written Opinion for application PCT/US2019/044980, dated Oct. 24, 2019.
Wang, W. et al. "Unstructured interactions between peptides and proteins: Exploring the role of sequence motifs in affinity and specificity." Acta biomaterialia 11 (2015): 88-95.
Nair, V.; et al. Rectified Linear Units Improve Restricted Boltzmann Machines. In 27th International Conference on Machine Learning, 2010; pp. 807-814.
Pasparakis, M., et al. (1996). Immune and inflammatory responses in TNF alpha-deficient mice: a critical requirement for TNF alpha in the formation of primary B cell follicles, follicular dendritic cell networks and germinal centers, and in the maturation of the humoral immune response. Journal of Experimental Medicine, 184(4), 1397-1411.
Pymol Molecular Graphics System, Version 2.1.0 Schrödinger, LLC.
Rost, B., et al. (1994). Combining evolutionary information and neural networks to predict protein secondary structure. Proteins: Structure, Function, and Bioinformatics, 19(1), 55-72.
Rothman, A. L. "Immunity to dengue virus: a tale of original antigenic sin and tropical cytokine storms." Nature Reviews Immunology 11.8 (2011): 532-543.
Saha, S., et al. (2006). Prediction of continuous B-cell epitopes in an antigen using recurrent neural network. Proteins: Structure, Function, and Bioinformatics, 65(1), 40-48.
Screaton, G., et al. "New insights into the immunopathology and control of dengue virus infection." Nature Reviews Immunology 15.12 (2015): 745-759.
Shoemaker, B.A., et al. (2007). Deciphering protein-protein interactions part II: computational methods to predict protein and domain interaction partners. Computational Biology, 3(4), 595-601.
Singh, S., et al., Humoral Immunity Profiling of Subjects with Myalgic Encephalomyelitis Using a Random Peptide Microarray Differentiates Cases from Controls with High Specificity and Sensitivity. Mol Neurobiol, 2016.
Smyth, M.S., et al. (2000). X ray crystallography. Molecular Pathology, 53(1), Aug. 2014.
Sollner, J., et al. (2008). Analysis and prediction of protective continuous B-cell epitopes on pathogen proteins. Immunome Research, 4(1), 1.
Srivastava, N.; et al. Dropout: A Simple Way to Prevent Neural Networks from Overfitting. J. Mach. Learn. Res. 2014, 15, 1929-1958.
Stafford, P., et al, General Assessment of Humoral Activity in Healthy Humans. Molecular & Cellular Proteomics, 2016. 15(5): p. 1610-1621.
Stafford, P., et al. (2012). Physical characterization of the "immunosignaturing effect". Molecular & Cellular Proteomics, 11(4), M111-011593.
Stafford, P., et al. (2014). Immunosignature system for diagnosis of cancer. Proceedings of the National Academy of Sciences, 111(30), E3072-E3080.
Tallorin, L.; et al., Discovering de novo peptide subsliates for enzymes using machine learning. Nat Commun 2018, 9(1), 5253.
Uhlen, M., et al. (2010). Towards a knowledgebased human protein atlas. Nature biotechnology, 28(12), 1248-1250.
Van Regenmortel, M. H. (2009). What is a B-cell epitope? In Epitope Mapping Protocols (pp. 3-20). Humana Press.
Veltri, D.; et al., Deep learning improves antimicrobial peptide recognition. Bioinformatics 2018, 34 (16), 2740-2747.
Wals, K., et al. (2014). Unnatural amino acid incorporation in $E.$ $coli$: current and future applications in the design of therapeutic proteins. Frontiers in Chemistry, Feb. 2015.
Wang, A., et al. (2012). Protein engineering with non natural amino acids. Protein Engineering, 253-290.
Williams, B.A.R., et al., Creating Protein Affinity Reagents by Combining Peptide Ligands on Synthetic DNA Scaffolds. Journal of the American Chemical Society, 2009. 131(47): p. 17233-17241.
World Health Organization, Dengue & Severe Dengue, accessed online at http://www.who.int/mediacentre/factsheets/fs117/en/ Last updated Apr. 15, 2019.
Xie, Z.R., et al. (2015). Methods for predicting protein-ligand binding sites. Methods in Molecular Biology, 1215, 383-398.
Voshida, M.; et al., Using Evolutionary Algorithms and Machine Learning to Explore Sequence Space for the Discovery of Antimicrobial Peptides. Chem 2018, 4 (3), 533-543.
Zak, K.M., et al. (2015). Structure of the complex of human programmed death 1, PD-1 and its ligand PD-L1. Structure, 23(12), 2341-2348.
U.S. Appl. No. 16/029,965, filed Jul. 9, 2018, Woodbury.
U.S. Appl. No. 16/562,383, filed Sep. 5, 2019, Johnston et al.
U.S. Appl. No. 16/748,723, filed Jan. 21, 2020, Woodbury et al.
Alquraishi, M., End-to-End Differentiable Learning of Protein Structure. Cell Syst 2019, 8 (4), 292-301 e3.

(56) References Cited

OTHER PUBLICATIONS

Assuma, R., et al. (1998). IL-1 and TNF antagonists inhibit the inflammatory response and bone loss in experimental periodontitis. The Journal of Immunology, 160(1), 403-409.
Barlow, D. J., et al. (1986). Continuous and discontinuous protein antigenic determinants. Nature, 322(6081), 747.
Berman, H.M., et al. (2000). The protein data bank. Nucleic Acids Research, 28, 235-242.
Bhatt, S., et al. "The global distribution and burden of dengue." Nature 496.7446 (2013): 504-507.
Bradford, J.R., et al. (2005). Improved prediction of protein-protein binding sites using a support vector machines approach. Bioinformatics, 21(8), 1487-1494.
Centers for Disease Control and Prevention, Dengue, accessed online at ,https://www.cdc.gov/dengue/index.html., last updated on Jan. 15, 2019.
Diehnelt, C.W., et al., Discovery of High-Affinity Protein Binding Ligands—Backwards. Plos One, 2010. 5(5).
Diehnelt, C.W., Peptide array based discovery of synthetic antimicrobial peptides. Front Microbiol, 2013. 4: p. 402.
Dimaio, F. et al, Modeling symmetric macromolecular structures in Rosetta3. Plos One 2011, 6 (6), e20450.
Domenyuk, V., et al., A Technology for Developing Synbodies with Antibacterial Activity. Plos One, 2013. 8(1).
Elong Ngono, A. et al. "Immune response to dengue and Zika." Annual review of immunology 36 (2018): 279-308.
Evans, R. et al., De novo structure prediction with deep-learning based scoring. In Thirteenth Critical Assessment of Techniques for Protein Structure Prediction (Abstracts) Dec. 1-4, 2018. Retrieved from https://deepmind.com/blog/article/alphafold-casp13.
Feuerstein, G.Z., et al. (1994). Cytokines, inflammation, and brain injury: a role of tumor necrosis factor-alpha. Cerebrovascular and Brain Metabolism Reviews, 6(4), 341-360.
Forsström, B., et al. 2014. Proteome-wide epitope mapping of antibodies using ultra-dense peptide arrays. Molecular & Cellular Proteomics, 13(6), pp. 1585-1597.
Fout, A. et al., Protein Interface Prediction using Graph Convolutional Networks. 2017, 6530-6539.
Francisco, L.M., et al. (2010). The PD-1 pathway in tolerance and autoimmunity. Immunological Reviews, 236, 219-242.
Gallet, X., et al. (2000). A fast method to predict protein interaction sites from sequences. Journal of Molecular Biology, 302(4), 917-926.
Gao, M.; et al., DESTINI: A deep-learning approach to contact-driven protein structure prediction. Sci Rep 2019, 9 (1), 3514.
Greenbaum, J.A., et al., 2007. Towards a consensus on datasets and evaluation metrics for developing B-cell epitope prediction tools. Journal of Molecular Recognition, 20(2), pp. 75-82.
Greving, M.P., et al., High-throughput screening in two dimensions: Binding intensity and off-rate on a peptide microarray. Analytical Biochemistry, 2010. 402(1): p. 93-95.
Greving, M.P., et al., Thermodynamic Additivity of Sequence Variations: An Algorithm for Creating High Affinity Peptides Without Large Libraries or Structural Information. Plos One, 2010. 5(11).
Gupta, N., et al., BIOL 183-Synbodies: Progress toward development of synthetic affinity agents. Abstracts of Papers of the American Chemical Society, 2008. 236.
Gupta, N., et al., Engineering a Synthetic Ligand for Tumor Necrosis Factor-Alpha. Bioconjugate Chemistry, 2011. 22(8): p. 1473-1478.
Gupta, N., et al., Synthetic ligands (synbodies): Synthetic alternatives to antibodies. Abstracts of Papers of the American Chemical Society, 2010. 240.
Halperin, R. F., et al. (2011). Exploring antibody recognition of sequence space through random-sequence peptide microarrays. Molecular & Cellular Proteomics, 10(3), M110-000786.
Haney, E. F.; et al., Reassessing the Host Defense Peptide Landscape. Front Chem, Jul. 2019, 43.
Hashemifar, S.; et al., Predicting protein-protein interactions through sequence-based deep learning. Bioinformatics 2018, 34 (17), i802-i810.
Herbst, R.S., et al. (2014). Predictive correlates of response to the anti-PD-L1 antibody MPDL3280A in cancer patients. Nature, 515,563-567.
Hino, N., et al. (2006). Site-specific incorporation of non-natural amino acids into proteins in mammalian cells with an expanded genetic code. Nature Protocols, 1(6), 2957-2962.
Hopp, T. P., et al. (1981). Prediction of protein antigenic determinants from amino acid sequences. Proceedings of the National Academy of Sciences, 78(6), 3824-3828.
Iwai, Y., et al. (2002). Involvement of PD-L1 on tumor cells in the escape from host immune system and tumor immunotherapy by PDL1 blockade. Proceedings of the National Academy of Sciences of the United States of America, 99(19), 12293-12297.
Jenson, J. M.; et al., Peptide design by optimization on a data-parameterized protein interaction landscape. Proc Natl Acad Sci U S A 2018, 115 (44), E10342-E10351.
Jeong, J.S., et al. (2012). Rapid identification of monospecific monoclonal antibodies using a human proteome microarray. Molecular & Cellular Proteomics, 11(6), O111-016253.
Jespersen, M. C.; et al., Antibody Specific B-Cell Epitope Predictions: Leveraging Information From Antibody-Antigen Protein Complexes. Front Immunol, Oct. 2019, 298.
Johansson-Åkhe, I.; et al., Predicting protein-peptide interaction sites using distant protein complexes as structural templates. bioRxiv 2018, 398768.
Källberg, M., et al. (2012). Template based protein structure modeling using the RaptorX web server. Nature Protocols, 7, 1511-1522.
Kingma, D. P.; et al. Adam: A Method for Stochastic Optimization. In 3rd International Conference on Learning Representations, 2015.
Krystek, S.R. Jr., et al. (1995). Hydrophobicity profiles for protein sequence analysis. Current Protocols in Protein Science, 2.2.1-2.2.13.
Lainson, J.C., et al., Conjugation Approach To Produce a *Staphylococcus aureus* Synbody with Activity in Serum. Bioconjugate Chemistry, 2015. 26(10): p. 2125-2132.
Larsen, J. E. P., et al. (2006). Improved method for predicting linear Bcell epitopes. Immunome research, 2(1), 2.
Lee, E. Y.; et al, Machine learning-enabled discovery and design of membrane-active peptides. Bioorganic & Medicinal Chemistry 2018, 26 (10), 2708-2718.
Legrain, P., et al. (2011). The human proteome project: current state and future direction. Molecular & cellular proteomics, 10(7), M111-009993.
Legutki, J. B., et al. (2014). Scalable high-density peptide arrays for comprehensive health monitoring. Nature communications, 5, 4785.
Legutki, J.B. et al, Immunosignatures can predict vaccine efficacy. Proceedings of the National Academy of Sciences of the United States of America, 2013. 110(46): p. 18614-18619.
Locksley, R.M., et al. (2001). The TNF and TNF receptor superfamilies. Integrating Mammalian Biology, 104(4), 487-501.
MATLAB R2017a—academic use [Computer software]. The MathWorks, Inc. (2017).
Meiler, J.; et al., Generation and evaluation of dimension-reduced amino acid parameter representations by artificial neural networks. 2001; vol. 7, p. 360-369.
Mukai, Y., et al. (2010). Solution of the structure of the TNF-TNFR2 complex. Science Signaling, 3(148).
Mukherjee, S., et al. (2011). Protein-protein complex structure predictions by multimeric threading and template recombination. Structure, 19(7), 955-966.

\* cited by examiner

QAFDSH (SEQ ID NO. 3); ALEKDY (SEQ ID NO. 5); RHSVV (SEQ ID NO.6)

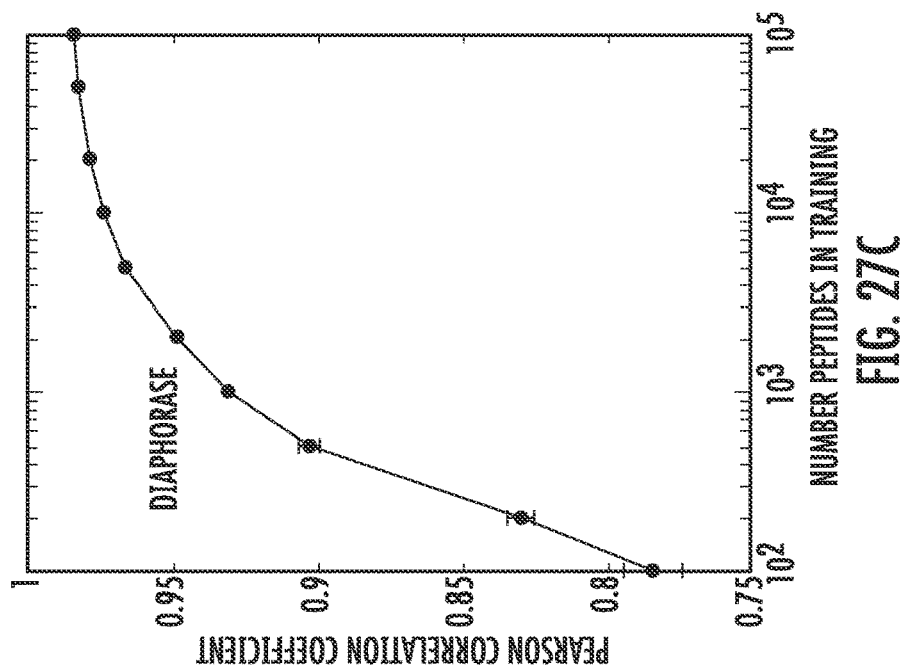
FIG. 27C
| PROTEIN | CORR. COEF. |
|---|---|
| DIAPHORASE | 0.985 ± 0.001 |
| FERREDOXIN | 0.983 ± 0.001 |
| FNR | 0.994 ± 0.001 |
| PD1 | 0.959 ± 0.002 |
| PDL1 | 0.965 ± 0.003 |
| TNFα | 0.960 ± 0.002 |
| TNFα RECEPTOR | 0.973 ± 0.001 |
| TRANSFERRIN | 0.979 ± 0.001 |
| Fc | 0.924 ± 0.007 |
FIG. 27B
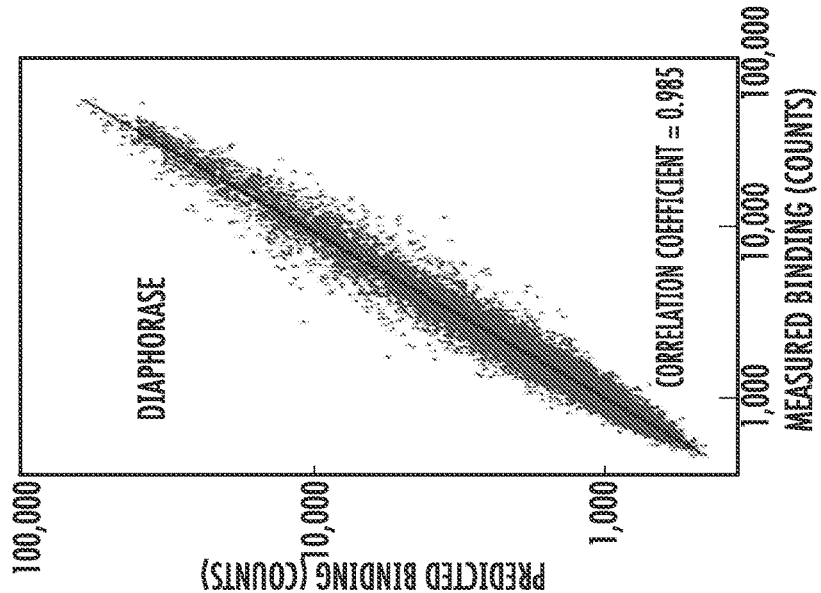
FIG. 27A

AMINO ACID

| | A | D | E | F | G | H | K | L | N | P | Q | R | S | V | W | Y |
|---|---|---|---|---|---|---|---|---|---|---|---|---|---|---|---|---|
| 1 | 0 | 0 | 1 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 1 | 0 | 0 | 0 | 0 | 0 |
| 3 | 0 | 0 | 0 | 0 | 0 | 0 | 0 | 1 | 0 | 0 | 0 | 0 | 0 | 0 | 0 | 0 |
| 4 | 0 | 0 | 0 | 0 | 0 | 0 | 0 | 0 | 0 | 0 | 0 | 1 | 0 | 0 | 0 | 0 |
| 5 | 0 | 0 | 0 | 0 | 0 | 0 | 0 | 0 | 0 | 0 | 1 | 0 | 0 | 0 | 0 | 0 |
| 6 | 0 | 0 | 0 | 0 | 0 | 0 | 0 | 0 | 0 | 0 | 0 | 0 | 0 | 1 | 0 | 0 |
| 7 | 0 | 1 | 0 | 0 | 0 | 0 | 0 | 0 | 0 | 0 | 0 | 0 | 0 | 0 | 0 | 0 |
| 8 | 0 | 0 | 0 | 0 | 1 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 | 0 | 0 | 0 |

SEQUENCE POSITION

FIG. 32

CHEMICAL SPACE

| | | | | | |
|---|---|---|---|---|---|
| 1 | -0.530 | 2.268 | 0.715 | 0.852 | -0.268 |
| 2 | -0.551 | -1.228 | -0.432 | 2.422 | -0.003 |
| 3 | -0.160 | 0.859 | 0.214 | -0.944 | 0.309 |
| 4 | -0.232 | -0.505 | -1.274 | 1.842 | -0.110 |
| 5 | -0.551 | -1.228 | -0.432 | 2.422 | -0.003 |
| 6 | 1.423 | -0.716 | -0.430 | -0.004 | 0.924 |
| 7 | -1.353 | -0.801 | -0.864 | -0.028 | -0.247 |
| 8 | -2.251 | -0.413 | -0.504 | -0.237 | 1.036 |
| 9 | 0.000 | 0.000 | 0.000 | 0.000 | 0.000 |
| 10 | 0.000 | 0.000 | 0.000 | 0.000 | 0.000 |
| 11 | 0.000 | 0.000 | 0.000 | 0.000 | 0.000 |
| 12 | 0.000 | 0.000 | 0.000 | 0.000 | 0.000 |
| 13 | 0.000 | 0.000 | 0.000 | 0.000 | 0.000 |

SEQUENCE POSITION

COMPUTATIONAL ANALYSIS TO PREDICT MOLECULAR RECOGNITION SPACE OF MONOCLONAL ANTIBODIES THROUGH RANDOM-SEQUENCE PEPTIDE ARRAYS

CROSS-REFERENCE TO RELATED APPLICATIONS

This application represents the national stage entry of PCT International Application No. PCT/US2019/044980, filed on Aug. 2, 2019, and claims priority to U.S. Application No. 62/715,152, filed on Aug. 6, 2018, each of which is incorporated by reference herein as if set forth in its entirety.

STATEMENT REGARDING FEDERALLY SPONSORED RESEARCH

This invention was made with government support under 1243082 awarded by the National Science Foundation. The government has certain rights in the invention.

BACKGROUND OF THE DISCLOSURE

While many methods are known to those skilled in the art to prepare libraries of molecules and measure their functional properties, such approaches to relating the covalent structure of molecules in libraries to their function rely on the concept that the molecules can be described as a series of component pieces and those component pieces act more or less independently to give rise to function. A common example in the application of nucleic acid and peptide libraries is the derivation of a consensus motif, a description of a sequence of nucleotides or amino acids that assigns a position dependent functional significance to each.

However, many of the interactions in biology cannot be described by such simple models, and methods of considering higher order interactions between multiple components of a library molecule, both adjacent in the structure and distributed within the structure, with the ligand or functional activity in question are required.

SUMMARY OF DISCLOSURE

Embodiments herein involve methods for relating the structure of a molecule in a library to its function by analyzing experimental data from a library comprising one or more chemical structures.

For example, the method includes obtaining a data set associated with one or more chemical structures based on a signal derived from interaction of the one or more chemical structures with a physical phenomenon of interest and applying a model description to the data set that enables determination of a function of the molecule in the library according to values representing its covalent structure, one or more components of that structure, and one or more properties of the components as they relate to the function in question.

In certain embodiments, methods and systems utilizing one or more algorithms for relating functional data from a library of defined molecules to a respective structure of those defined molecules are disclosed. In some embodiments, the methods include obtaining a data set associated with one or more chemical structures based on a signal derived from interaction of the one or more chemical structures with a chemical or physical phenomenon of interest, and applying a model description utilizing the one or more algorithms to the data set to thereby enable determination of a function of a defined molecule in the library according to a value representing the defined molecule's covalent structure, one or more components of that structure, and one or more properties of the components as each relates to the function in question.

Thus, in some embodiments, the methods may be utilized for relating functional data from a library of defined molecules to a respective structure of those defined molecules, such as an antigen.

In certain system embodiments, the systems may be programmed with one or more algorithms for relating functional data from a library of defined molecules to a respective structure of those defined molecules. In exemplary embodiments, the system comprises a specially programmed digital processing device that includes one or more non-transitory computer readable storage media encoded with one or more programs that apply a model description utilizing the one or more algorithms to a data set to thereby enable determination of a function of a defined molecule in the library according to a value representing the defined molecule's covalent structure, one or more components of that structure, and one or more properties of the components as each relates to the function in question.

In further embodiments, the systems are programed for relating functional data from a library of defined molecules to a respective structure of those defined molecules. In one application, those systems may be used, for example, peptide-protein binding prediction utilizing machine learning.

These and other aspects of the disclosure are described in further detail below. However, such description is not intended to limit the disclosure to particular examples or embodiments.

BRIEF DESCRIPTION OF THE DRAWINGS

FIG. 27. A) Diaphorase was incubated with arrays of ~126,000 unique and nearly random peptide sequences, and a relative binding value was recorded for each sequence. A neural network was trained on a random 90% of the sequence/binding value pairs and used to predict the target binding for the remaining 10% (test set). The predictions for the test set are shown plotted against their measured values. Details are given in the supplementary material. B) This modeling procedure was performed 100 times for 9 different proteins, with the average correlation coefficients between the predicted and measured values tabulated (the error of the mean is shown). C) The number of peptide sequences used to train the model was varied from 100 to 100,000, and the correlation coefficients between the measured and predicted values of the test set were recorded for each training set size. As above, training sets were randomly selected 100 times and error of the mean is shown.

FIG. 32. The input to the neural network is the peptide sequence represented as a binary matrix. The size of the matrix is 13×16 (maximum length of peptides on the array× number of different amino acids) for all peptides. Each row is a vector of zeros and a one to indicate the amino acid at that position in the sequence. Unused rows for shorter peptides are filled with zeros. This matrix representation of the peptide is sparse, meaning that the information content is spread out thinly amongst only a small number of non-zero elements in the matrix. Sparse binary matrix representation of peptides (EQNSQVDG, SEQ ID NO. 1, shown as an example). The rows are the sequence positions, and in each row a 1 (shown in bold) indicates which out of the 16 amino acids occupies that position. After the peptide sequence has terminated, the remaining rows (9-13 in the example above) are filled with zeros. The first layer of the neural network is an encoder that maps the sparse 13×16 peptide matrix (FIG. 32) to a dense 13×N representation where N<16 (FIG. 33). This linear transformation is performed by multiplying the sparse representation with a 16×N matrix whose weights are optimized during the training. The goal of the encoder is to preserve as much information about the sequences relevant to peptide binding as possible throughout the dimensionality reduction process. The neural network must therefore learn how to represent the amino acids in a continuous, real-valued space to avoid loss of information content as the amino acids are mapped to a lower dimension. Presumably, the real-value vector representations of each amino acid determined by the neural network contain some representation of the chemical features of the amino acids (e.g. charge, van der Waals radius, hydrophobicity . . . ), a concept explored below. Note, however, that the neural network is not confined by known chemical properties and any particular fit will generate a unique representation of the amino acids; the optimization is for a complete space, but the relative orientations of the vectors used as the basis for that space is not confined and thus varies from fit to fit. For greater dimensionality reduction (as one reduces the number of descriptors available to the network), the encoder is pressured further to learn an efficient set of real-valued vector representations of each amino acid optimized for peptide binding.

FIG. 33. Dense matrix representation of peptides (EQNSQVDG, SEQ ID NO. 1, shown as an example). This matrix was generated by passing the sparse representation (FIG. 32) through the encoder portion of the neural network designed to reduce the dimensionality of the amino acid space to a real-valued space of N=5 descriptors. In general, the number of descriptors in the real-valued vector space encoded by the neural network can be any positive integer less than the number of amino acids (16 in this work). After encoding each amino acid of the peptide sequence into a compact real-valued vector, all of the rows of the matrix are concatenated into a single vector. This vector is the real-valued space representation of the entire peptide sequence. The peptide real-valued space vector is then passed through a feedforward neural network with two hidden layers with 100 filters each to predict binding value. The rectified linear unit activation function is applied to the output of each hidden layer to introduce non-linearity into the model. A final output layer transforms the hidden layer representations into the predicted binding value, and no activation function is applied to this output. A full diagram of the neural network architecture is shown in FIG. 34.

$$G(k) = \frac{1}{c_0 M} \sum_{m=1}^{M-k} (y_m - \bar{y})(y_{m+k} - \bar{y})$$

of a trace that follows the predicted binding value during a random walk in which each step is a point mutation. Here, G is the autocorrelation as a function of the correlation lag in mutation steps during the random walk, k. A is the total number of steps, $y_m$ is the predicted binding for the sequence generated by the $m^{th}$ mutation in the series. $c_0$ is the sample variance. Starting with a randomly generated 10-amino acid peptide sequence, 10,000 randomly selected mutations are performed sequentially and for each mutation the binding is predicted from a fit of the binding data for a particular protein. The predicted binding values for this series of point mutations in the sequential random walk is essentially a one-dimensional representation of the topology of the molecular recognition landscape for a particular protein, and is used to generate an autocorrelation curve. The experiment was repeated 500,000 times for each protein (50,000 times for each of 10 independent fits) and the average result is shown. The error of the mean is smaller than the width of the line. The number of mutations in the random walk required to decrease G to 0.5 is shown in the inset for each protein.

Figure 42:
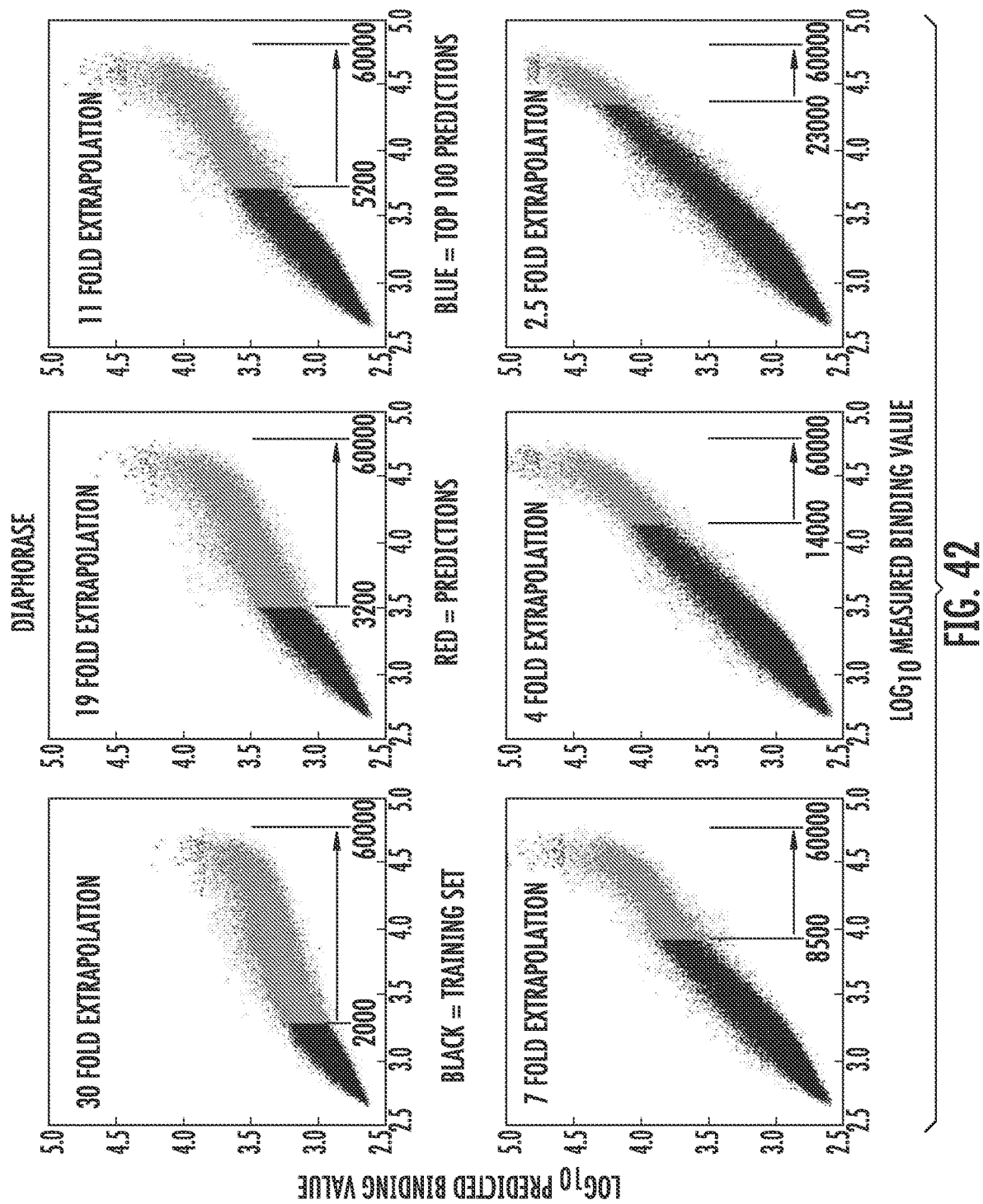

FIG. 42. Extrapolations to peptide sequences that bind diaphorase more strongly than any of those observed in the training set. The extrapolative performance is shown for neural networks trained on different ranges of weak binding peptides. The training set is in black, the test set in red, and the top 100 predicted binders in blue. The x and y axes are $\log_{10}$ of the number of counts in each binding measurement and the values shown in each panel are the actual number of counts over which predictions are made. The larger the dynamic range of the training set, the more accurately the test points are predicted, but even when training occurs on only the bottom 3% of the measured values, the top 100 predicted values average 20-fold higher than the highest value used in the training.

Figure 43:
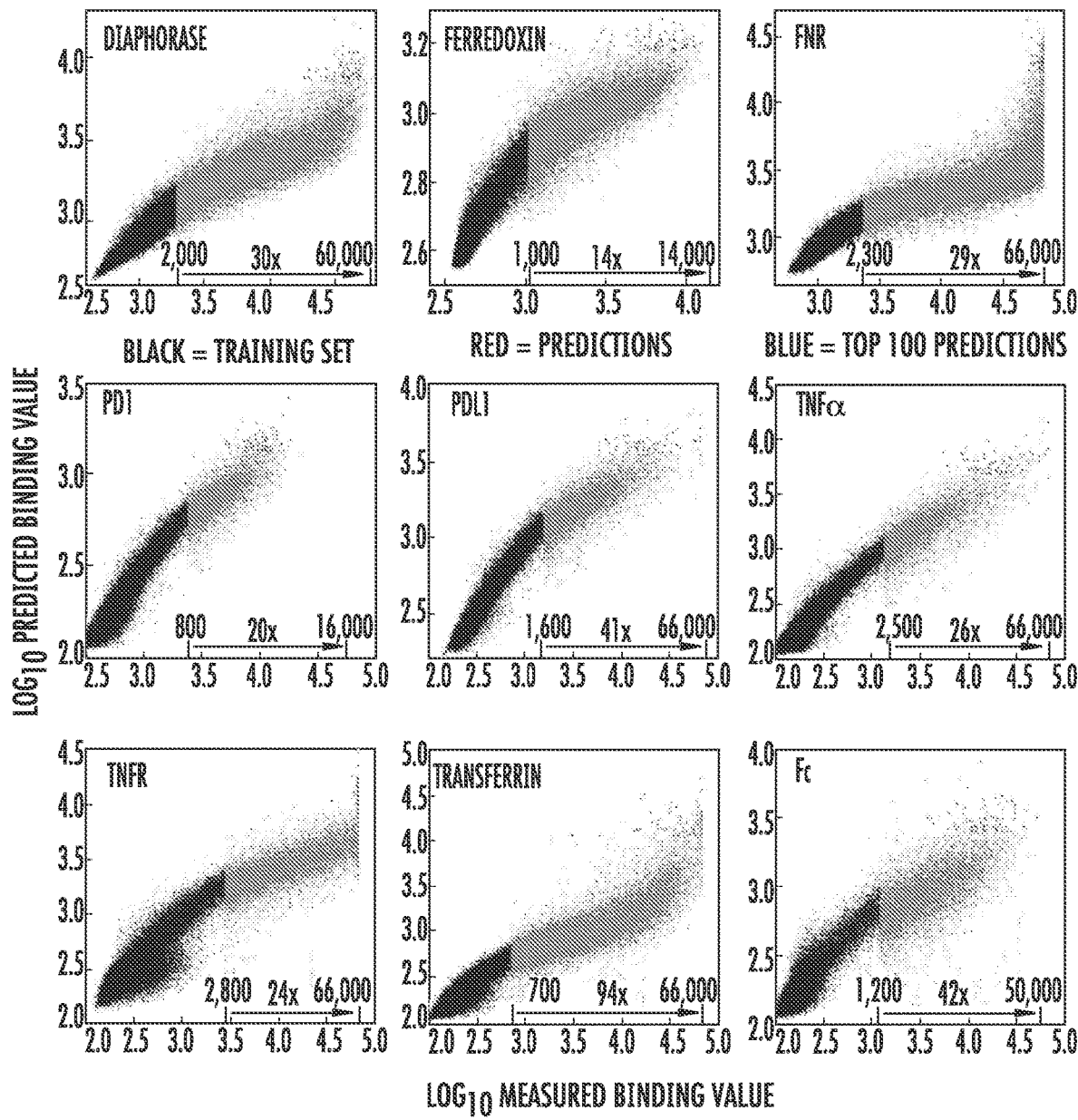

FIG. 43. Extrapolations to peptide sequences that bind more strongly than any of those observed in the training set for models trained on all of the different protein targets. The training set is in black, the test set in red, and the top 100 predicted binders in blue. Note that the top predictions in every case are among the highest measured values and represent extrapolation over ranges between 14- and 94-fold. Note that in cases where the measurement saturates substantially (FNR, TNFR and transferrin), the highest values predicted are generally those in saturation. Note also that in a number of cases the points (sequences) that fit the worst form vertical lines. These are the cases where one of the averaged runs was saturated and the other one or two runs were much lower. This probably represents artifacts on the arrays that gave bright spots in one run for a few points (e.g., dust; we did not exclude any data in our analysis).

Figure 44:
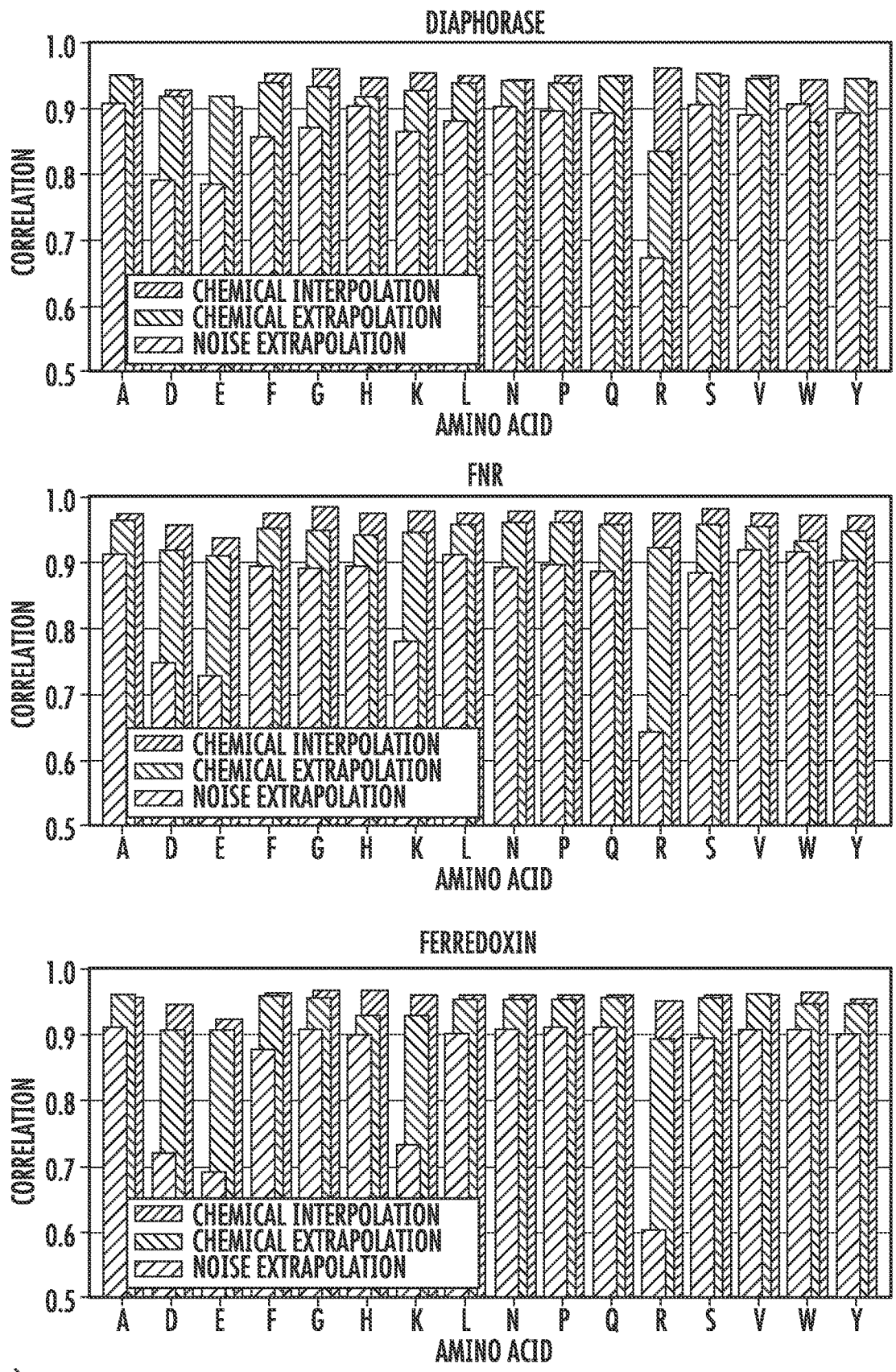

FIG. 44. Chemical extrapolation to represent amino acids left out of the training set. The encoder matrix was replaced with the isoelectric point, hydrophobicity, and van der Waals terms for the amino acids, and these values were fixed, forcing the neural network to learn the relationship between these physical-chemical properties and the corresponding binding value and effectively reducing a sequence of amino acids to a sequence of physical-chemical values. This should allow the neural network to learn chemistry and predict how other combinations of physical chemical values would behave in the array. To test this, the model was trained on all peptides without the amino acid indicated in the bar graph, replacing the sequence of amino acids with the sequence of three physical-chemical property values of amino acids present, and then tested on the remaining set of peptides that contain the amino acid in question. This forces the network to use the chemistry it learned from the other amino acids to predict what a new amino acid with a different set of physical-chemical values would do (orange). The correlation between predicted and measured values is plotted. As a negative control, the physical-chemical properties for the extrapolated amino acid were replaced with random numbers (green, repeated with 100 sets of random numbers). As a positive control, the neural network was trained and evaluated on the set of amino acids containing the amino acid (blue, 90% train and 10% test).

Figure 45:
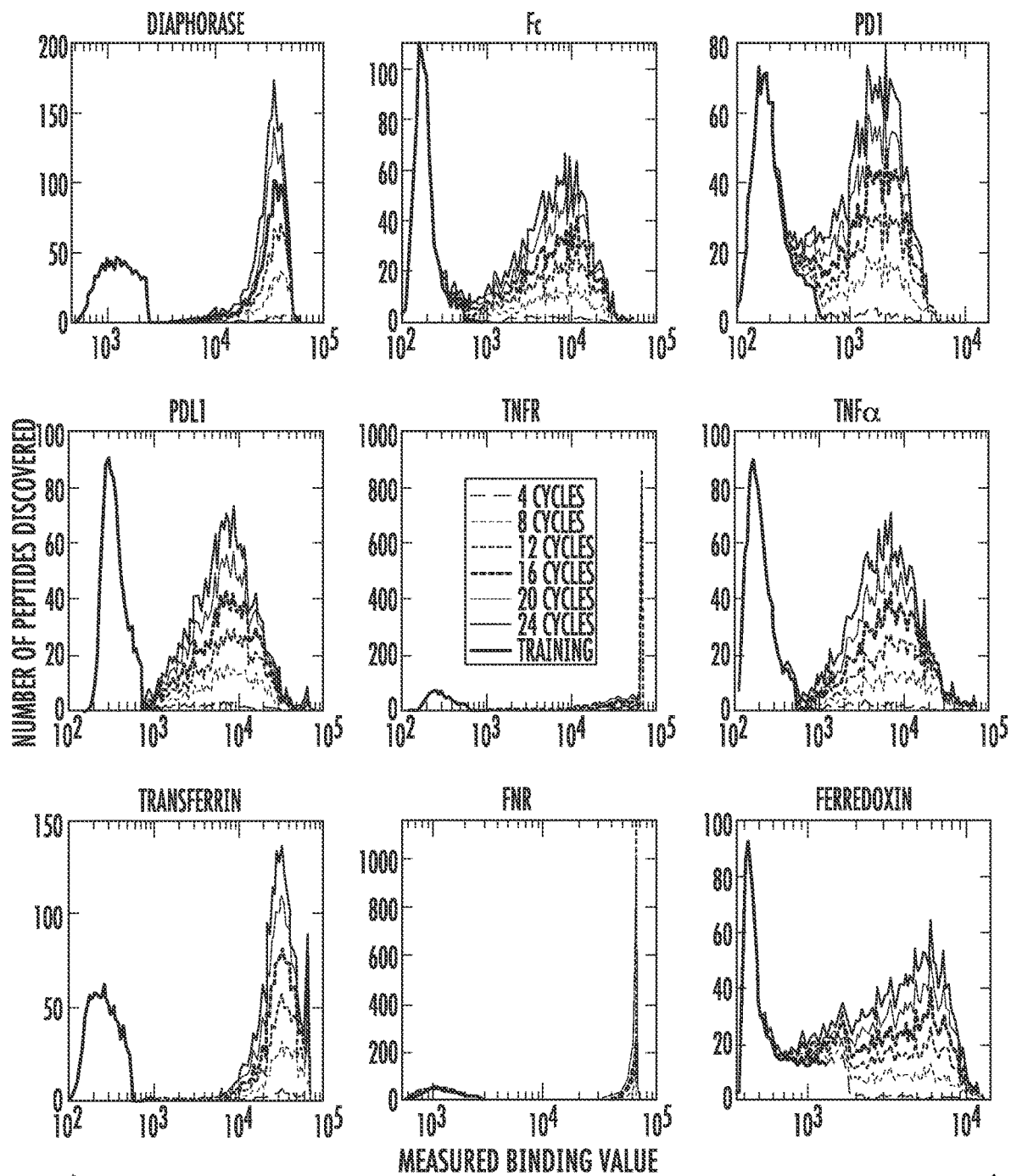

FIG. 45. Iterative training a neural network to discover strong binding peptides. The model is initially trained on a weak binding subset of the data (dark blue curve), and then asked to predict the top 100 binders on the peptide array. These predicted peptides are added to the training set, and another 100 peptides is predicted, etc. The multicolored curves represent the distribution of binding for the "discovered" sequences as a function of cycle number. This process is iterated for 50 cycles. Each experiment was repeated 10 times and averaged. In general, the curves are distinctly bimodal, with the high values increasing rapidly during the iterative optimization. For two of the proteins, TNFR and FNR, there were more than 100 sequences with saturating binding and thus essentially all of the predicted values are at or very near saturation.

Figure 46:
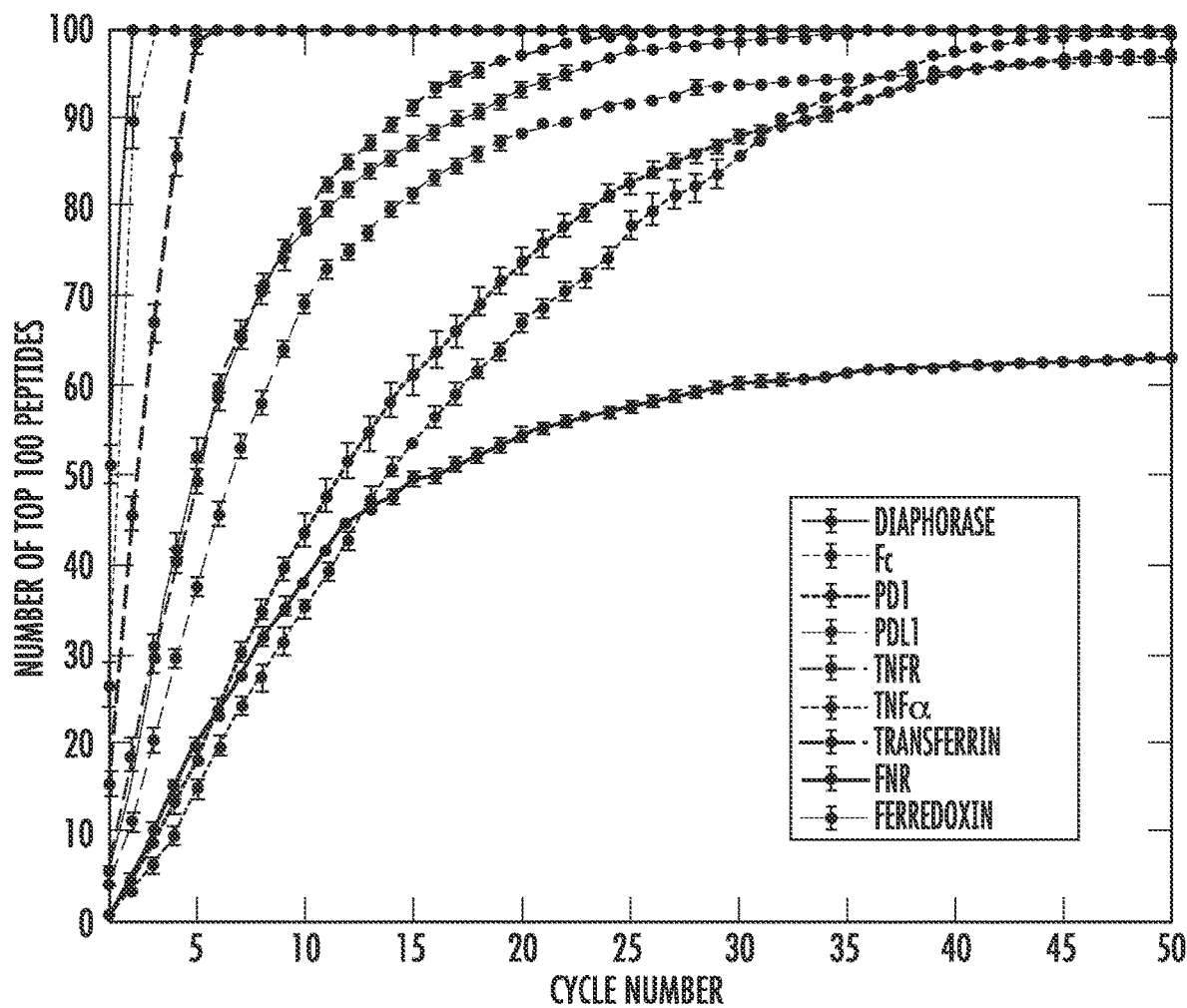

FIG. 46. Number of the top 100 peptides on the array discovered by the neural network as a function of learning cycle number for each of the proteins during the iterative optimization described in FIG. 45. Each experiment was repeated 10 times and averaged and the error of the mean is shown when it is larger than the symbol. With the exception of Fc, all or almost all of the top 100 peptides are discovered within 50 cycles. In the case of Fc, looking at FIG. 43, one can see the issue. There are a series of points near saturation that are always predicted to be low. These points are likely artifacts (e.g., dust), as they have saturated binding in only one of the two replicates and low binding in the other (there are 34 such points in the dataset and a few others that are near saturating in one and low in the other). Thus, there is no way the network can predict them accurately because their average value is not consistent with the sequence dependence. Similarly, there are several such points in both PD1 (3 very high in one that are low in the other) and PDL1 (2 saturating in one and low in the other) which keep them from quite finding all 100 of the highest measured values. The rate at which TNFR, FNR and Transferrin increase with cycle is somewhat artificial. There are more than 100 measured binding values in saturation, so as long as one of the saturated values is found, it is counted as being in the top 100. As is apparent in FIG. 43, the prediction rapidly finds the values that are deep in saturation.

DETAILED DESCRIPTION

The preferred embodiments are described with reference to the Figures, in which like numbers represent the same or similar elements. The described features, structures, or characteristics of the contents herein may be combined in any suitable manner in one or more embodiments. In the following description, numerous specific details are recited to provide a thorough understanding of embodiments disclosed herein. One skilled in the relevant art will recognize, however, that embodiments disclosed herein may be practiced without one or more of the specific details, or with other methods, components, materials, and so forth. In other instances, well-known structures, materials, or operations are not shown or described in detail to avoid obscuring inventive aspects. All publications recited herein are hereby incorporated by reference in their entirety.

Embodiments disclosed herein utilize one or more algorithms in methods for relating functional data from libraries of defined molecules to the structures of those molecules. The algorithms involve a three part description of the molecules in the library in terms of 1) covalent structure of each molecule, 2) a set of structural components that make up the molecules, and 3) a description of the properties of the structural components that relate them to the function in question. Using this formalism, it has been demonstrated that one can accurately predict the function of molecular species that are NOT present in the library that was fit to the algorithm, if those molecules can be described using the same component structures and associated properties as the molecules present in the libraries used to perform the fits.

Thus, embodiments disclosed herein related to the use of these algorithms in such a way that they improve the performance of molecular library technologies in a number of molecular array applications. These applications include but are not limited to.

Design of new molecular libraries with specific function

Screening of complex molecular systems of known structure for functional prediction Discovery of potential lead compounds with desirable functions Use in the development and implementation of diagnostic methods Use in the development of therapeutics and vaccines Specific embodiments are described which relate to an array of peptides (amino acid polymers) and their binding properties relative to both isolated antibodies and the total circulating antibody population in blood as well as to binding to other proteins of biological and biomedical interest. The specific applications of these embodiments include but are not limited to:

Design of peptide arrays that bind to specific antibodies or to antibodies in serum with specific properties such as the presence of antibodies expressed during a disease state The enhancement and amplification of the diagnostic and prognostic signals provided by peptide arrays for use in analyzing the profile of antibodies in the blood produced in response to a disease, condition or treatment.

Discovery of protein antigens or polypeptide sequences that are responsible for the response to a disease, condition or treatment (e.g., discovery of antigens for a vaccine).

Discovery of protein antigens or polypeptide sequences that are responsible for adverse reactions resulting from a disease, condition or treatment (e.g., autoimmune reactions).

The discovery of lead compounds to be used in the development of therapeutics.

The discovery of potential targets of therapeutic treatment.

The characterization of specific antibodies, such as monoclonal antibodies used as therapeutics, to determine what peptide and protein sequences they are expected to bind The discovery of protein antigens that could be used in the development of vaccines The discovery of ligands appropriate for developing specific binding complexes to proteins or other molecular complexes.

Molecular Libraries

There are many methods known to those skilled in the art to prepare libraries of molecules and measure their functional properties. These include but are not limited to phage display, RNA display, synthetic bead-based libraries, and other library techniques using synthesized molecules. The approach described here is applicable to any molecular library system in which the function in question can be measured for enough of the unique molecular species in the library to allow the fitting routine to properly converge. Specifically, the approach requires that the number of molecular species for which measurements are performed be greater, and preferably much greater, than the number of free parameters used in defining the algorithm. The number of free parameters in turn depends on the complexity of the structural and chemical model described by the algorithm.

Specific embodiments of this general approach herein are described involving large peptide arrays. The processes and analysis described, however, are not specific to peptide arrays and those skilled in the art will recognize that this is a general approach to molecular library analysis that can be used with any library of molecules for which the structure of some or all of the molecules in the library can be described in terms of a common set of structural features and a measured response of some kind can be associated with that structure. Molecular libraries could include but are not limited to peptides, nucleic acids, proteins, sugars and sugar polymers, any of the former with non-natural components (e.g., non-natural amino acids or nucleic acids), molecular polymers of known covalent structure, branched molecular structures and polymers, circular molecular structures and polymers, molecular systems of known composition created in part through self-assembly (e.g. structures created through hybridization to DNA or structures created via metal ion binding to molecular systems).

Measured responses include but are not limited to binding, chemical reactivity, catalytic activity, hydrophobicity, acidity, conductivity, electromagnetic absorbance, electromagnetic diffraction, fluorescence, magnetic properties, capacitance, dielectric properties, flexibility, toxicity to cells, inhibition of catalysis, inhibition of viral function, index of refraction, thermal conductivity, optical harmonic generation, resistance to corrosion, solubility, stability in blood, rate of clearance from the body and resistance to or ease of hydrolysis.

A specific embodiment described here relates to peptide arrays which have been exposed either to individual antibodies or to blood or serum containing multiple antibodies. In this embodiment, antibodies bind to the array of peptides and are detected either directly (e.g. using fluorescently labeled antibodies) or by the binding of a labeled secondary antibody that binds to all of the antibodies of a specific type (e.g., IgG or IgM). Together, the signals produced from binding of antibodies to the features in the array form a pattern, with the binding to some peptides in the array much greater than to others. It should be noted that the arrays used in this embodiment have been extensively employed not only for antibody binding but for binding to other proteins, small molecules, whole viruses, whole bacteria and eukaryotic cells as well (See References 1-10). The methods described apply to all of these cases. The specific arrays used in this embodiment consisted of between 120,000 and 130,000 unique peptides. However larger and smaller sized libraries can be used as long as they meet the criteria described above. Array synthesis and binding assays in the examples given below were performed as has been described in the literature (See References 11-14). For some of the studies, the arrays were synthesized and or assays performed by the company HealthTell, Inc. For other studies the arrays were synthesized and/or assays performed in the Peptide Array Core at Arizona State University.

Algorithms that Relate the Structure of Molecular Species in a Library to their Measured Function.

Most approaches to relating the covalent structure of molecules in libraries to their function rely on the concept that the molecules can be described as a series of component pieces and those component pieces act more or less independently to give rise to function. A common example in the application of nucleic acid and peptide libraries is the derivation of a consensus motif, a description of a sequence of nucleotides or amino acids that assigns a position dependent functional significance to each.

However, many of the interactions in biology cannot be described by such simple models, and methods of considering higher order interactions between multiple components of a library molecule, both adjacent in the structure and distributed within the structure, with the ligand or functional activity in question are required. These higher order interactions are information rich processes, and thus to identify them requires the analysis of a large number of examples of interactions between the functional activity and many different library molecules.

The difficulty in designing models that do this accurately is that the models need to include high order interactions while at the same time not creating so many free parameters in the system so as to cause the problem to be underdetermined.

Relating to the methods described herein, three algorithms have been developed that accomplish this goal. The first two are based on the idea that the structure of a molecule in a library can be explicitly related to its function by considering three components: 1) the covalent structure of the molecule, 2) the components of that structure that are common to many molecules in the library and 3) the properties of those components as they relate to the function in question. Mathematically, this can be expressed as:

$$f_{n(sequence)} = \Sigma_m \Sigma_r \Sigma_k C_{n,m,r} Q_{k,m} A_{k,r} \qquad (1)$$

Here, $f_n$ is the function of the nth molecule in the library, $C_{n,m,r}$ is a description of the covalent structure of the molecule where n is again the specific molecule in the library, m represents chemical entities that make up the molecule and r represents the positions of a set of structural elements made from those entities. For a peptide in a library, m and r could simply designate specific amino acids at specific positions in a sequence. However, m could also represent groups of amino acids and r groups of structural arrangements of those amino acids. $Q_{k,m}$ represents the assignment of properties to the chemical entities. There are k properties assigned to each of the m chemical entities. $A_{k,r}$ represents the weighting coefficient assigned to the different functional components of the molecule in terms of their properties and relates these structures and properties to the measured function. The third algorithm involves a machine learning approach based on a neural network that again relates structural components to function in a nonlinear manner, but does so without the explicit assignment of terms as seen in equation (1). All three approaches are fundamentally different from a description such as a consensus sequence, which might be described in a similar formalism as:

$$f_{n(sequence)} = \Sigma_m \Sigma_r C_{n,m,r} B_{m,r} \qquad (2)$$

Here components, for example individual amino acids, in the covalent structure are simply assigned a weight and added up (a purely linear approach).

The algorithms described here, have the option of assigning properties to each of the components that make up the molecular system (the Q term in the equation above, an encoder matrix in the machine learning algorithm described below), translating discrete species (e.g. a set of amino acids or a set of nucleic acid monomers) into sets of properties with continuous values. They then use a method for describing higher order interactions between components of the structures. For example, allowing for a specific property that arises only when there is an alanine in position 2 of a peptide at the same time that there is an arginine at position 7 and a valine at position 11. The difference between the algorithms is in the mechanisms that they use to describe these higher order interactions.

The first algorithm involves products of the sums described above. Here m simply represents an amino acid and r represents its position in the sequence. The higher order interactions arise in the products which generate cross terms and the cross terms represent interactions between components in the peptide that give rise to higher order properties. In this case, one performs a nonlinear optimization of the power series:

$$f_{n(sequence)} = \alpha_0 + \alpha_1 \Sigma_m \Sigma_r \Sigma_k C_{n,m,r} Q_{k,m} A_{k,r} + \alpha_2 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \alpha_3 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \ldots \quad (3)$$

Hear, $\alpha_i$ is a multiplier of the term and the other variables are as noted above. Note that the A and Q matrices can either be held constant in every sum or different values can be used in each sum, depending on the complexity of the structure and function being described.

The second approach is similar in principle, but uses a different mechanism for introducing the higher order interactions. Here, the equation itself is a single sum:

$$f_{n(sequence)} = \Sigma_m \Sigma_r \Sigma_k C_{n,m,r} Q_{k,m} A_{k,r} \quad (4)$$

However, the descriptions used for the structure and chemical properties of the components involved in this model directly incorporate the higher order structural entities in the description of the sequence. C again contains the sequence information and is fixed, but it contains that information in terms of a basis set of structures and chemistries. As such the index 'm' in this model represents groupings of particular amino acids. This could be individual amino acids or pairs of amino acids or sets of three amino acids.

Consider a model in which we describe the peptide sequences in terms of groups of three amino acids. There are 8000 combinations of 3 amino acids possible and therefore the index 'm' would range from 1 to 8000. The index 'r' in this model represents the structural arrangements of three amino acids. This is in terms of the physical position of the amino acids in the peptide. Thus in a model that used three amino acids in each basis structure, the structures could be all possible ways of placing 3 amino acids into a 12 residue long peptide. There are 220 ways of selecting 3 distinct positions in a 12 residue peptide and so r would range from 1 to 220. Q assigns chemical properties ('k' of them) to each of the 'm' combinations of amino acids. These properties are usually left as free parameters in the fit. A provides a coefficient for every member in the basis set. Once C and Q are combined, one will have assigned a particular set of 'k' properties to each of the 'r' structures. If there were 4 properties and 220 possible structural arrangements then A would have dimensions of 4×220. So the total number of free parameters in the fit is given by the number of elements in Q (8000×4 in the example above) and A (4×220 in the example above). As will be described later, sometimes it is useful to define Q once and then hold it constant and calculate A for many different samples. However, as it turns out, there is sufficient information in a 126,000 peptide array to accurately determine both Q and A without too much overfitting.

As outlined above, an accurate description of an antibody binding to peptide sequences is very useful in many contexts. It allows one to generalize from a specific set of, e.g., 126,000 peptides to all other peptides of that general length scale (for a 12 residue peptide, this would predict the binding to $20^{12} = 4 \times 10^{15}$ sequences). This can be used to predict binding to all possible sequences in a proteome, for instance, or to the sequences in a known antigen in order to map the epitope. As will be described below, it also organizes the binding information in useful ways, such that this information can more effectively used in enhancing the diagnostic capabilities of the peptide arrays when identifying disease states. A number of different non-limiting examples are given below which exemplify the utility of processes that use the equations developed via the data analysis described above to accomplish important tasks useful in medicine, research and molecular design.

The third type of algorithm described here is a machine learning approach. In general, such approaches achieve the same type of outcomes as the algorithms described above, but through optimization of a series of so-called hidden layers, matrices that transform an input matrix from one operation to an output matrix that feeds into the next operation. Nonlinearity is introduced by performing some nonlinear processing of the output matrix of one transformation before the subsequent transformation takes place. A common example of such a nonlinear process is to set all negative values of the matrix to zero. Many such nonlinear processes are known to those skilled in the art of machine learning and many neural network and related transformation sequences are also known to those skilled in the art. As was the case above, it is possible to build into the algorithm a means of feeding chemical information about the components into the algorithm or derive chemically relevant information from the optimized matrices of the algorithm (e.g. one can formulate the algorithm so that there is a counterpart of the Q matrix above that is referred to as an encoder matrix which translates describe amino acids into real-valued vectors).

It should be noted that besides interactions with other chemicals, there could be interactions with physical phenomena that one may use to obtain a data set based on a signal derived from interaction of one or more chemical structures with a physical phenomenon of interest. Such phenomenon may include, by way of example, light, other types of electromagnetic radiation, ionic radiation, electric fields, magnetic fields, temperature changes, pressure changes, proximity to materials (which may or may not be molecular), particle beams, plasmas, exposure to fluxes of electrons, protons, positrons or other subatomic molecules, exposure to atoms, ions or radicals that are not molecular, sheer forces, surface tension, and so forth.

Some of the non-limiting examples below will also demonstrate the ability to apply the same approaches to describe the binding of peptide sequences to a protein that is not an antibody. This approach can be used to predict binding of one protein to other proteins or binding partners (e.g., to a specific receptor on a cell) or to predict and refine specific ligands to proteins or other molecular complexes. These types of predictions may be useful in many different applications including, but not limited to, locating potential drug/vaccine targets, therapeutic lead discovery, design or optimization, creating synthetic antibodies, developing specific labels (e.g. fluorescent labels, or labels used in medical imaging), developing antimicrobial/antiviral compounds or developing targeting molecules that could be attached to known drugs and give them high affinity and specificity for a desired target.

NON-LIMITING EXAMPLES

Example 1: Characterizing a Monoclonal Antibody

Both equations (3) and (4) were used to a fit of the fluorescence data resulting from binding a labeled molecule of the monoclonal antibody DM1A (a monoclonal antibody for tubulin frequently used in histological staining of cells) to a peptide array. Commercial arrays (from HealthTell, Inc.) were used for this purpose. They produce arrays of ~126,000 unique peptides and bind either specific antibodies or serum to the arrays using assays which are standard in that company and essentially the same as those described in the literature (see References 11-14). In brief, the assay involves adjusting the concentration of sample by dilution into a standard buffer and applying this to an array of peptides on a silica surface that has been treated to decrease any background binding. The array is washed, a fluorescently labeled secondary antibody that will bind to the antibody or antibodies in the sample is then applied, excess washed off, and the array is dried and imaged on a commercial imaging system. The image is processed to provide a value of fluorescence intensity for each peptide on the array. The dynamic range of the assay is roughly 1000:1, depending on the sample and the background binding.

Figure 1:
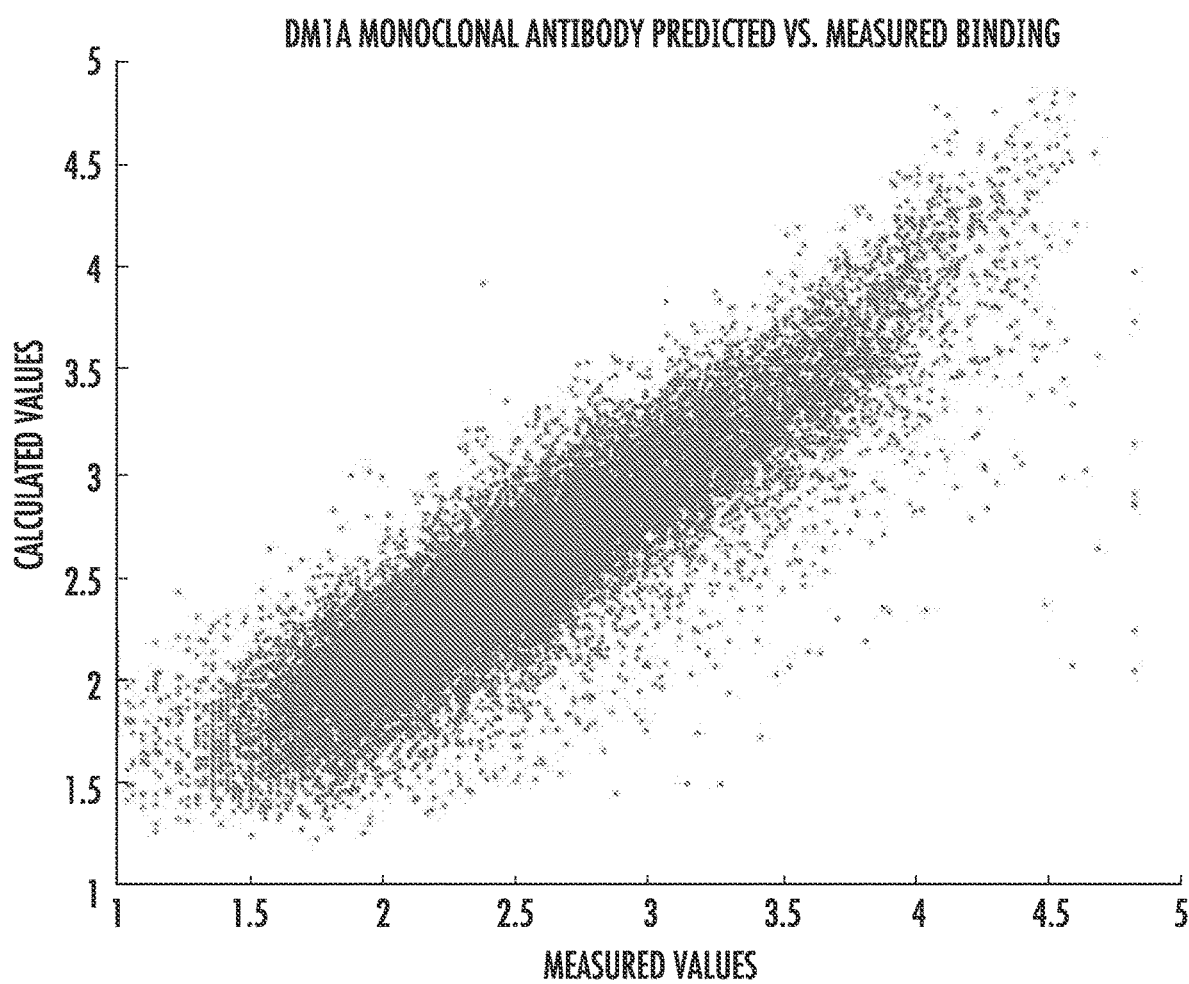
FIG. 1. Results from a fit using equation 3 of binding data of the monoclonal antibody DM1A to an array of peptides. The peptide sequences used in this prediction are unique from those used in the fit. The Pearson correlation coefficient between the predicted and measured data is 0.90. Values shown are the log base 10 of measured values.

The results of fitting the binding data for the monoclonal antibody DM1A to equation 3 are shown in FIG. 1. On the x-axis is the log of the measured binding data. On the y-axis are the predicted values (also on a log base 10 scale). Note that these are true predictions. The binding data that was used to train the algorithm was based on a completely different set of peptide sequences than the peptide sequences being predicted here. The Pearson Correlation Coefficient between the predicted and measured values was 0.90.

Figure 2:
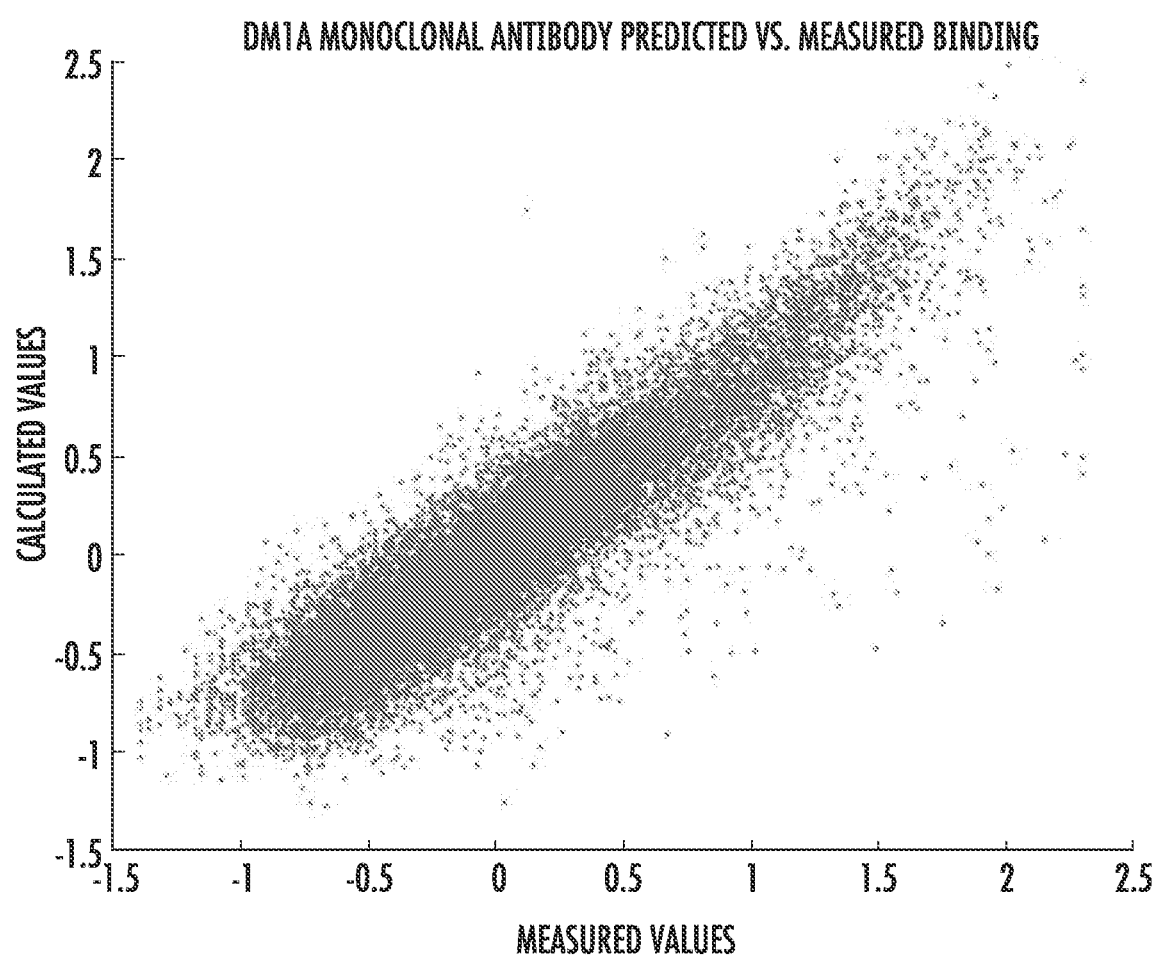
FIG. 2. Results from a fit using equation 4 of binding data of the monoclonal antibody DM1A to an array of peptides. The peptide sequences used in this prediction are unique from those used in the fit. The Pearson correlation coefficient between the predicted and measured data is 0.91.

Similarly, equation (4) was applied to the same data set and the results of prediction (again of peptide sequences not used in the fit) is shown in FIG. 2. Note that in this case normalization to the median was performed before the log base 10 was taken of the data (hence the change in scale). Here the Pearson Correlation coefficient is 0.91.

One can use the fits from binding of a particular antibody to map the epitope(s) it interacts with in an antigen. The antigen that DM1A was raised to is human alpha tubulin. The amino acid sequence of tubulin is shown below and the known cognate epitope of DM1A is identified (bolded and underlined):

Alpha Tubulin sequence showing DM1A epitope:

(SEQ ID NO. 2)
MRECISIHVGQAGVQIGNACWELYCLEHGIQPDGQMPSDKTIGGGDDSF

NTFFSETGAGKHVPRAVFVDLEPTVIDEVRTGTYRQLFHPEQLITGKED

AANNYARGHYTIGKEIIDLVLDRIRKLADQCTGLQGFLVFHSFGGGTGS

GFTSLLMERLSVDYGKKSKLEFSIYPAPQVSTAVVEPYNSILTTHTTLE

HSDCAFMVDNEAIYDICRRNLDIERPTYTNLNRLIGQIVSSITASLRFD

GALNVDLTEFQTNLVPYPRIHFPLATYAPVISAEKAYHEQLSVAEITNA

CFEPANQMVKCDPRHGKYMACCLLYRGDVVPKDVNAAIATIKTKRTIQF

VDWCPTGFKVGINYQPPTVVPGGDLAKVQRAVCMLSNTTAIAEAWARLD

HKFDLMYAKRAFVHWYVGEGMEEGEFSEAREDMAALEKDYEEVGVDSVE

GEGEEEGEEY

Figure 3:
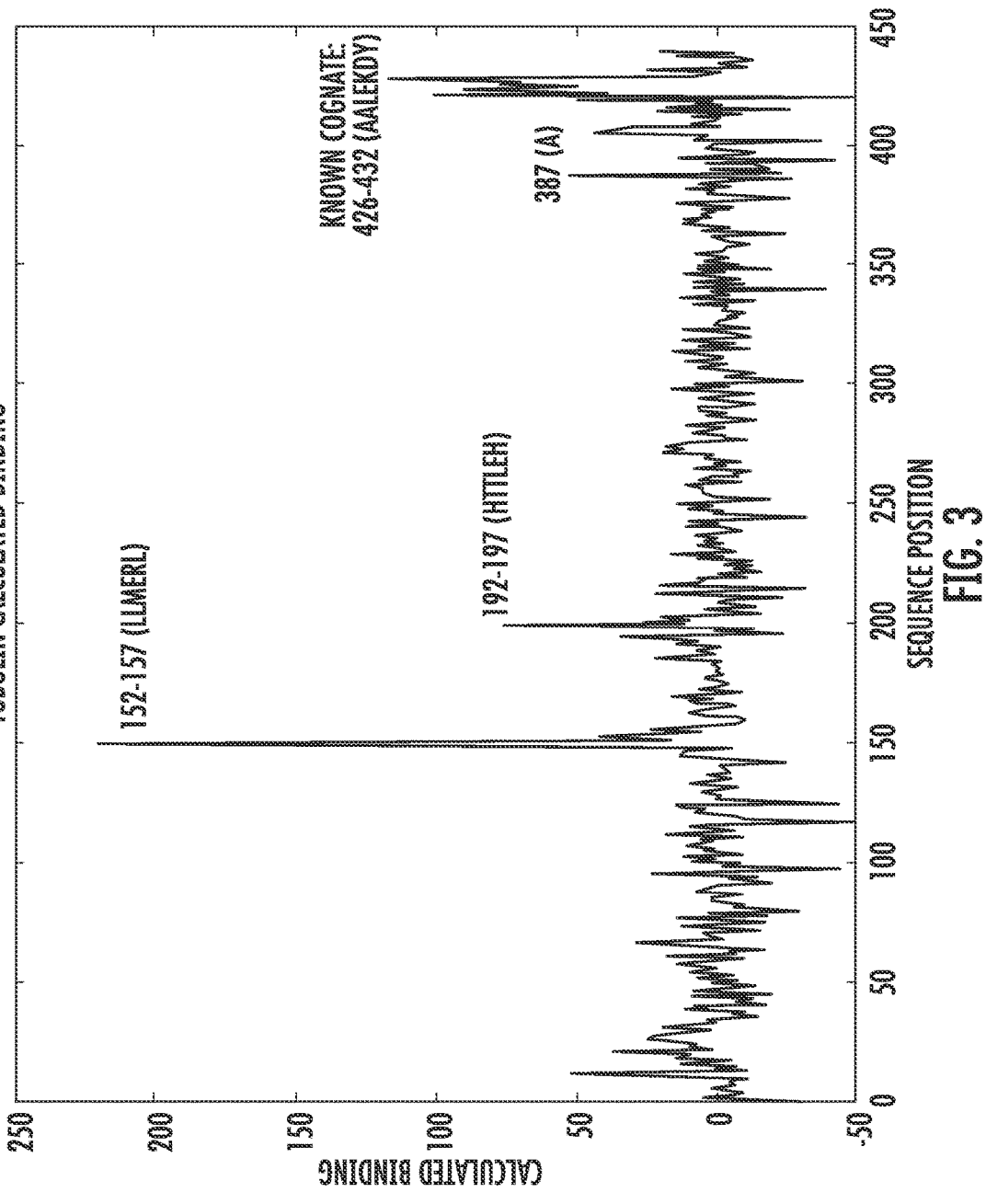
FIG. 3. Calculated binding to human alpha tubulin using a fit to equation 4 of the peptide array. The known cognate epitope is the wide feature to the right, but there are a couple other prominent binding regions as well.
Figure 4:
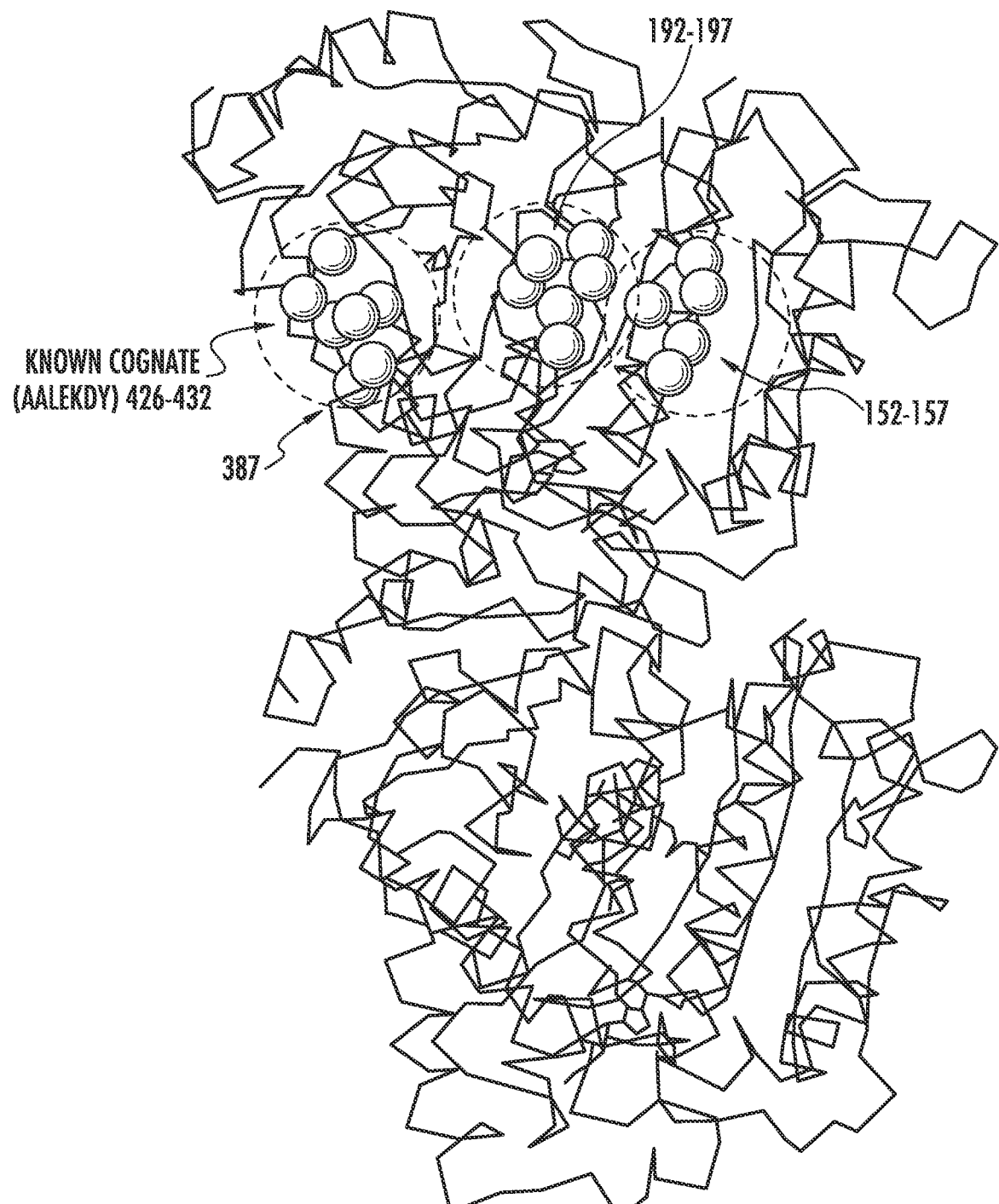
FIG. 4. Positions of the amino acids identified as strong binding by the calculation. All of these are present in close proximity (within 2 nm) of the known cognate sequence on the same surface of the protein.

A map of the binding of DM1A predicted by a fit to equation 4 is shown in FIG. 3. Note that in FIG. 3, the prominent, wide feature to the right is the published cognate epitope. However, the fit identified some other significant potential binding sequences. FIG. 4 shows the positions of these sequences in the structure. Note that they are all in relatively close proximity on the surface of alpha tubulin, suggesting that they may indeed all be involved in stabilizing the binding of this monoclonal antibody.

Figure 5:
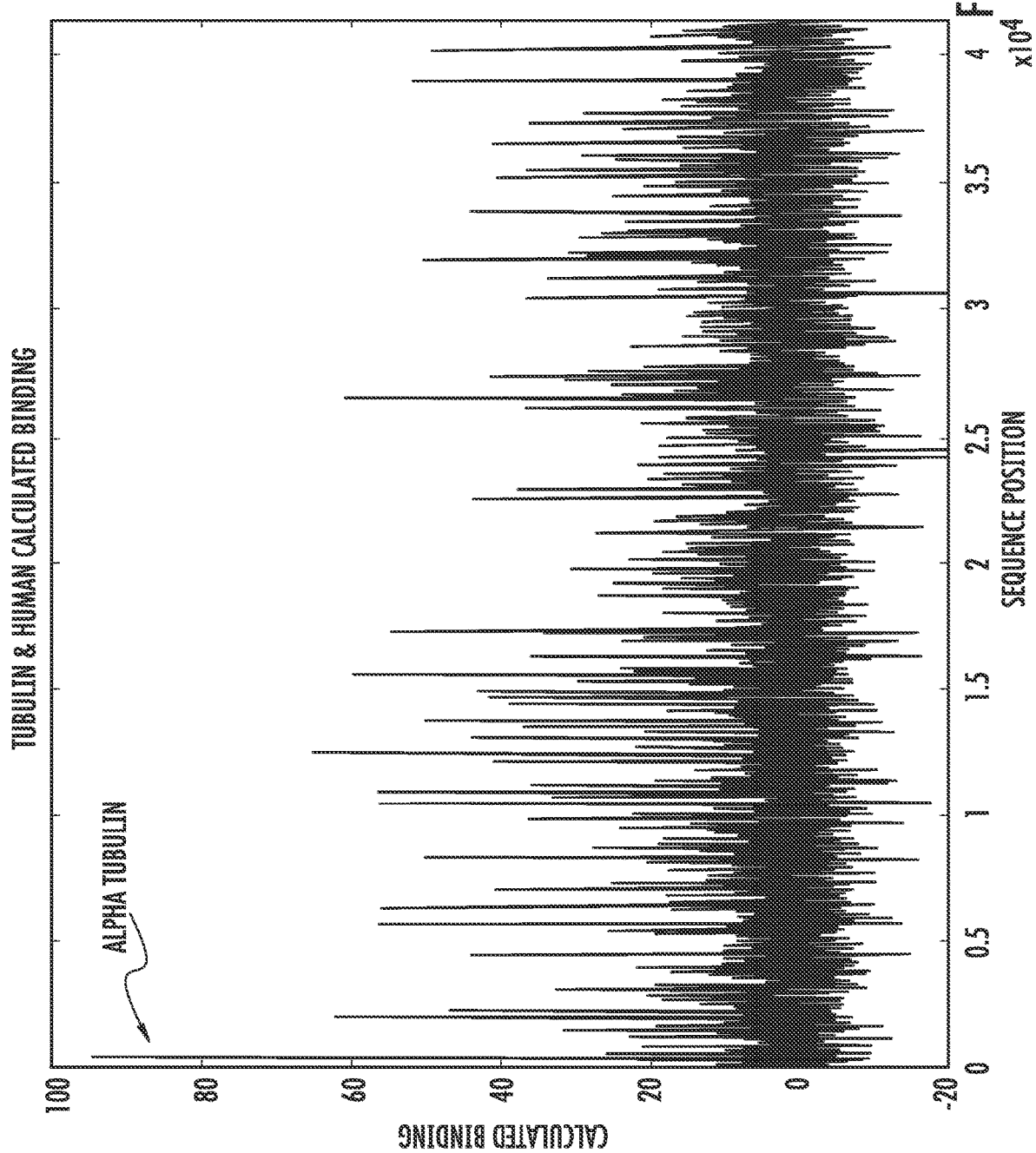
FIG. 5. Calculated binding to alpha tubulin and 100 other similarly sized human proteins using a fit of the peptide array data (which did not contain any cognate sequences) bound to the monoclonal antibody DM1A. Note that the x-axis shows the sequence position after concatenating the sequences of all 100 proteins. The highest binding protein is indeed alpha tubulin.

Example 2: Predicting the Antigen of an Isolated Antibody from a Group of Other Proteins It is also possible to use fits such as the one above to identify the antigen of a specific antibody among a list of possible antigens. FIG. 5 shows the binding predicted by a fit using equation 4 of DMA1 binding to the alpha tubulin gene and 100 similarly sized human genes. Note that the sequences of the proteins are shown as contiguous and just numbered from the beginning to the end. Alpha tubulin is predicted to bind most strongly of all proteins sampled.

Figure 6:
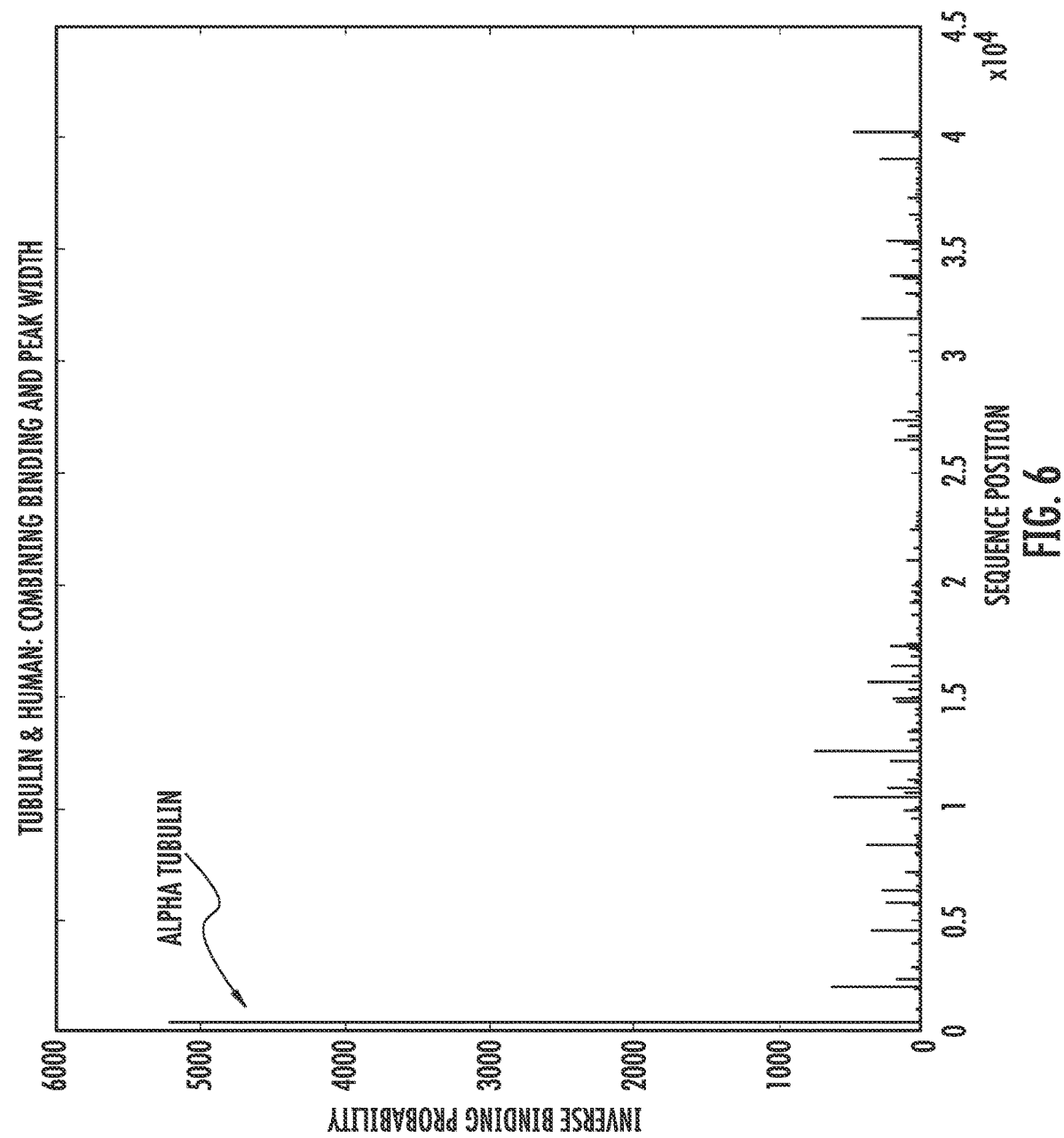
FIG. 6. The binding is shown as an inverse probability (based on binding rank), combining the probability of having multiple contiguous windows or frames of sequence all bind to the antibody. The x-axis is the same as FIG. 5.

However, there are a number of other proteins that are not much weaker than alpha tubulin and if larger groups of proteins are considered, there could easily by stronger binding proteins. To better discriminate antigen binding from binding to less specific targets, one can take advantage of the biology of specific antibody binding. In particular, one generally might expect two characteristics of a true epitope. First, our algorithm considers binding over a window, in the case shown in FIG. 5, a 9 amino acid window was used. One would expect that the epitope might be present in multiple contexts within a large enough window. In other words, one would expect multiple contiguous windows would bind with similar intensity, as long as they contain the epitope (each binding signal is to a window of residues in the protein and from one point to the next, the window is shifted by one residue, so a particular epitope could be present in many such windows). To take advantage of this fact, we give a stronger weighting to binding events in which contiguous windows have substantial binding. The result of such a process is shown in FIG. 6. Here the binding is shown as an inverse probability calculated by considering the binding rank of each sequence among all sequences and then determining the probability of contiguous binding of several windows at high rank.

Figure 7:
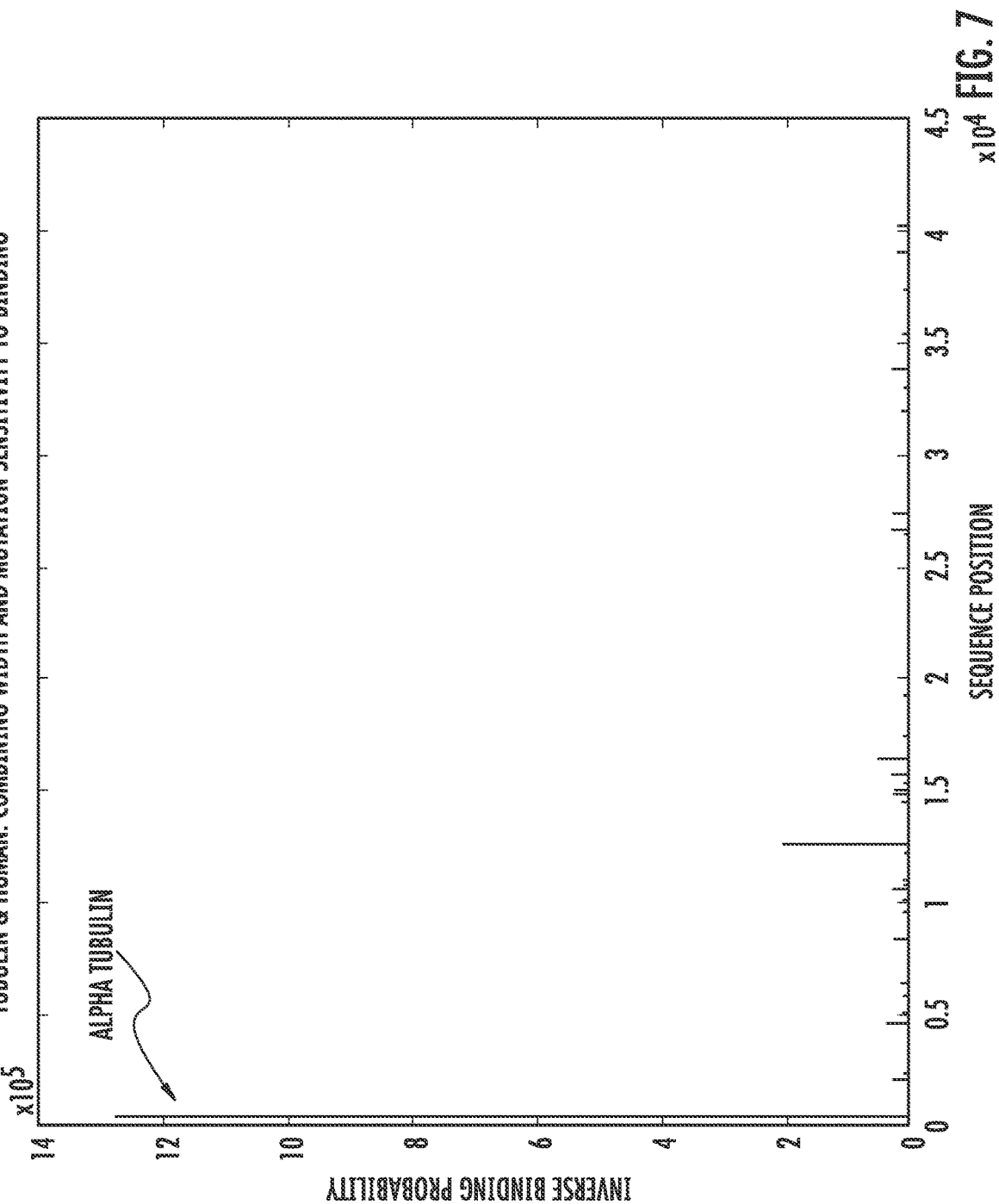
FIG. 7. The dominance of the actual antigen is further enhanced by determining what sequences are most sensitive to point mutations and using that as an additional factor in calculating prominence of each sequence region in the list of proteins. The x-axis is the same as FIG. 5.
Figure 8:
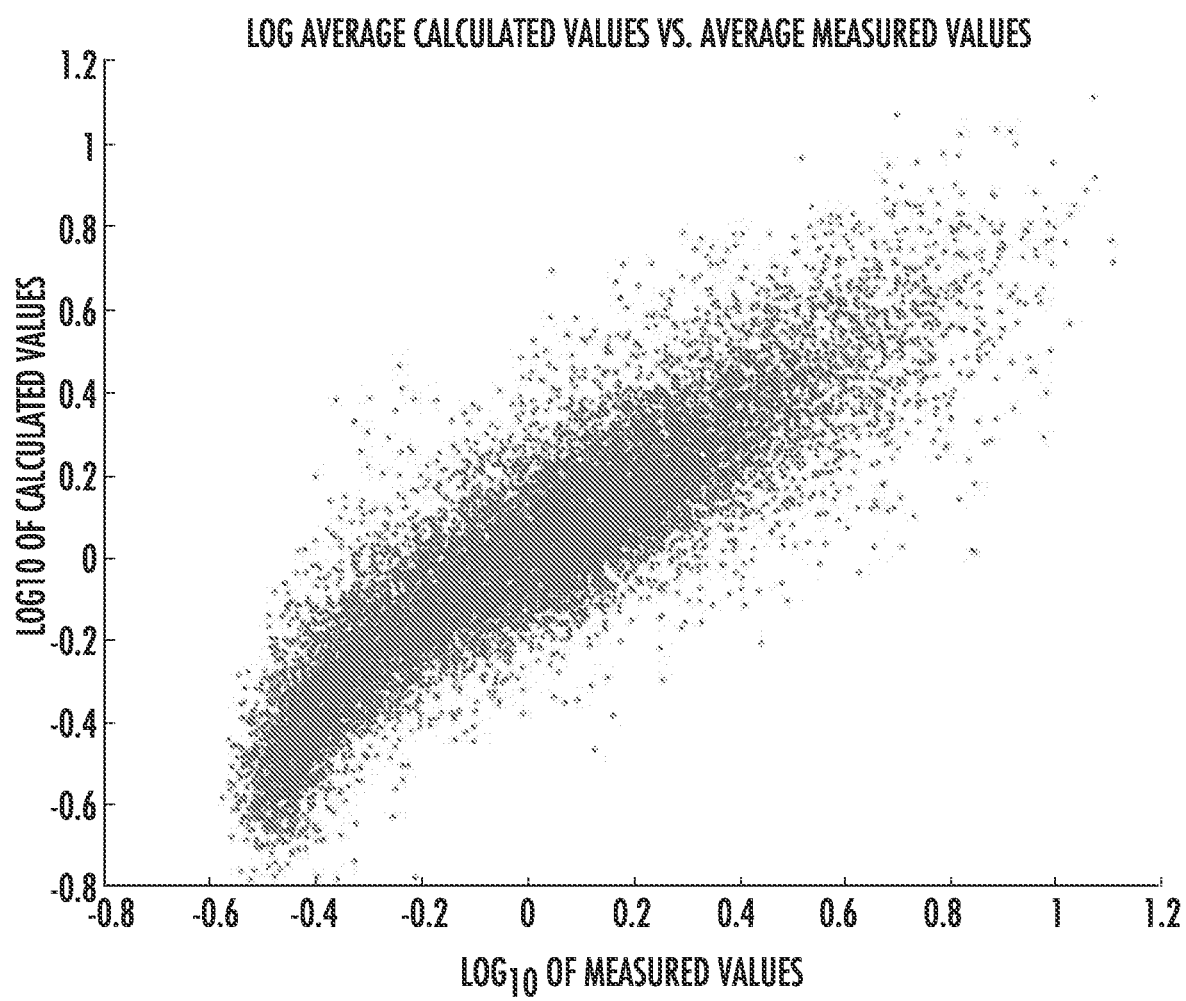
FIG. 8. Measured binding values vs. a fit to equation 4 of the average of the Hepatitis B and C patient data (Total IgG binding). The data was median normalized and the log base 10 was taken before fitting. The Pearson correlation between the measured and predicted values was 0.89. Note that the binding shown is from peptides that were on the array but not used in training the model.
Figure 9:
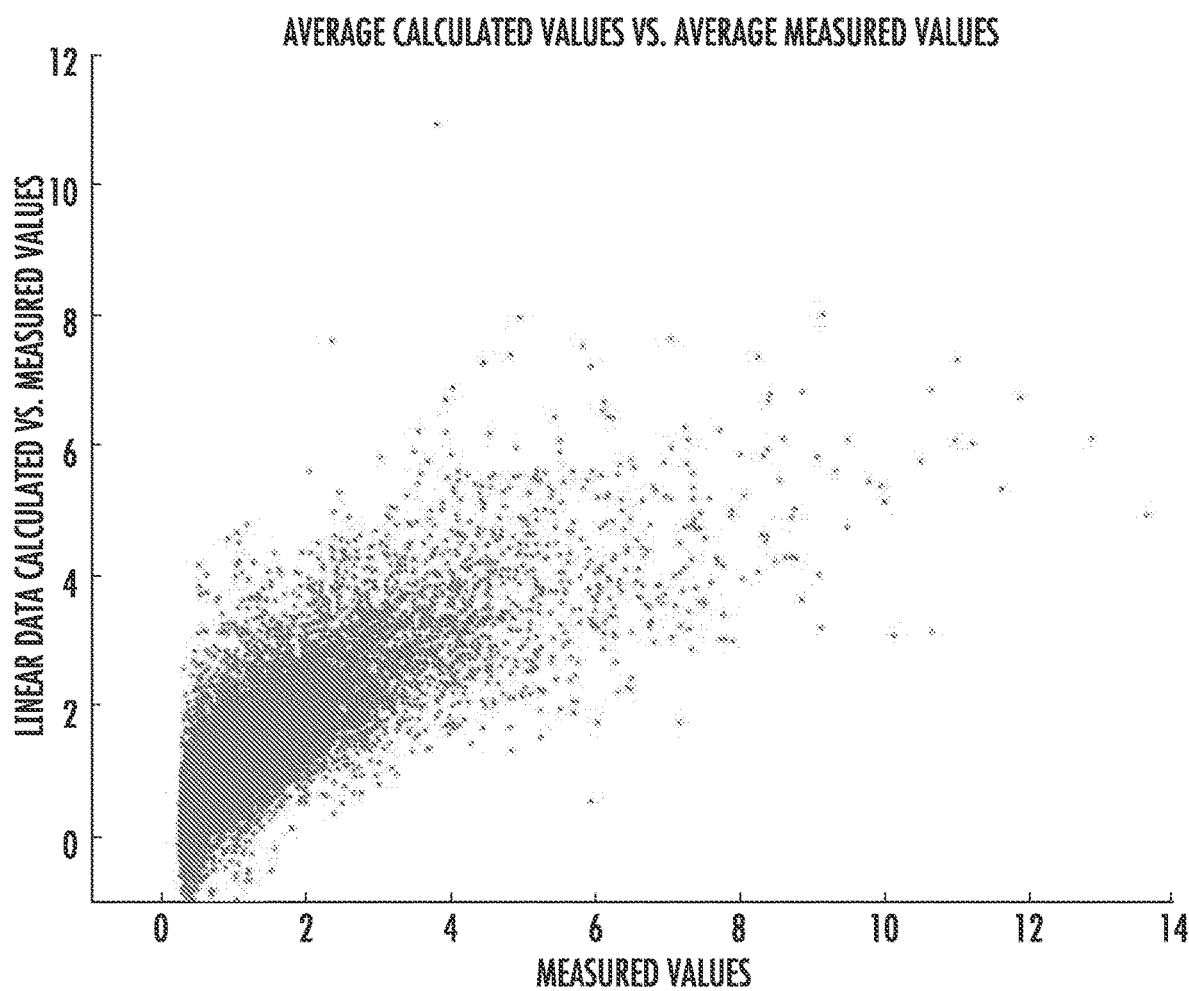
FIG. 9. Measured binding values vs. a fit to equation 4 of the average of the Hepatitis B and C patient data. The data was median normalized but fit on a linear scale (not log). The Pearson correlation between the measured and predicted values was 0.78. Note that the binding shown is from peptides that were on the array but not used in training the model.
Figure 10:
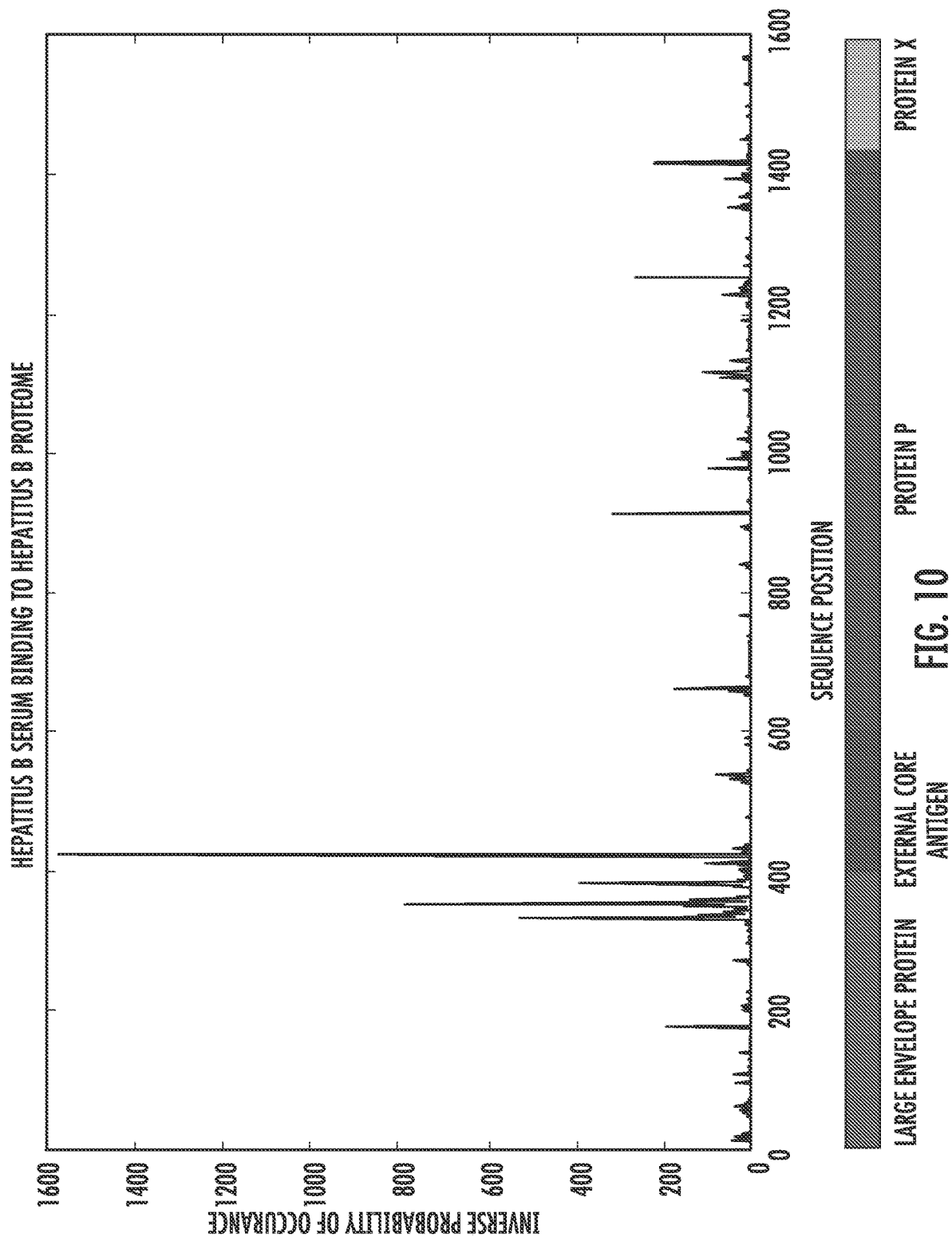
FIG. 10. Calculated binding of Hepatitis B patient serum (based on a fit using equation 4 of the average of 44 Hepatitis B infected samples) to a tiled set of peptides covering the Hepatitis B proteome. What is plotted on the y-axis is the rank-based probability of the observed binding value for each peptide.
Figure 11:
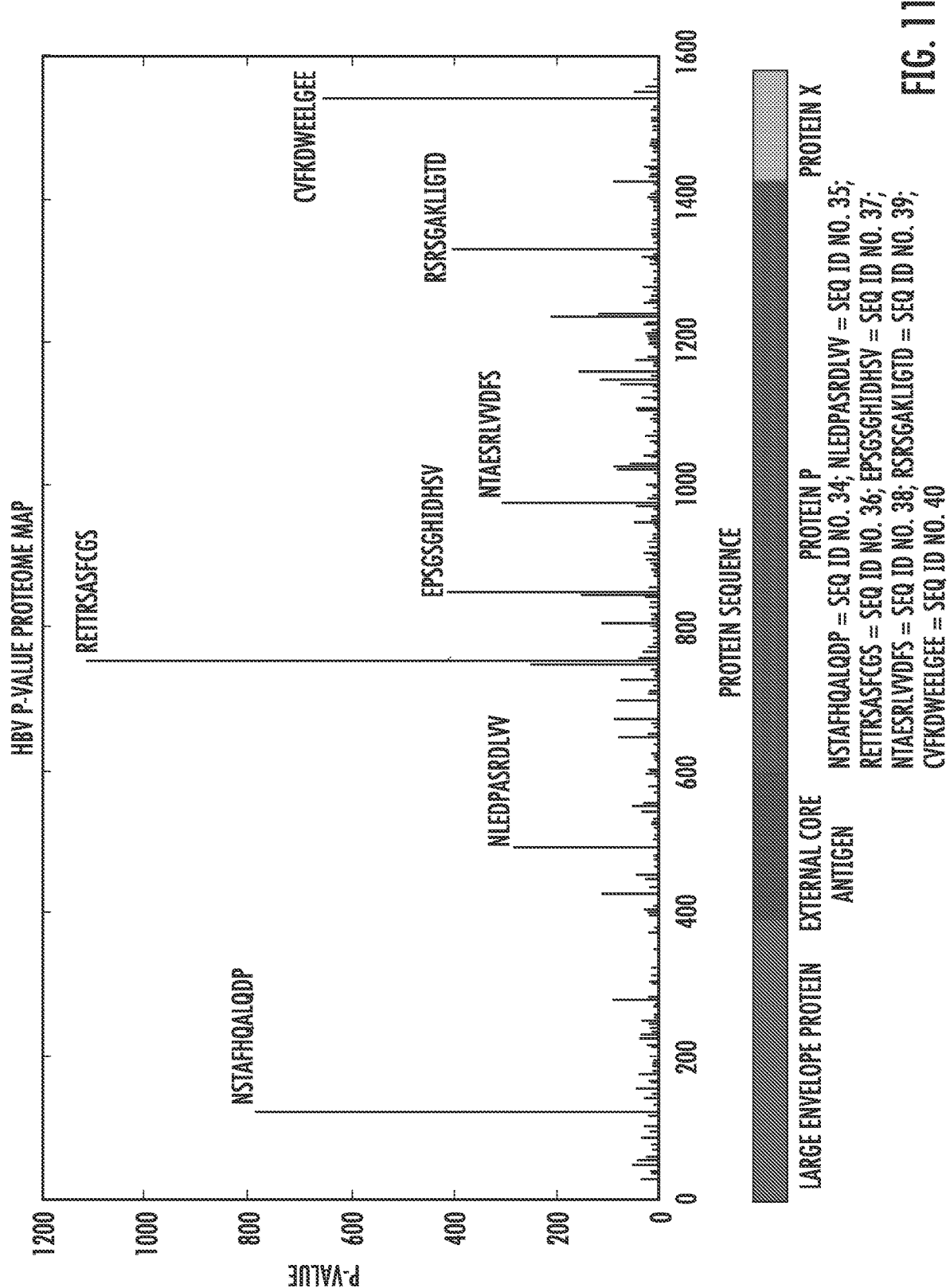
FIG. 11. Map of specific sites in the Hepatitis B proteome where there were differential immune responses between Hepatitis B and Hepatitis C patients. The p-values were obtained from a 2-sided Ttest comparing the predicted binding of IgG in serum from Hepatitis B patients to a tiled set of peptides covering the Hepatitis B proteome to the predicted binding of Hepatitis C patients to the same tiled set of peptides.
Figure 12:
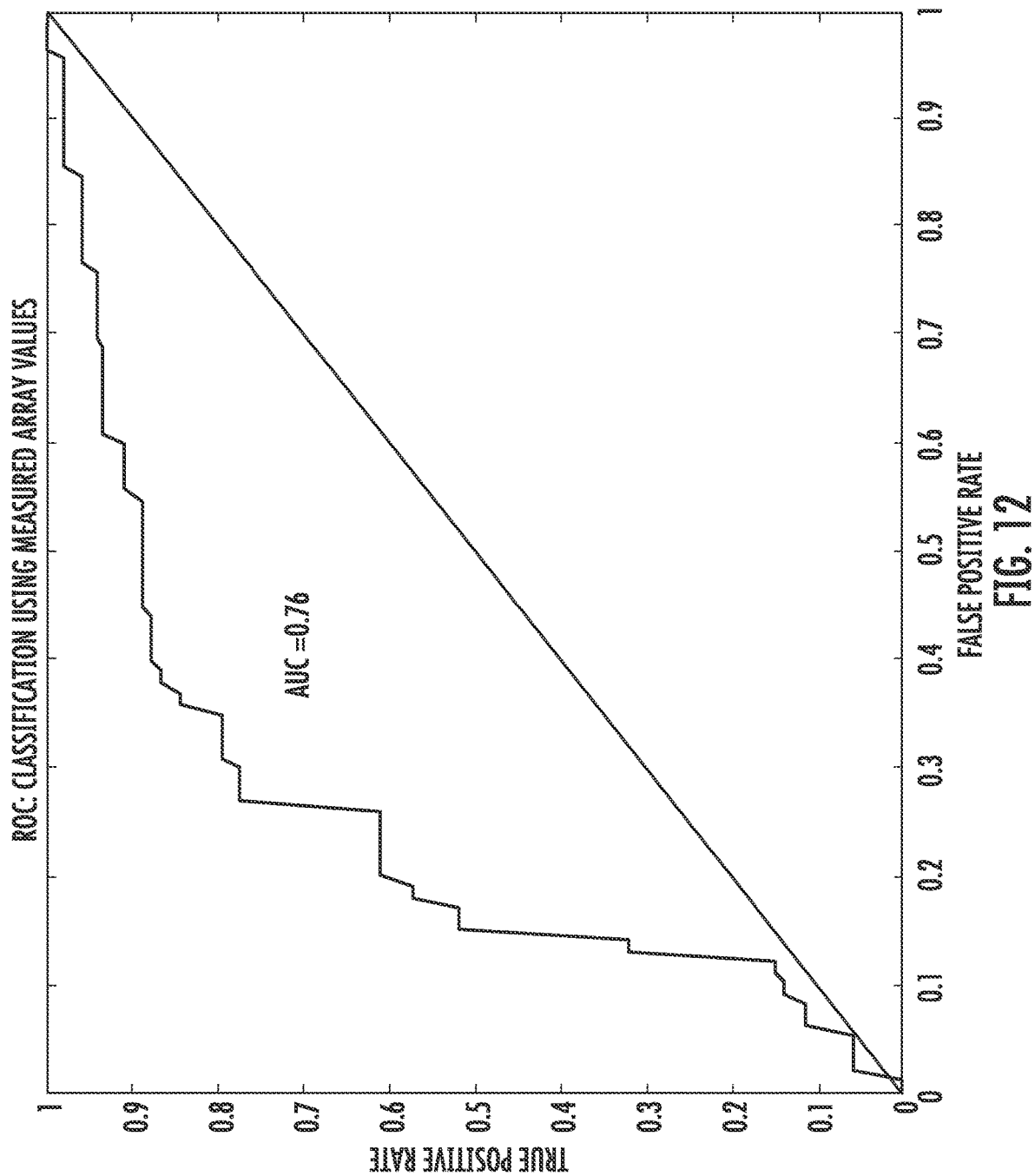
FIG. 12. Receiver operator curve of support vector machine classification of the original measured binding data from the peptide array comparing 44 samples from Hepatitis B and 44 samples from Hepatitis C.
Figure 13:
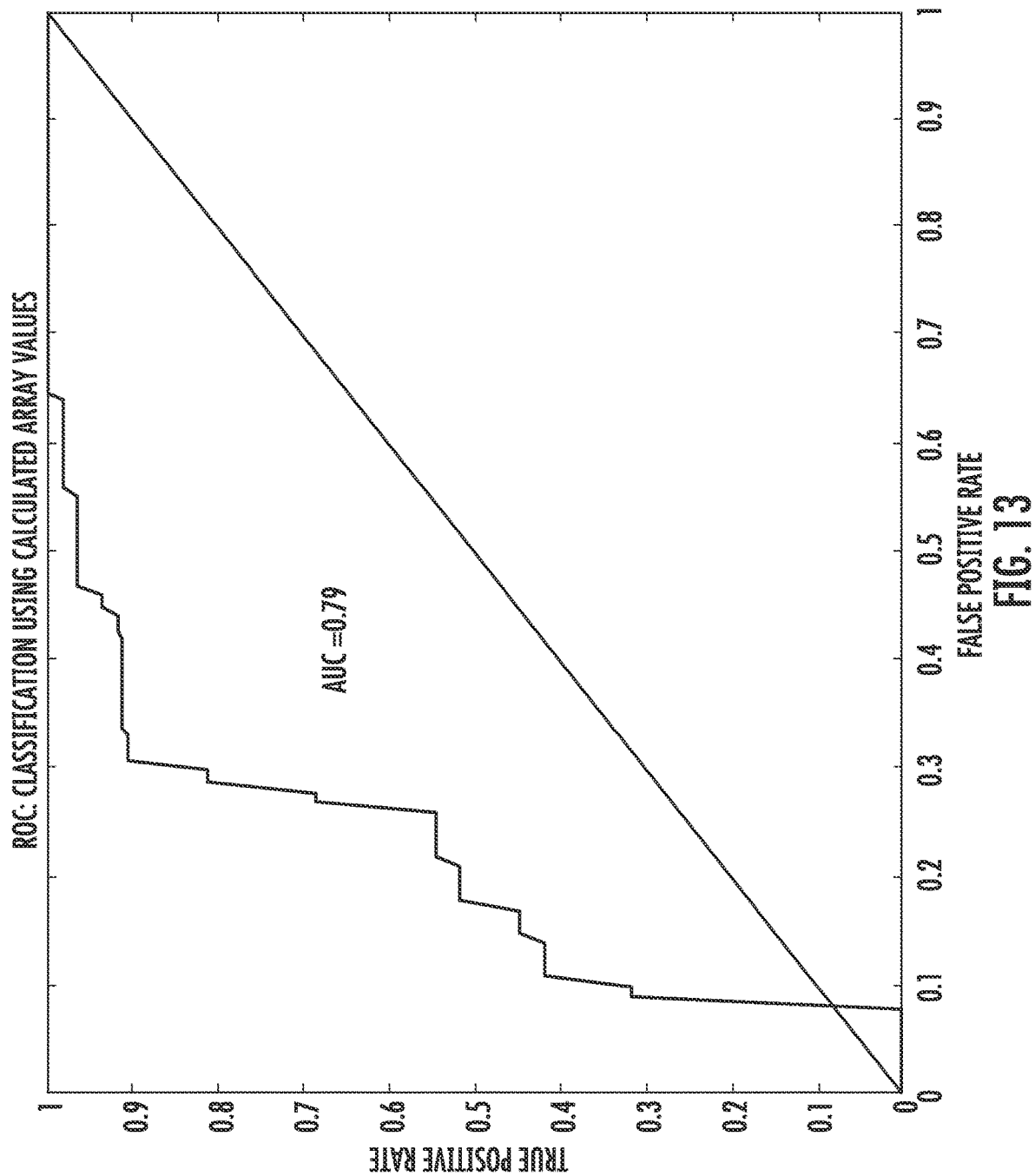
FIG. 13. Receiver operator curve of support vector machine classification of calculated binding data from the peptide array comparing 44 samples from Hepatitis B and 44 samples from Hepatitis C.
Figure 14:
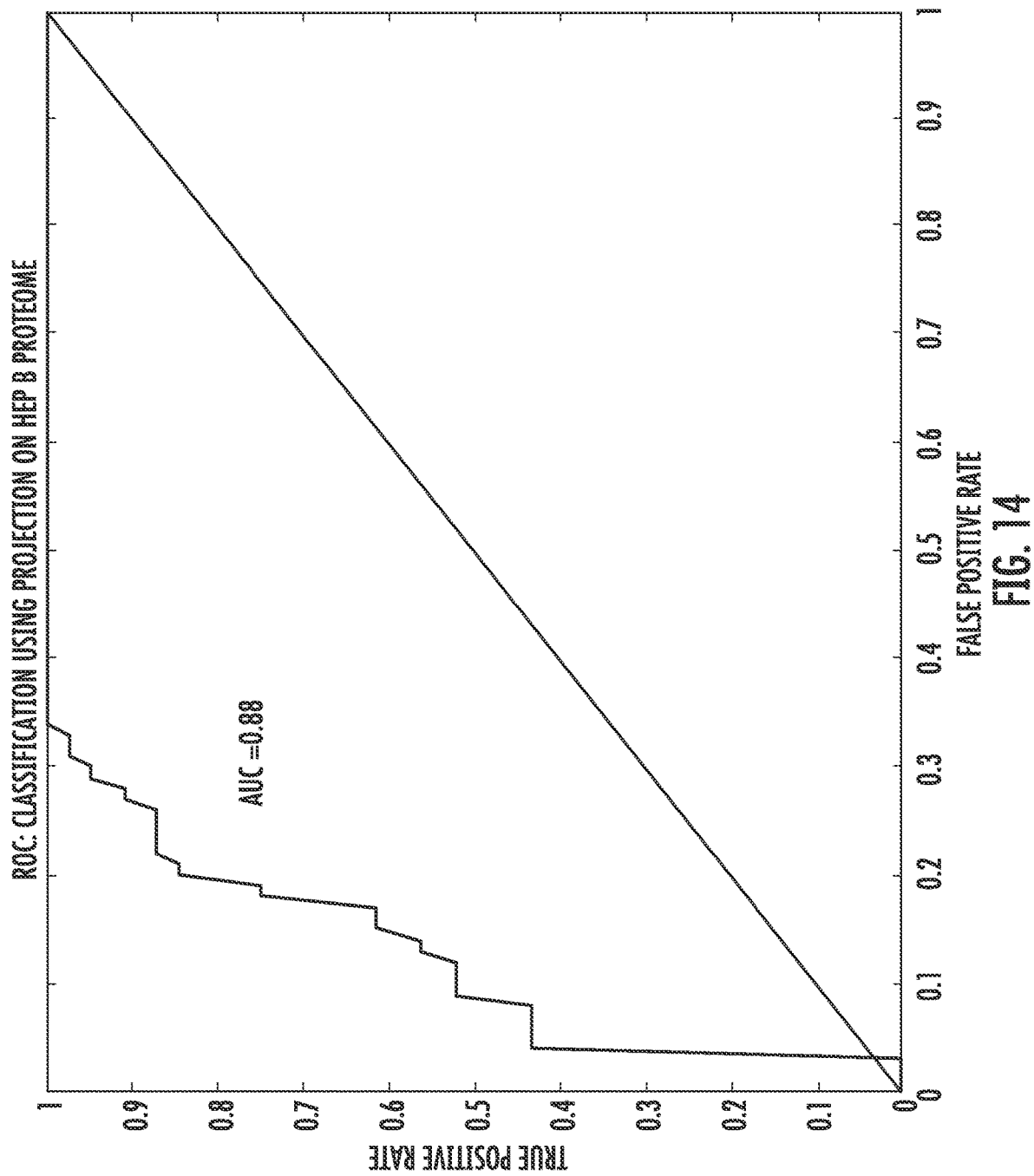
FIG. 14. Receiver operator curve of support vector machine classification of calculated binding data to the Hepatitis B tiled proteome comparing 44 samples from Hepatitis B and 44 samples from Hepatitis C.
Figure 15:
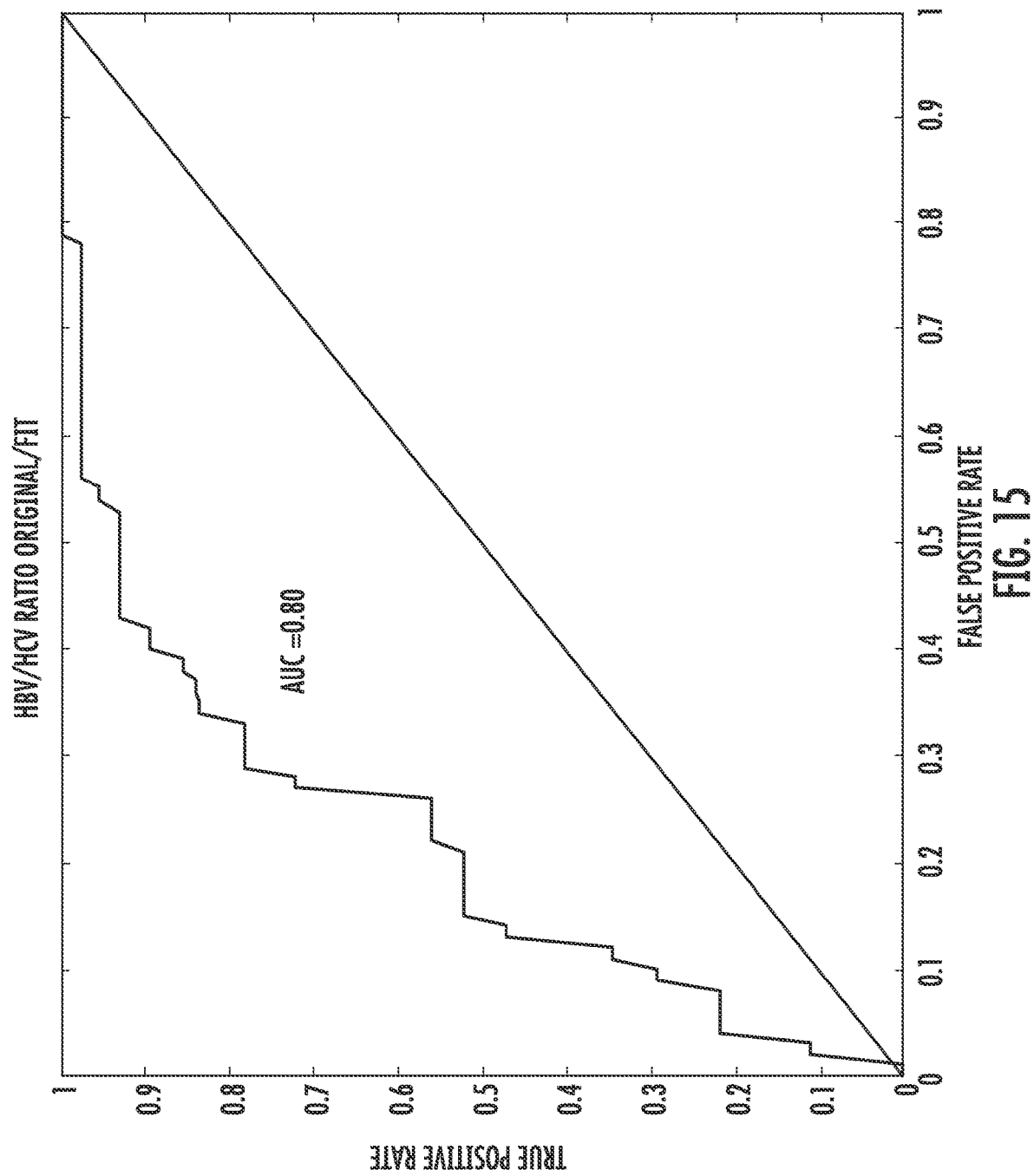
FIG. 15. Receiver operator curve of support vector machine classification of original measured data from the peptide array divided by the calculated binding data to the peptide array comparing 44 samples from Hepatitis B and 44 samples from Hepatitis C.
Figure 16:
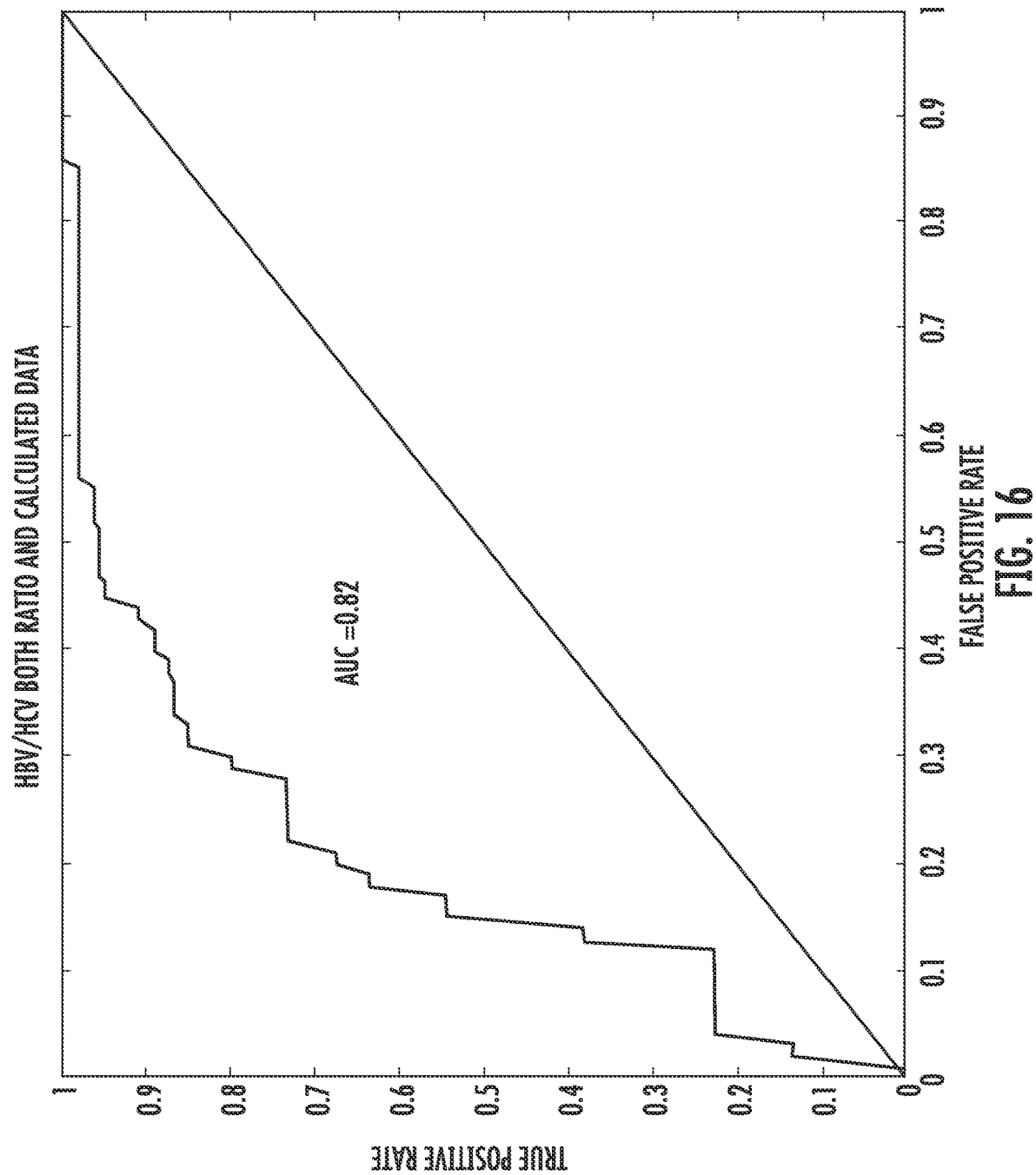
FIG. 16. Receiver operator curve of support vector machine classification of original measured data from the peptide array divided by the calculated binding data to the peptide array as well as the values from the calculated binding to the peptide array comparing 44 samples from Hepatitis B and 44 samples from Hepatitis C.

One can go one step farther in imposing biological constraints on the system. True epitopes are also usually very sensitive to point mutations. Because this is a calculated system, it is possible to calculate the effect of many point mutations on each sequence window in the list of 100 proteins and quantitate the effect of mutation. Again, the probability of high mutational sensitivity (again by rank) can be combined with the probability binding in multiple contiguous window, cleaning up the distinction farther as shown in FIG. 7. In this case, mutational sensitivity was determined for each peptide that had significant binding by replacing each amino acid with four other amino acids and taking a geometric average of the resulting fractional change that resulted.

Other biological criteria can also be incorporated into the process, again facilitated by the fact that we can calculate the expected behavior. As an example, the monoclonal antibody 4C1 (raised to thyroid stimulating hormone receptor, TSHR, having the cognate epitope QAFDSH (SEQ ID NO. 3) was analyzed using the same basic process outlined above. In this case, the epitopes identified as having the highest binding were from two proteins out the hundred human proteins plus TSHR. The highest ranked protein was human NF-kappa-B-activating protein which as a sequence in it that was a repeat of mostly lysine and arginine: KKRRKKKSSKRK (SEQ ID NO. 4). Long runs of positively charged amino acids were purposely excluded when designing the peptide arrays used in these studies. Apparently, this caused the calculated binding function to give an erroneous answer (there is always low level nonspecific binding associated highly positively charged species in the arrays picked up by the fit). However, one can scramble this sequence without much change in its binding and use that as a criterion for elimination; true epitopes depend not only on composition, but order. That effectively eliminates this sequence sending the TSHR sequence to the top of the list.

Thus a key point is that by having a general equation relating binding to sequence for an antibody, not only can one predict the binding to specific sequences in a large number of candidate antigens, but one can apply known biological constraints to the system, such as the need to bind in multiple contiguous sequence windows, the known sensitivity of true epitopes to point mutation, and the fact that true epitopes depend on order, not composition.

Example 3: Determining the Epitopes that Distinguish Clinically Relevant Infections Another application of computational representations of binding is in identifying the antigens involved in disease responses. This is important, both in vaccine production and in the identification of potential drug targets. Shown in FIG. 8 is a fit of the log of the binding values from an average of 44 patients infected with Hepatitis B. The Pearson correlation coefficient between the log of the measured and log of the calculated values is about 0.89. FIG. 9 shows a similar fit of data in the linear form (no log), resulting in a Pearson correlation coefficient of 0.78 between measured and calculated values. The maps and analysis that followed used the linear fits as these emphasis the high binding values. FIG. 10 shows a map of the calculated binding for tiled sequences that make up the Hepatitis B proteome. One can see that there is a region of unusually strong binding in the so-called S-antigen, which is an antigen often used in immunological assays for the disease. However, if one fits an average of 44 patients infected with Hepatitis C, one sees that this region of the Hepatitis B proteome is also higher than average binding in those patients. Using the fact that we can project each of the patient samples onto the Hepatitis B proteome sequence, however, we can overcome this problem.

For the current study, the data from an average of all Hepatitis B and C samples was performed and used to determine Q in equation 4. This Q was held constant as each of the individual samples was refit, varying just A. These 88 equations (from the 44 Hepatitis B and 44 Hepatitis C samples) were used in a Ttest to calculate a p-value between Hepatitis B and Hepatitis C calculated values for each peptide window in the Hepatitis B proteome. The p-values were then inverted and plotted against the sequence, showing which peptides had strong differences between patient responses to the two viruses (FIG. 11). A comparison of the sequences highlighted by this approach in the Hepatitis B genome with those noted to be antigens for Hepatitis B from previous studies (the website www.iedb.org supports a database of infectious disease epitopes), showed that several of the predicted epitopes had been previously identified by orthogonal methods.

This demonstrates that it is possible to use projections of the immune response made possible by the fits to equation 4 in order to map potential antigens and epitopes within the sequence of proteins thought to be involved in the disease. This can be applied to the production of vaccines and to the identification of therapeutic targets.

Example 4: Using Calculated Binding Based on Peptide Arrays to Enhance the Diagnostic Capabilities of Those Arrays In Example 3, comparing the projection of equations fit using 44 Hepatitis B samples to 44 Hepatitis C samples onto the Hepatitis B proteome made it possible to identify potential antigens and epitopes within the Hepatitis B proteome that distinguish responses to it from patient responses to Hepatitis C. One can take this further by using the calculated values for each sample in a classification analysis as part of a diagnostic to differentiate Hepatitis B and C infections.

As a reference, the ROC (receiver operator curve) obtained for the measured dataset itself has an area of ~0.76 (AUC, Table 1, FIG. 12) using Support Vector Machine as the classification approach. (Note, the samples used in this analysis were purposely chosen to be difficult to distinguish making it easier to determine if the application of the algorithm allowed better resolution of the two diseases.) One can also perform the classification using the calculated binding values for the peptides in the original array. This gives a slightly higher AUC (0.79, FIG. 13, Table 1). It is also possible to project the calculation for each sample independently onto the Hepatitis B proteome and then classify using those values. Now the AUC climbs to 0.88 (FIG. 14, Table 1). Clearly using the known biology of the disease to focus the reactivity of the array greatly helps. Interestingly, when the calculated binding is either subtracted from the original data or the ratio between it and the original data is taken, this remaining information also resolves the diseases somewhat better than does the original measured data itself, giving an AUC of 0.80 (FIG. 15, Table 1). Using both the calculated values and the left over values (ratio in this case) in the same classification improves the fit further to about 0.81 AUC (FIG. 16).

TABLE 1

| Area Under the ROC (average of five analyses) | |
|---|---|
| Classification type | AUC |
| Classification using original data | 0.76 |
| Classification using original fit and recalculated data | 0.79 |
| Classification using calculated Hepatitis B proteome data | 0.88 |
| Classification using ratio of original to recalculated data | 0.80 |
| Classification using ratio data and recalculated data | 0.81 |

The error in the area under the curve (AUC) is less than 0.01.

Again, a key advantage of having developed an equation to represent the binding of each sample is that it allows one to use our knowledge of biology and chemistry in enhancing the function of the arrays. In this case, we are using the Hepatitis B proteome to focus the information from the original array onto sequences most pertinent to the specific disease analysis. In addition, the information that is extracted during the calculation is apparently inherently different from the disease specific information that is left behind (the information not extracted by the fitting algorithm). As a result, using these two sources of information separately is apparently more powerful as classifying than using either alone.

Those skilled in the art would understand that one could take advantage of the ability to calculate binding to peptides in other ways that would potentially enhance diagnosis or classification. For example, one could perform feature selection not via statistical methods (e.g. Ttest) by rather by searching for peptides in the original array that were most sensitive to mutagenesis or that had strong dependence on the order of the amino acids. One could project the equation against very large numbers of random peptides, creating much larger in silico arrays than the original array, potentially finding sequences that would do a better job in classification. One could use this approach, in fact, to design smaller arrays, specific to a particular clinical diagnostic, prognostic or monitoring task. One may also be able to use the elements of the equations in other combinations to create datasets that better differentiated disease as well.

Example 5: Finding the Binding Site of a Protein to its Receptor

Figure 17:
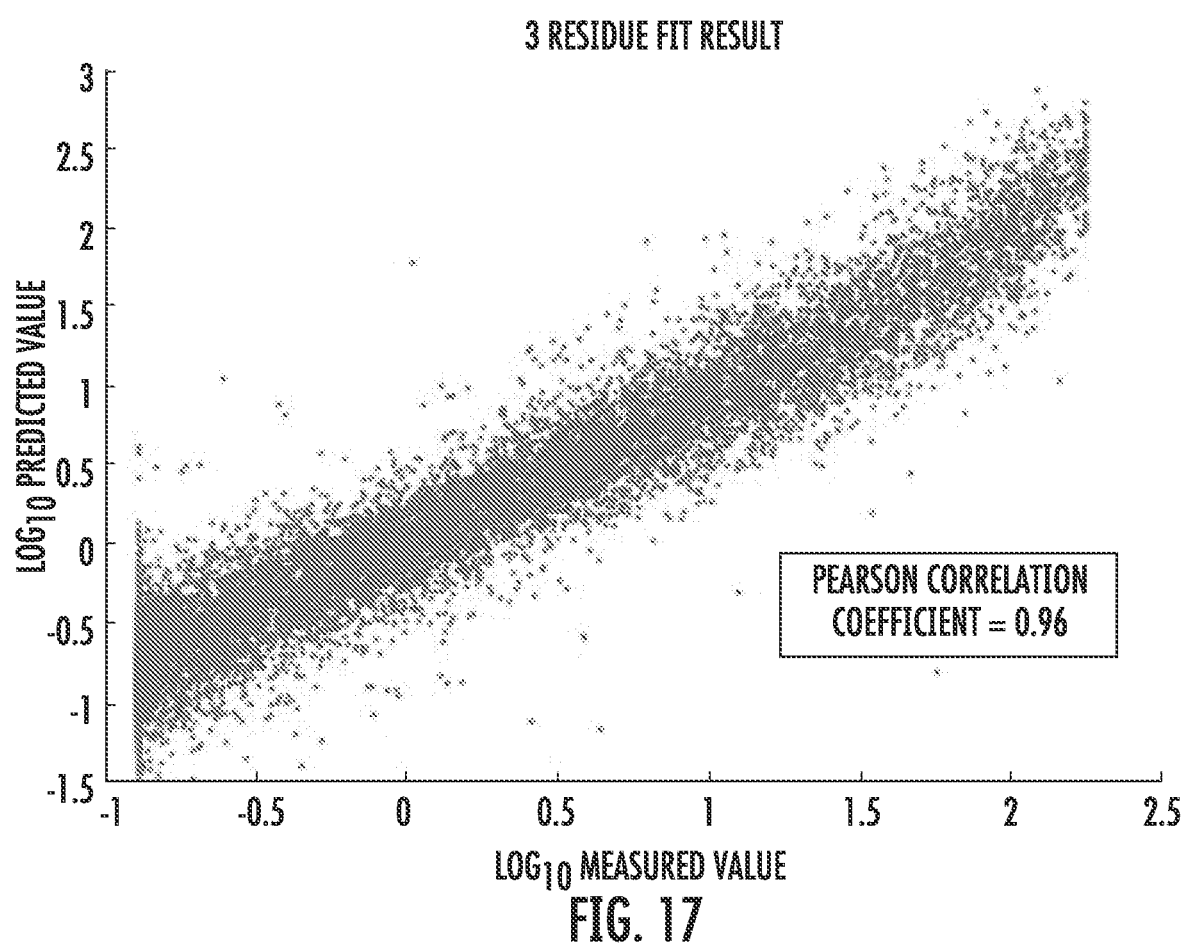
FIG. 17. Scatter plot of predicted vs. measured values from a fit using equation 4 of the log 10 of median normalized binding data from transferrin binding to a 330,000 peptide array. The predicted values are of sequences that were held out of the fit.
Figure 18:
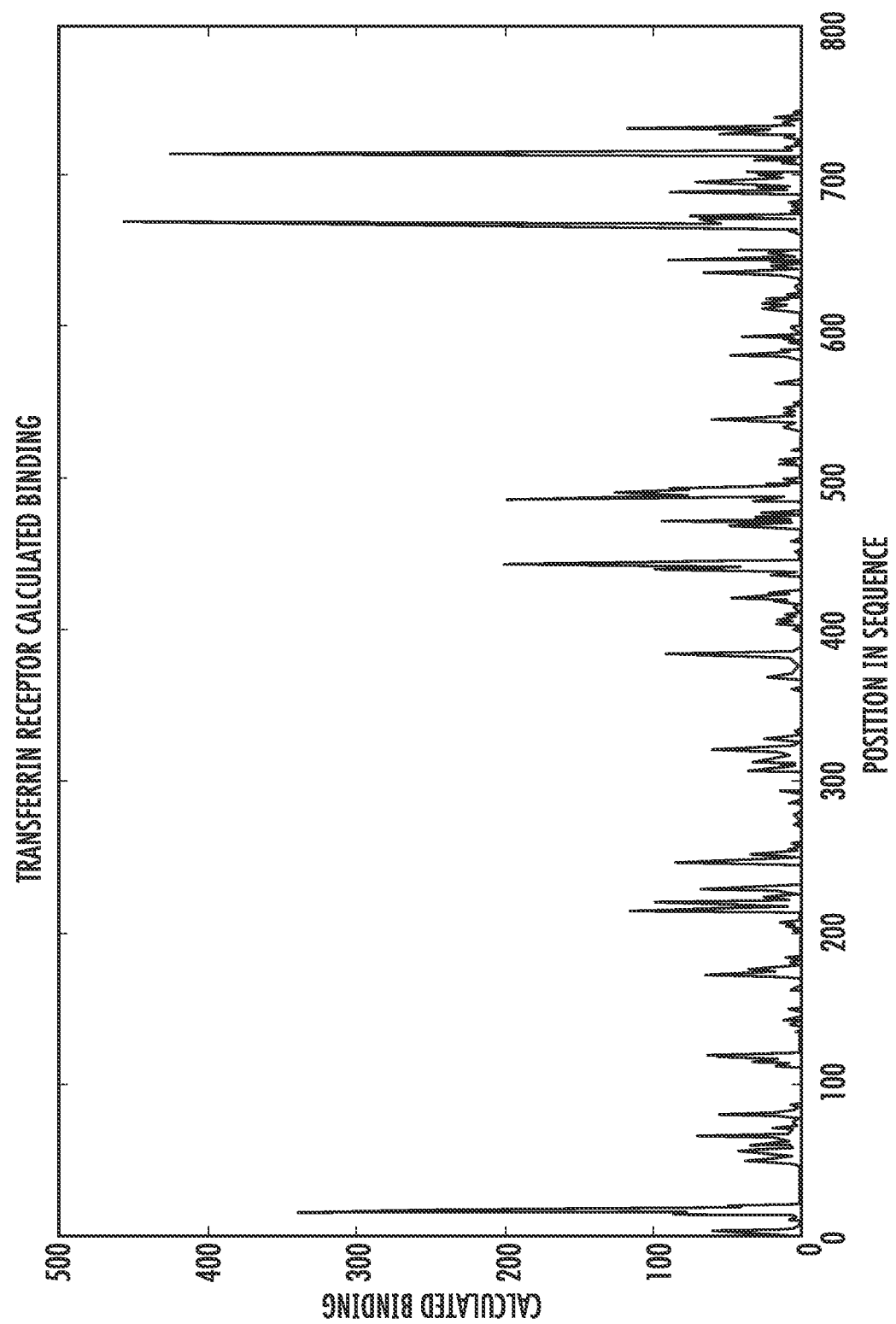
FIG. 18. Applications of the transferrin data fit to the prediction of binding to sequences that make up the transferrin receptor. The receptor sequence was broken into a set of overlapping 12 amino acid peptides and the equation was used to predict the binding to each of these peptides.

It is also Possible to use the peptide array to determine the range of sequences a protein binds to and then use that information to characterize the interaction with its partner. FIG. 17 shows a fit using equation 4 of the data from binding of transferrin to a peptide array containing about 330,000 sequences. The axes are the log of the median normalized measured values (x-axis) vs the log of the median normalized predicted values (y-axis). As with other examples, the points shown are true predictions in that those sequences were held out of the fits and their values predicted. The correlation coefficient between measured and predicted values is 0.96. Using the resulting equation from the fit, one can predict how transferrin might bind to the transferrin receptor (FIG. 18). This complex has been crystalized. As done in previous examples (see the tubulin monoclonal example), one can look at the initial binding prediction (FIG. 18) and then one can use what is known about specific binding to limit that prediction.

Figure 19:
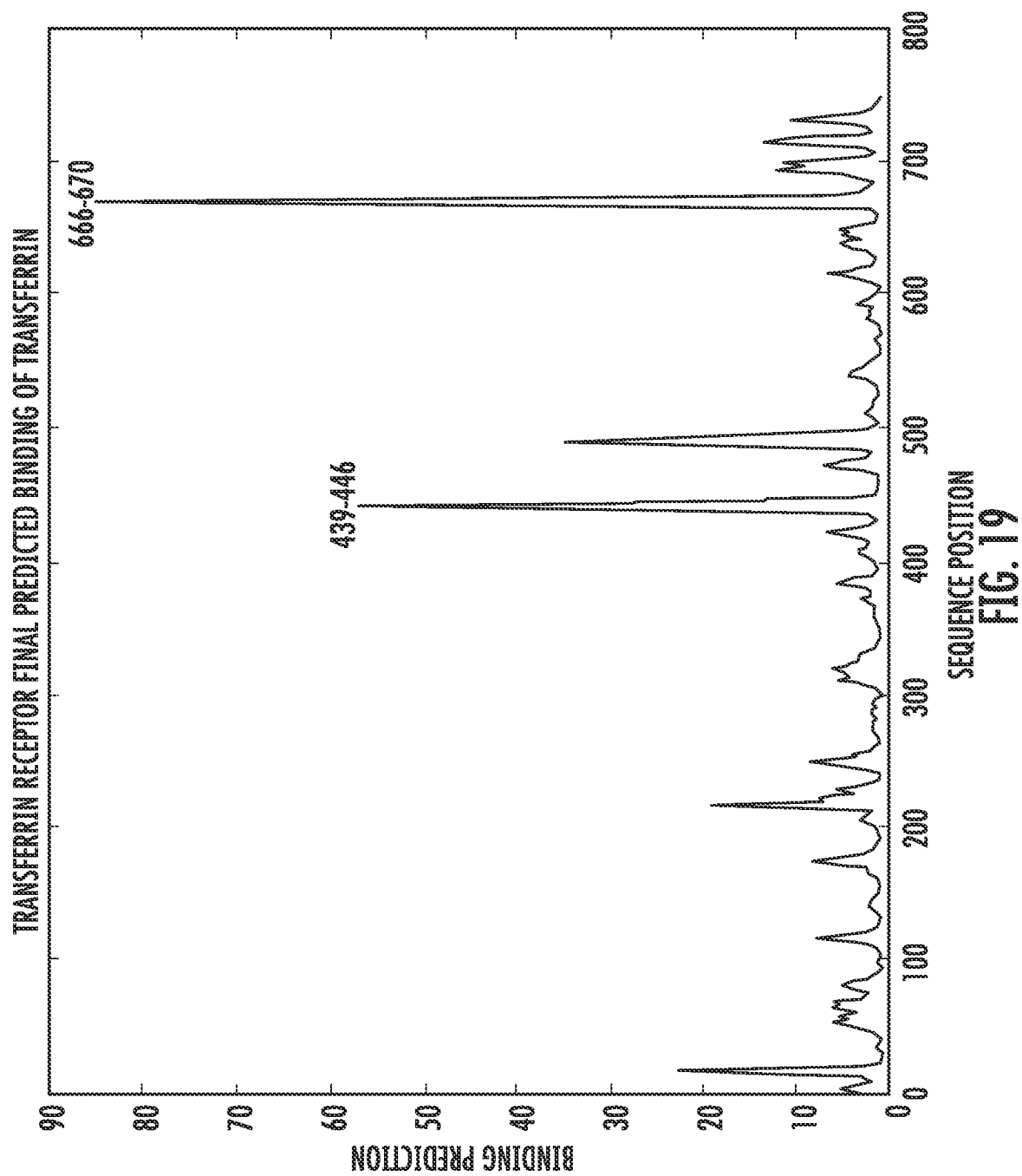
FIG. 19. Binding prediction for transferrin to the transferrin receptor after considering the fact that true specific binding sequences would persist in multiple sequence windows and be very sensitive to point mutation.
Figure 20:
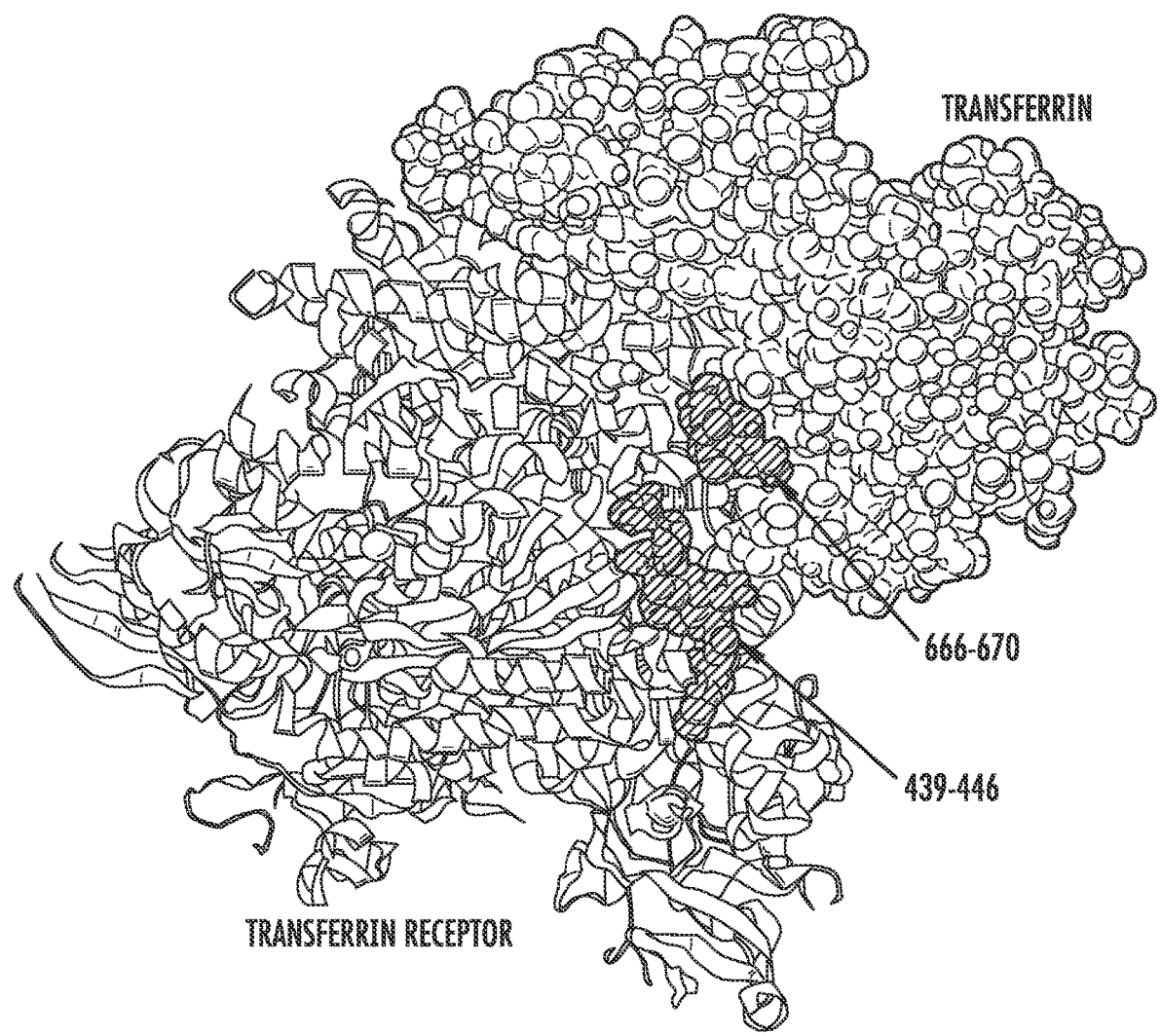
FIG. 20. Sequence in the transferrin receptor shown in red (darkest) represents the two top binding regions in FIG. 19. These are both at the interface between the receptor and transferrin.

In this case, as with tubulin, it was assumed that the binding would be substantial in multiple consecutive windows of the calculation and that it would be very sensitive to point mutants. With those two constraints the prediction of strongest binding regions includes two relatively prominent features, one of which covers residues 666-670 of the receptor and the other covers the residues 439-446 (FIG. 19). FIG. 20 shows that both of these sequences lie near the interface between transferrin and its receptor, suggesting that this approach has successfully pinpointed a portion of the binding region directly from an array analysis of one of the two partners.

Example 6: Computational Analysis to Predict Molecular Recognition Space of Monoclonal Antibodies Through Random-Sequence Peptide Arrays To characterize the monoclonal antibodies (mAbs) and identify their epitopes, a nonlinear model is solved using iterative linear fitting that correlates the binding of the mAbs to their structure. The fluorescence intensity value resulting from binding these mAbs to a peptide array is used as the prediction objective to train the model. Three mAbs (DM1A, 4C1 and p53Ab1) were used as a candidate dataset. Each dataset was segregated into two disparate groups to train the model and test its accuracy. The fit accuracy was measured using linear correlation.

For validation, the predicted model was analyzed by projecting the fit results from the peptide array onto the antigen and whole human proteome. The binding values were predicted for peptide sequences generated from the proteins and each mAb were mapped to their corresponding epitope. With a high correlation, the model successfully predicted the epitope of both DM1A and 4C1. The experimental finding also included the need for a more sophisticated model for p53Ab1.

Most approaches to relate the covalent structure of the molecule in libraries to their function lack the biological complexity and hence are deficient in important information. For example, the derivation of consensus motif in peptide libraries is done by simply assigning a weight to an individual amino acid in the sequence. However, many of the biological interactions cannot be described by such simple models and higher order interactions have to be taken into consideration. These higher order interactions, distributed in the structure, are information rich and thus their identification requires analysis of a large number interaction examples. To accomplish this goal, the algorithm proposed is based on the idea that binding of an antibody to a peptide sequence is a function of three components of the sequence: covalent structure of the peptide sequences, amino acids used in the peptide array and a description of properties of the amino acids that relate them to the function in question. A detailed description of the function is provided in detail below.

The algorithm was used to characterize the binding recognition space of three monoclonal antibodies (mAbs) with known linear epitopes (as shown in Table 2) and was subsequently projected onto entire human proteome for epitope mapping. A schematics of lithography-based peptide array synthesis is provided in FIG. 21.

Figure 21A:
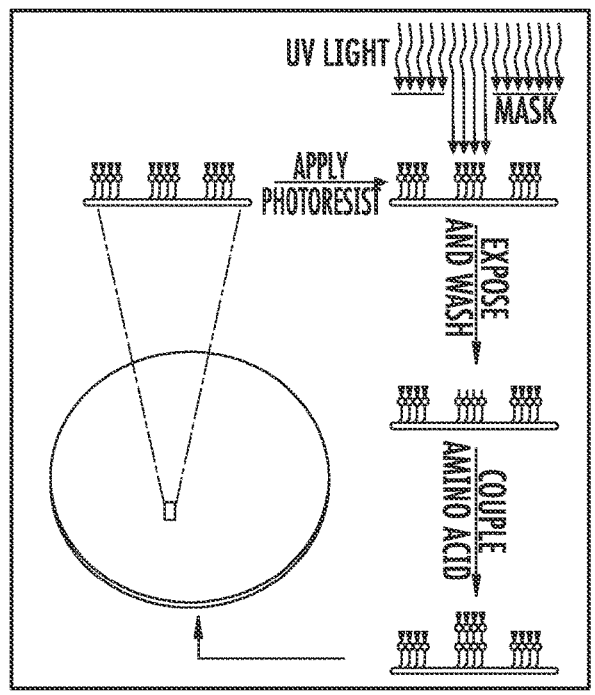
FIG. 21. Lithography-based peptide array synthesis. (a) Mask-based patterned synthesis of peptides on silicon wafers. (b) The wafer is diced into microscope slide sized regions, each of which contains 24 arrays. The rightmost is an image of the array of serum applied to the array and detected with fluorescent secondary antibody.
Figure 21B:
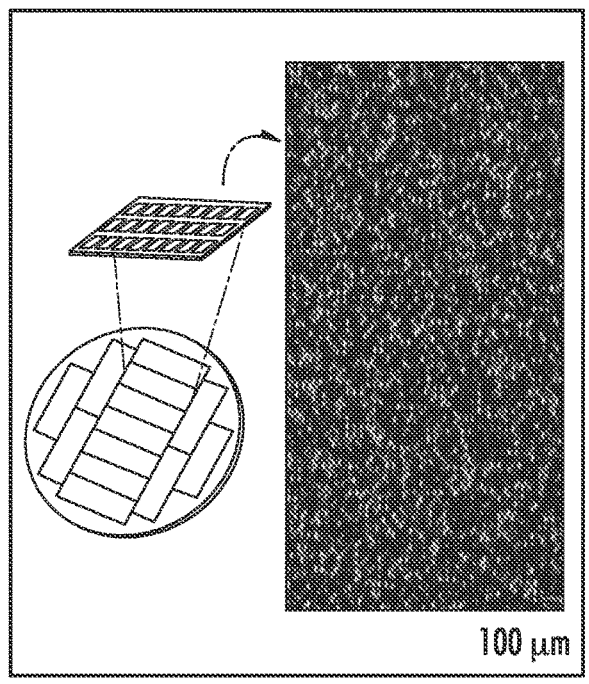

The fluorescence data sets used in this study were provided by HealthTell Inc. (Chandler, Ariz., USA). They fabricated arrays of ~127,000 peptides, averaging 9 amino acids in length using lithography-based peptide array synthesis. The schematic diagram of this procedure is shown in FIG. 21. To minimize the number of synthetic cycles, an algorithm was used to generate each peptide pseudo-randomly. 16 out of 20 natural amino acids (excluding cysteine, methionine, isoleucine and, threonine) were used to generate the peptide sequences. They bound the fluorescently labeled mAbs to the arrays using assays which are standard in the company. The arrays were washed and dried to get rid of excess mAbs and were later imaged on a commercial imaging system. The images were then processed to provide a quantitative value of fluorescence intensity for each peptide on the array.

Three mAbs were used in the analysis: DM1A (anti-human alpha tubulin), 4C1 (anti-human TSHR) and p53Ab1 (anti-human TP53). The list of the immunogen, isotype and epitope of each mAb is tabulated in Table 2.

TABLE 2

The monoclonal antibodies used for the characterization

| Antibody | Immonogen | Isotype | Epitope |
|---|---|---|---|
| DM1A | Human α tubulin | IgG1$_\kappa$ | ALEKDY SEQ ID NO. 5 |
| 4C1 | Human TSH receptor | IgG2a | QAFDSH SEQ ID NO. 3 |
| p53Ab1 | Human p53 | IgG1 | RHSVV SEQ ID NO. 6 |

On an abstract level, the relation between the molecular recognition of an antibody and peptide sequence on the array is represented mathematically by Equation A as stated below—

$$B = f(s)$$ Equation A where B is the molecular recognition represented by fluorescence binding and $f(s)$ is a function of the peptide sequence. The composition of the function is based on three components: (a) covalent structure of the peptide sequences, (b) amino acids used in the peptide array and (c) description of properties of the amino acids. Mathematically, this can be expressed as:

$$f_{n(sequence)} = \sum_m \sum_r \sum_k C_{n,m,r} Q_{k,m} A_{k,r} \quad \text{Equation B}$$

In the above equation, $f_{n(sequence)}$ is the function of the $n^{th}$ peptide on the array. $C_{n,m,r}$ is the description of the covalent structure of the peptide. Here, 'n' is the specific peptide, 'm' represents chemical entities formed by groupings of particular amino acids and 'r' represents the structural arrangements of these chemical entities in terms of the physical position of the amino acids in the peptide. This is constructed from the input peptide sequence and portrays quantitative information of the same in terms of basis set of the structural and chemical components. 'm' could be individual amino acid or pairs of amino acids or sets of three amino acids. $Q_{k,m}$ represents the assignment of properties to the chemical entities, 'k' being the number of properties assigned to each of the 'm' chemical entities. $A_{k,r}$ represents the weighting coefficients assigned to the different functional components of the peptide in terms of their properties. This function is the foundation of the algorithmic model developed to predict the binding values of an input sequence. It is also to be noted that $Q_{k,m}$ and $A_{k,r}$ are free variables in the function. The accurate computation of these free variables guides the efficacy of the algorithmic model in terms of its predictive accuracy.

An example is used to explain the mathematical equation B. Consider a scenario in which peptide sequences are described in terms of groups of 3 amino acids. There are 4096 combinations of 3 amino acids possible (16 amino acids were used in the peptide array synthesis, hence $16^3=4096$). Therefore, the index 'm' would range from 1 to 4096. For a model that uses 9 amino acids long peptide, 'r' could be all possible ways of placing three amino acids into a 9 length peptide which is essentially $$\binom{9}{3} = 84$$

and hence 'r' would range from 1 to 84. If there were 4 properties ('k') assigned to each of the 'm' entities, then the total number of free variables in the fit would be given by the number of elements in Q (4×4096) and A (4×84).

Equation B was used to fit the fluorescent data resulting from binding of the mAbs to the peptide array. MATLAB software was used for all the computations. As mentioned in the previous section, $C_{n,m,r}$ is computed from the input peptide sequences and is fixed in the function with two free variables $Q_{k,m}$ and $A_{k,r}$. As the function is composed of two variables, it introduces non linearity and makes optimization computationally difficult. To solve this, firstly the non-linearity of the function was reduced to linear equation by assigning normally distributed random numbers around zero for $Q_{k,m}$ in the beginning and holding it constant. This reduced the equation to a simple linear equation of the form y=cx, where 'c' is a constant (here $c=C_{n,m,r} \times Q_{k,m}$) and 'x' is the free variable ($A_{k,r}$). The equation was then solved to calculate $A_{k,r}$. The value of $A_{k,r}$ was then used to calculate $Q_{k,m}$ by making it a free variable. This process of computing one free variable by making another fixed was iterated until a convergence was reached. This iterative approach to fit $A_{k,r}$ and $Q_{k,m}$ linearly was optimized by least square method. Briefly, in least square optimization the objective is to find a solution for a free variable 'x' where the sum $\Sigma_{i=1}^{n}(y_i - cx_i)^2$ is minimized i.e. to be close to zero. The primary goal of using least square optimization is to find a solution for the variable that best fits the data points.

In this analysis, a combination of 3 amino acids were used and each peptide was set to be 9 amino acids long. For each of the chemical entities number of propertied assigned was set to 4. The data was then segregated into two disparate sets. 90% of the data was used to train the algorithm and the rest 10% was used to test the predictions. This is a well-known technique applied in machine learning to validate the accuracy of the fitting model. Before fitting, the binding values were median normalized. The result from the fit was viewed in a scatter plot with predicted binding values from the fit on y-axis and measure binding values from the array on x-axis. The fit accuracy between predicted and measured binding was evaluated by linear correlation measurement.

In order to map the epitope of a mAb, the fitting response was projected onto its antigen and then onto the whole human proteome. The antigen protein sequence and the entire human proteome was obtained from UniProt database. For human proteome, the total number of proteins are ~20,000. Each protein was broken down computationally into sequences of 9 amino acids long which generated ~11,000,000 sequences. For each of these sequences, a binding value was predicted. In order to see whether the epitope depends on the order of amino acids and not just the composition when compared to other non-cognate sequences each of these sequences were scrambled randomly into 200 possible ways and their average binding values were calculated. Based on the ratio of the binding value of the original sequence (when it was not scrambled) and the average binding value of the 200 scrambled sequences an attempt was made to evaluate the biological constraint of an epitope.

Computational analyses were done to evaluate the molecular recognition profile of mAbs for all possible peptide sequences using their binding values on the peptide array. The predictions made by fitting the binding data to Equation B were true predictions as the overall binding data was segregated into two disjoint sets. The first dataset (training data) was used to train the prediction model which was applied to the second dataset (testing data) to predict binding. Additionally, to better investigate the efficacy of the model, the epitope sequences were excluded from the training set.

Figure 22:
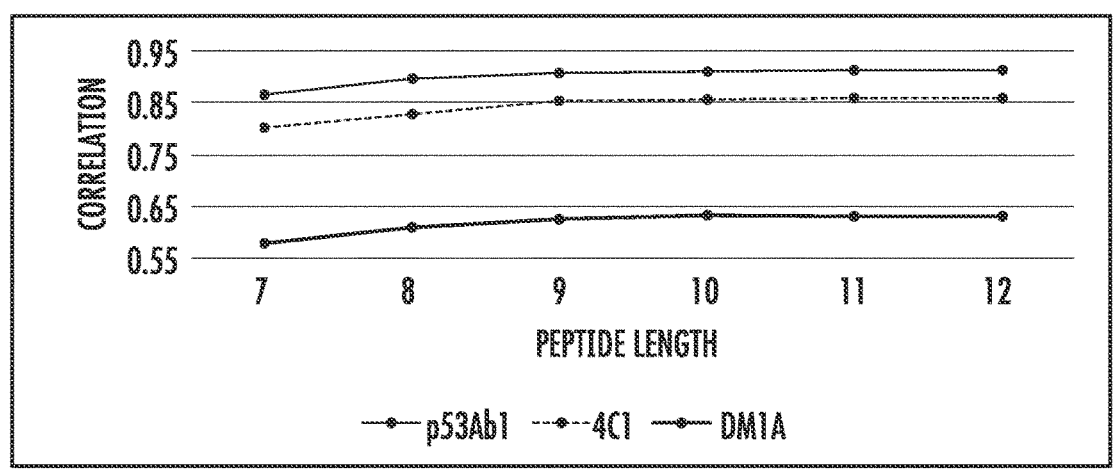
FIG. 22. Change in correlation with increase in length of peptide for different datasets.

It is to be noted that the length of the peptides used in the fitting was chosen to be 9. This is because the correlation between predicted and measured binding saturated after 9 amino acids long peptides. FIG. 22 shows that for all the mAbs used, the correlation increases when the length of peptides were increased from 7 to 9 and saturates for higher lengths. Thus, all the analysis was done with peptides having 9 amino acids. This correlation was calculated for log transformed data.

Figure 23:
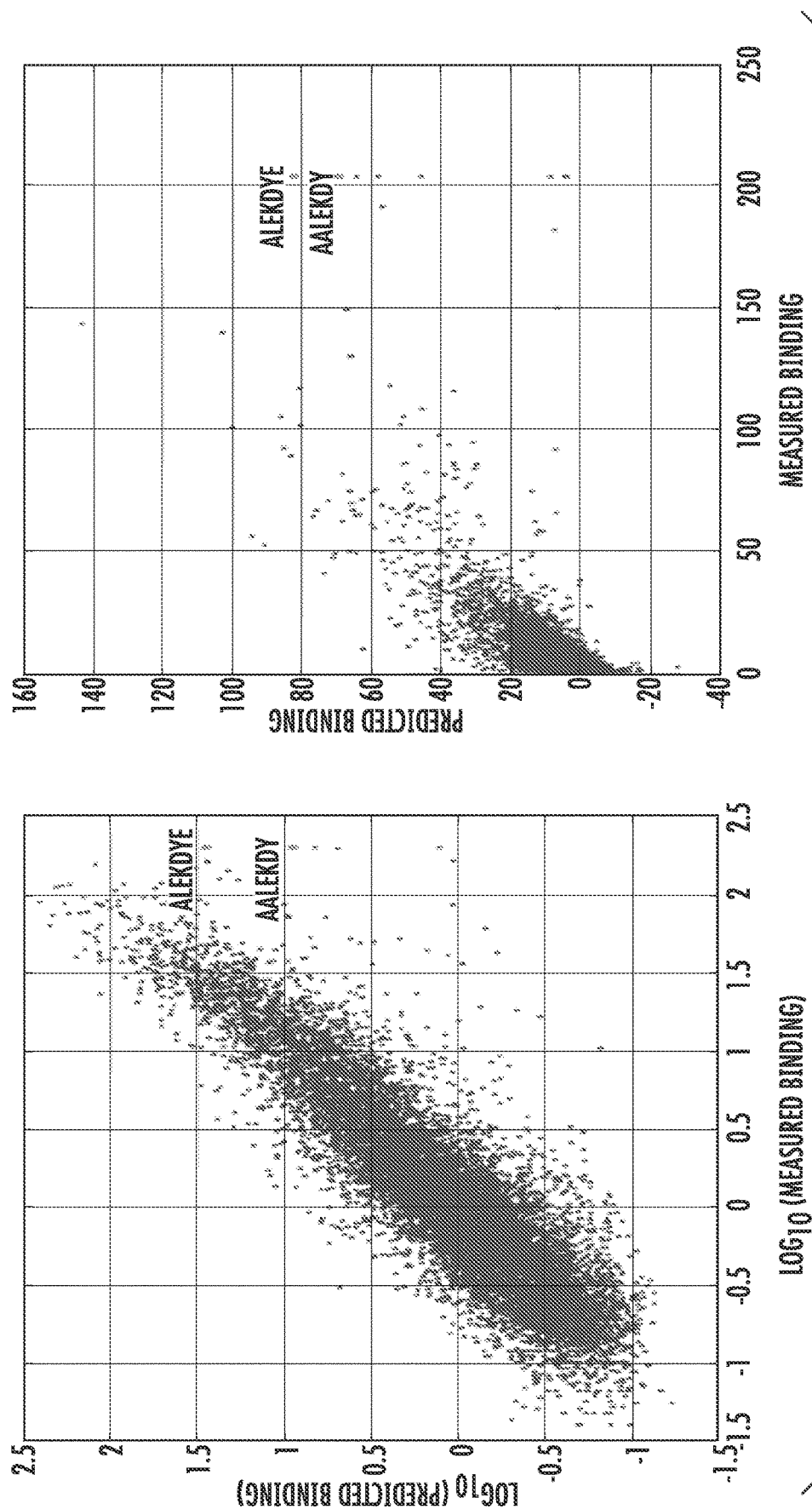
FIG. 23. Scatter plot showing measured and predicted binding for mAb DM1A using (a) log transformed data (correlation=0.907) and (b) linear data (correlation=0.747).
Figure 24:
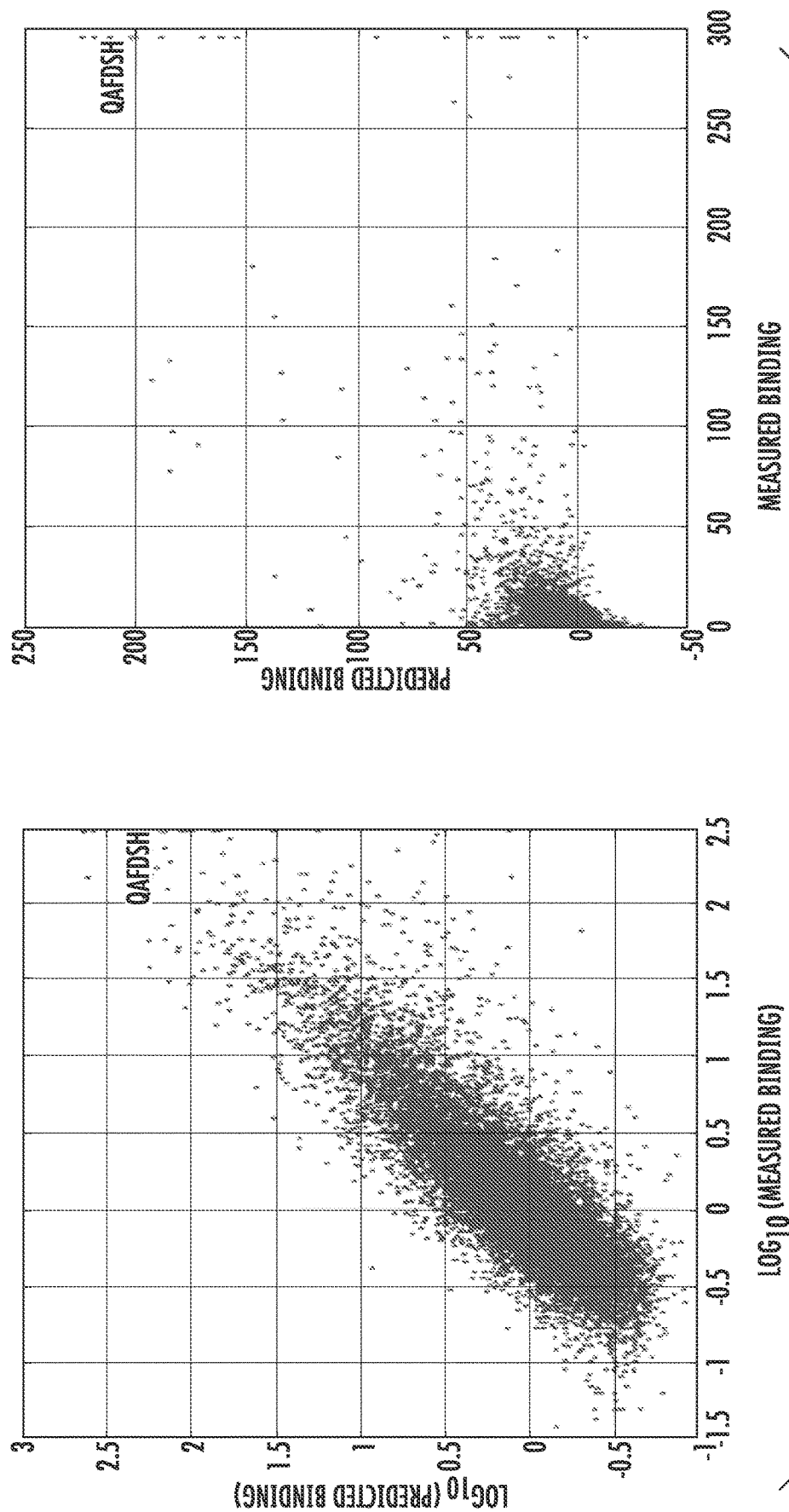
FIG. 24. Scatter plot showing measured and predicted binding for mAb 4C1 using (a) log transformed data (correlation=0.849) and (b) linear data (correlation=0.614).
Figure 25:
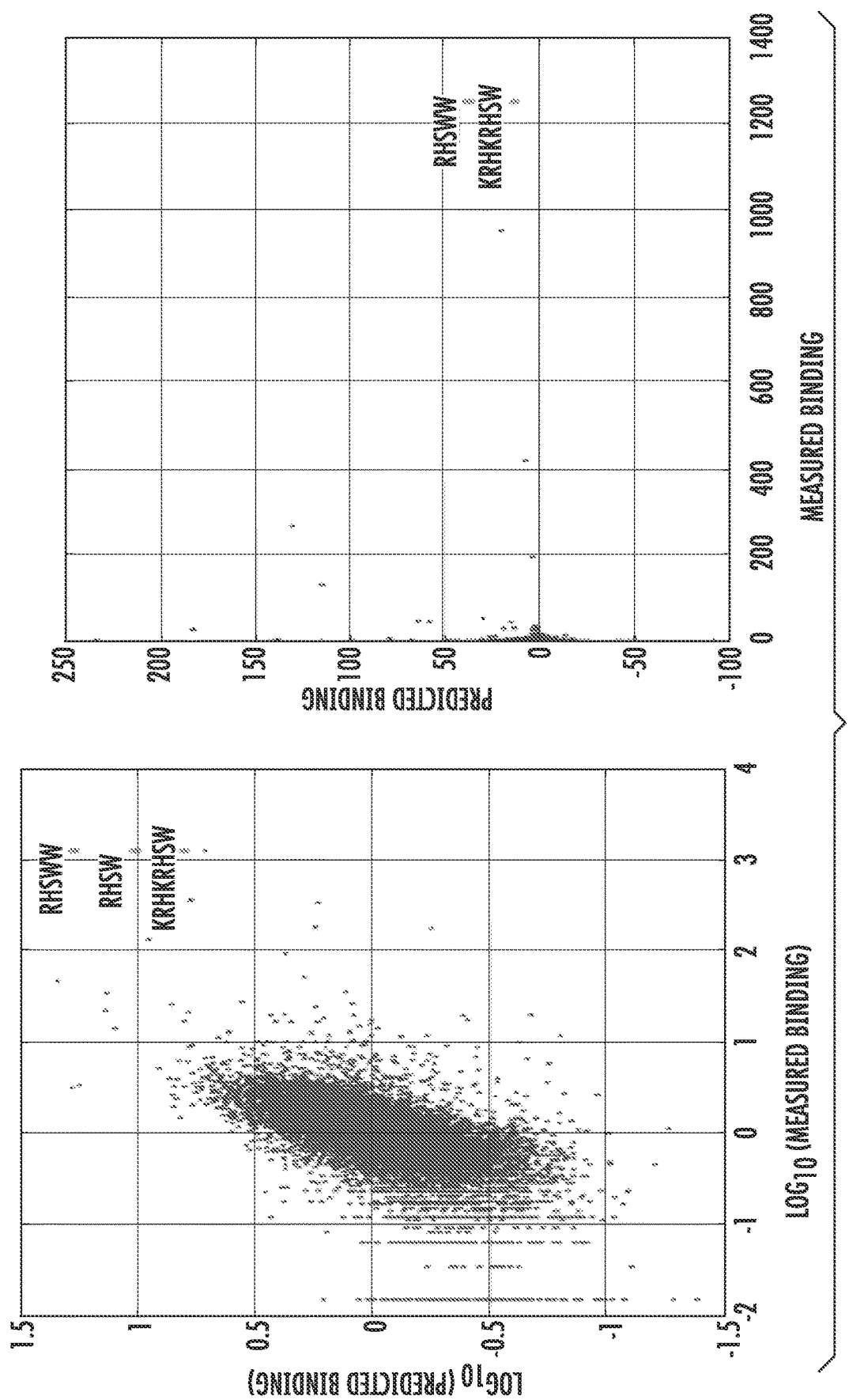
FIG. 25. Scatter plot showing measured and predicted binding for mAb p53Ab1 using (a) log transformed data (correlation=0.621) and (b) linear data (correlation=0.131).

To enhance the linearity of the fitting between predicted and measured binding, the data was transformed into $\log_{10}$ scale prior to the fitting. Transformation of the data bolstered the model accuracy. FIGS. 23-25 is used to support this assertion. It can be seen from the scatter plots in FIGS. 23-25 that the predicted binding with the untransformed data reflected a significant number of low binding peptides that resulted in a lower correlation. However, it displayed the For mAb DM1A (FIG. 23), the fitting resulted in the highest correlation among all the three mAbs used. The epitope (ALEKDY)(SEQ ID NO. 5) was predicted to be one of the top binding sequences. Likewise, the algorithm successfully determined the epitope (QAFDSH) (SEQ ID NO. 3) for mAb 4C1 (FIG. 24). Interestingly, the prediction of epitope was better for 4C1 than that of DM1A. In case of the third and a highly specific mAb p53Ab1, the correlation was poor (FIG. 25). This is because majority of the peptide sequences on the array had a very low fluorescence binding. Despite such a low correlation, the predicted binding of the epitope was significantly strong.

Having demonstrated that the algorithm is capable of resolving epitopes of mAbs, further analyses was performed to assess the predictive ability of the same when the fitting response was mapped onto the other proteins. To emphasize high binders, the untransformed fit (without $\log_{10}$ transformation) from the binding was used for mapping onto other proteins.

Figure 26A:
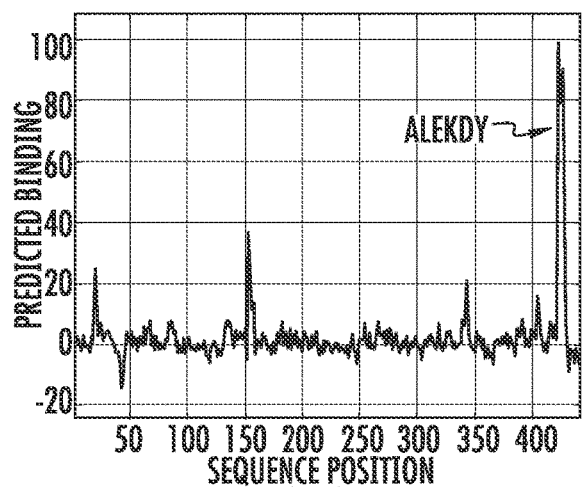
FIG. 26. Predicted binding of (a) human alpha tubulin protein using DM1A fit, (b) human TSH protein using 4C1 fit, (c) human TP53 protein using p53Ab1 fit. The sequences shown are the cognate sequences of the respective antibodies.
Figure 26B:
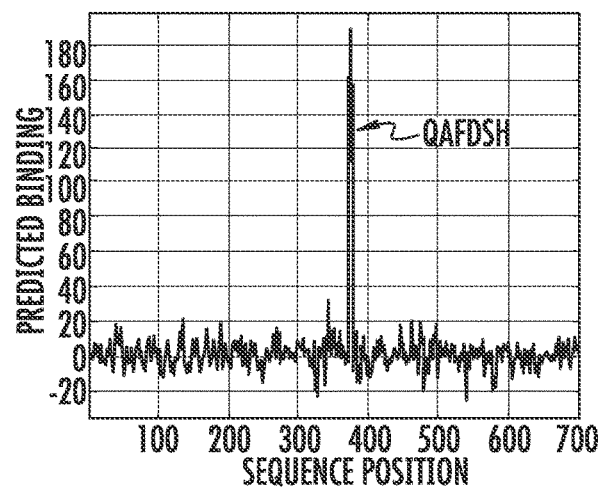
Figure 26C:
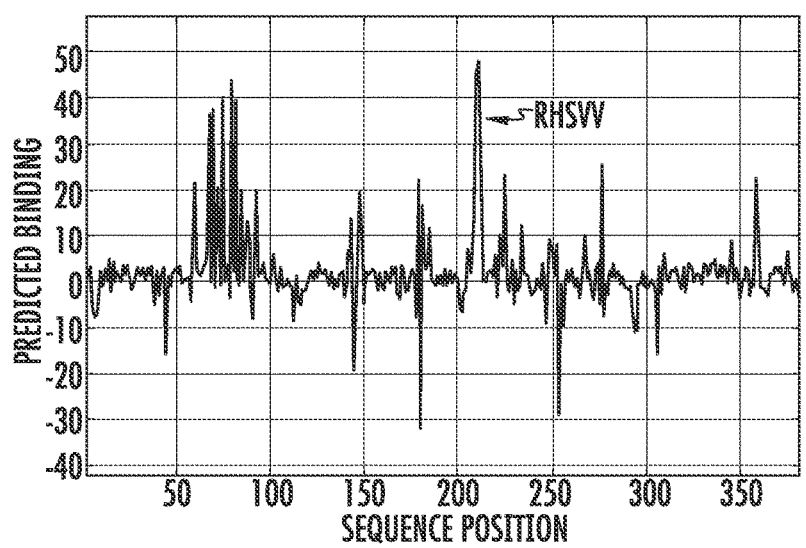

The binding fit response of each antibody was projected onto the antigen to map the epitope it interacts with. FIGS. 26(*a*)-(*c*) shows the map of each mAb towards their antigen using the untransformed fit for DM1A, 4C1 and p53Ab1 respectively. For both DM1A and 4C1, the prominent binder predicted was their epitopes ALEKDY (SEQ ID NO. 5) and QAFDSH (SEQ ID NO. 3) respectively. In case of p53Ab1, the epitope RHS (SEQ ID NO. 6) was indeed the topmost predicted binder but there were other sequences too that were predicted to be very close in binding to the epitope. Such a result is expected since the correlation of p53Ab1 from the fit was just 0.131 for the untransformed fit.

The next goal was to map the fit response onto the whole human proteome to identify the antigen of a specific antibody from a list of ~20,000 proteins. In order to assess both specific and non-specific interaction to other human proteins, the binding pattern of mAbs was analyzed using proteome-wide mapping. The binding distribution of DM1A revealed that the predicted binding of epitope is much higher than the vast majority of sequences, but not at the top. Table 3 lists the potential antigens that were predicted. A lot of the top binders with repetitive residues looked

TABLE 3

Predicted binding of the sequence with decreasing binding values generated from the proteins in human proteome using DM1A fit (human alpha tubulin is the 119$^{th}$ protein in the list)

| Position | Sequence | Predicted Binding | Protein in Human proteome |
|---|---|---|---|
| 1 | WWEDLERDF (SEQ ID NO. 7) | 189.647 | sp\|Q9HCM9\|TRI39_HUMAN E3 ubiquitin-protein ligase TRIM39 OS = Homo sapiens GN = TRIM39 PE = 1 |
| 2 | PWWDDWERD (SEQ ID NO. 8) | 151.524 | sp\|P49750\|YLPM1_HUMAN YLP motif-containing protein 1 OS = Homo sapiens GN = YLPM1 PE = 1 SV = 3 |
| 3 | WSDDFDSDY (SEQ ID NO. 9) | 148.651 | sp\|Q8WV28\|BLNK_HUMAN B-cell linker protein OS = Homo sapiens GN = BLNK PE = 1 SV = 2 |
| 4 | WWEDEWEVP (SEQ ID NO. 10) | 146.713 | sp\|P06239\|LCK_HUMAN Tyrosine-protein kinase Lck OS = Homo sapiens GN = LCK PE = 1 SV = 6 |
| 5 | SVFELDYDY (SEQ ID NO. 11) | 139.905 | sp\|Q6AI14\|SL9A4_HUMAN Sodium/hydrogen exchanger 4 OS = Homo sapiens GN = SLC9A4 |
| 117 | VYELLEKDY (SEQ ID NO. 12) | 99.156 | sp\|P00519\|ABL1_HUMAN Tyrosine-protein kinase ABL1 OS = Homo sapiens GN = ABL1 PE = 1 SV = 4 |
| 118 | QFEELEVDY (SEQ ID NO. 13) | 98.99 | sp\|Q8TD16\|BICD2_HUMAN Protein bicaudal D homolog 2 OS = Homo sapiens GN = BICD2 PE = 1 |
| 119 | DLAALEKDY (SEQ ID NO. 14) | 98.915 | sp\|Q13748\|TBA3C_HUMAN Tubulin alpha-3C/D chain OS = Homo sapiens GN = TUBA3C PE = 1 | like non-specific interactions. Human alpha tubulin (ALEKDY) (SEQ ID NO. 5) was the 119th protein out of ~20,000 proteins when looking at the predicted binding values from higher to lower.

TABLE 4

Predicted binding of the sequence with decreasing binding values generated from the proteins in human proteome using 4C1 fit (human TSH is the 244th protein in the list)

| Position | Sequence | Predicted Binding | Protein in Human proteome |
|---|---|---|---|
| 1 | VGSYDSFDT (SEQ ID NO. 15) | 394.45 | sp\|Q9UPX8\|SHAN2_HUMAN SH3 and multiple ankyrin repeat domains protein 2 OS = Homo sapiens GN = SHANK2 PE = 1 SV = 3 |
| 2 | FDSWFDTNN (SEQ ID NO. 16) | 385.833 | sp\|O60264\|SMCA5_HUMAN SWI/SNF-related matrix-associated actin-dependent regulator of chromatin subfamily A member 5 OS = Homo sapiens GN = SMARCA5 PE = 1 SV = 1 |
| 3 | VPSYDSFDS (SEQ ID NO. 17) | 380.779 | sp\|P14921\|ETS1_HUMAN Protein C-ets-1 OS = Homo sapiens GN = ETS1 PE = 1 SV = 1 |
| 4 | YDSFDTFIR (SEQ ID NO. 18) | 379.841 | sp\|Q9C0G6\|DYH6_HUMAN Dynein heavy chain 6, axonemal OS = Homo sapiens GN = DNAH6 PE = 2 SV = 3 |
| 5 | FDSFDTTGT (SEQ ID NO. 19) | 374.538 | sp\|Q8N4C6\|NIN_HUMAN Ninein OS = Homo sapiens GN = NIN PE = 1 SV = 4 |
| 242 | QPQHFDSFG (SEQ ID NO. 20) | 230.319 | sp\|Q9P215\|POGK_HUMAN Pogo transposable element with KRAB domain OS = Homo sapiens GN = POGK PE = 1 SV = 2 |
| 243 | PPAAYDSSH (SEQ ID NO. 21) | 230.318 | sp\|P55017\|S12A3_HUMAN Solute carrier family 12 member 3 OS = Homo sapiens GN = SLC12A3 PE = 1 SV = 3 |
| 244 | SLQAFDSHY (SEQ ID NO. 22) | 230.314 | sp\|P16473\|TSHR_HUMAN Thyrotropin receptor OS = Homo sapiens GN = TSHR PE = 1 SV = 2 |

TABLE 5

Predicted binding of the sequence with decreasing binding values generated from the proteins in human proteome using p53Ab1 fit (human TP53 is the 14023rd protein in the list). Similar results were obtained for the mAb 4C1 (Table 4), where the human TSH protein (QAFDSH) (SEQ ID NO. 3) was at 244th position. In case of p53Ab1, the predictions displayed an extensive amount of off-target binding. The number of unique proteins above the human TP53 protein (RHSVV) (SEQ ID NO. 6) were 14,023 as shown in Table 5.

| Position | Sequence | Predicted Binding | Protein in Human proteome |
|---|---|---|---|
| 1 | ERDSMLLQQ (SEQ ID NO. 23) | 1850.433 | sp\|Q9P2E2\|KIF17_HUMAN Kinesin-like protein KIF17 OS = Homo sapiens GN = KIF17 PE = 2 SV = 3 |
| 2 | EIHLLLLQQ (SEQ ID NO. 24) | 1850.000 | sp\|Q16832\|DDR2_HUMAN Discoidin domain-containing receptor 2 OS = Homo sapiens GN = DDR2 PE = 1 SV = 2 |
| 3 | IDSHMLLQQ (SEQ ID NO. 25) | 1849.901 | sp\|Q96DT5\|DYH11_HUMAN Dynein heavy chain 11, axonemal OS = Homo sapiens GN = DNAH11 PE = 1 SV = 4 |
| 4 | GASLLLLQQ (SEQ ID NO. 26) | 1848.207 | sp\|P10275\|ANDR_HUMAN Androgen receptor OS = Homo sapiens GN = AR PE = 1 SV = 3 |
| 5 | SIVTLLLQQ (SEQ ID NO. 27) | 1848.154 | sp\|Q8IVF6\|AN18A_HUMAN Ankyrin repeat domain-containing protein 18A OS = Homo sapiens GN = ANKRD18A |
| 14021 | AAFDFLLQR (SEQ ID NO. 28) | 47.705 | sp\|Q07864\|DPOE1_HUMAN DNA polymerase epsilon catalytic subunit A OS = Homo sapiens GN = POLE PE = 1 SV = 5 |

TABLE 5-continued

Predicted binding of the sequence with decreasing binding values generated from the proteins in human proteome using p53Ab1 fit (human TP53 is the 14023$^{rd}$ protein in the list). Similar results were obtained for the mAb 4C1 (Table 4), where the human TSH protein (QAFDSH) (SEQ ID NO. 3) was at 244$^{th}$ position. In case of p53Ab1, the predictions displayed an extensive amount of off-target binding. The number of unique proteins above the human TP53 protein (RHSVV) (SEQ ID NO. 6) were 14,023 as shown in Table 5.

| Position | Sequence | Predicted Binding | Protein in Human proteome |
|---|---|---|---|
| 14022 | HHRSILLAS (SEQ ID NO. 29) | 47.699 | sp\|O95343\|SIX3_HUMAN Homeobox protein SIX3 OS = Homo sapiens GN = SIX3 PE = 1 SV = 1 |
| 14023 | FRHSVVVPY (SEQ ID NO. 30) | 47.699 | sp\|P04637\|P53_HUMAN Cellular tumor antigen p53 OS = Homo sapiens GN = TP53 PE = 1 SV = 4 |

Additionally, computational analysis was done to incorporate biological constraint on the system. As mentioned in Section 2.4, an epitope depends on the order of amino acids in its sequence and not just the composition. If the order is changed, its behavior would change. A similar observation was obtained from the analysis. When the cognate sequences were scrambled, the predicted binding values reduced extensively for the scrambled sequences. Taking the ratio of the binding value of the original sequence and average binding values of scrambled sequences allowed the epitope to move to the top. The result of this analysis is

TABLE 6

Positioning of the protein after scrambling the order of amino acids in the sequences.

| Protein | Position before scrambling | Position after scrambling |
|---|---|---|
| Alpha tubulin (ALEKDY) (SEQ ID NO. 5) | 119 | 12 |
| TSH protein (QAFDSH) (SEQ ID NO. 3) | 244 | 72 |
| TP53 protein (RHSVV) (SEQ ID NO. 6) | 14023 | 1348 | summarized in Table 6.

As discussed above, a monoclonal antibody might bind strongly to sequences far from its ideal epitope. Thus, in order to explore the molecular recognition space of an antibody, a platform was developed that could capture sequence information of a given peptide on the array in terms of its structural and chemical components. The first step in this regard was to see whether the algorithm could use the sequence information to resolve the cognate sequences for three well-characterized mAbs (Table 2). The mathematical formulation (Equation B) was able to reasonably predict the binding of epitope sequences of the mAbs.

To evaluate the predictive ability of the algorithm for a unique set of peptide sequences that were not used in the fit, a linear correlation between predicted and measured binding was calculated. For DM1A and 4C1, the predictions were very accurate as can be seen from the high correlation values of 0.907 and 0.849 respectively. For p53Ab1, the large number of weak binding peptide sequences contributed to its low correlation of 0.620. However, the predicted binding of its epitope RHSVV (SEQ ID NO. 6) was higher than most sequences, revealing the high specificity of this mAb towards its epitope. It was also seen that the correlation for each of the mAbs saturated after 9 residue length of peptide which is justified by the fact that the average length of the peptides on the array was 9. Decreasing the length from 9 resulted in a loss of information, which lowered the correlation.

When mapped onto the antigen protein, each of the mAbs identified their epitopes quite prominently with highest predicted binding. Projection onto the human proteome revealed that a lot of top binders were repeated sequence which can occur due to non-specific interactions. For both DM1A and 4C1, the predicted binding to their respective antigen human alpha tubulin (ALEKDY) (SEQ ID NO. 5) and human TSH protein (QAFDSH) (SEQ ID NO. 3) was higher than the majority of the proteins in the human proteome. But for p53Ab1, the result was not very accurate. This is expected because of the poor fitting correlation. An attempt was also made to see how sensitive a sequence is to alterations in its structural components. The analysis revealed that the cognate sequences not only depend on their structural composition but also on the specific order of the amino acids.

Example 7: Comprehensive Peptide-Protein Binding Prediction Using Machine Learning Alternative neural network implementations for relating amino acid sequence to its molecular recognition properties have been proposed recently by others. The success of machine learning in this realm opens the door for using machine learning to accurately predict molecular recognition from structure in the huge combinatorial sequence space of polypeptides and related heteropolymers more generally.

In this example, machine learning is used to model the binding of all possible peptide sequences about 10 residues in length to a specific target protein. This learned mapping between sequence and binding covers peptides with lengths in the range from about 7 to 12 residues that are made from 16 of the natural amino acids (A, D, E, F, G, H, K, L, N, P, Q, R, S, V, W, and Y). There are >$10^{12}$ possible sequences in this chemical space. The machine learning is trained on a nearly random set of ~$10^5$ of these sequences synthesized in individual positions on a peptide array. A purified target protein is fluorescently labeled and incubated with the array, resulting in a relative binding value for each peptide sequence. The primary question posed in this work is, how well can a machine learning algorithm use a sparse sampling (1 in $10^7$) of peptide/target interactions to represent the binding of all possible $10^{12}$ sequences with that target? In other words, embodiments herein are directed to using a very sparse set of structures and data to represent a very large set of possibilities. Thus, for example, methods and systems described herein may utilize a total possible number of combinations of the components used to create the chemical library in question that is equal to or greater than 100, 1000, 10000, 100000, 1000000, 10000000, 100000000, 1000000000, 10000000000, 100000000000, 1000000000000 fold larger than the number of molecules in the library for which structures have been physically synthesized, and functional properties are measured as inputs into a given algorithm.

Methods

Protein Binding Measurements.

Nine different proteins were fluorescently labeled and incubated with one of two different peptide array formats, washed and scanned (listed in FIG. 27B, details in associated text). The array consisted of either ~126,000 or about ~123,000 unique peptide sequences, synthesized directly on a silica coating on a silicon wafer and cut into microscope slide sized pieces, each slide with 24 arrays. Arrays were either synthesized at in the ASU peptide array core (biodesign.asu.edu/peptide-microarray-facility) and assays done there or synthesized by HealthTell, Inc. (healthtell.com/) and assays performed there. For each protein, data from 2-3 replicates was averaged. The values used in the neural network-based fits were $\log_{10}$ (counts+100), where "counts" are the unnormalized fluorescent counts recorded by the scanners. 100 was added to each value both to avoid taking the log of zero and to suppress large fluctuations due to noise (the noise level is a few hundred counts in these assays and the dynamic range is typically 100-200 fold above noise). Note that all correlations reported are between data on log scales.

Machine Learning.

A simple neural network was used to model the binding interactions between the peptides on the array and their target. Each peptide sequence was represented as a sparse matrix of zeros and ones, and this was multiplied with an encoder matrix that transforms each amino acid into a dense continuous representation (a real-valued vector). A feedforward neural network using two hidden layers each with 100 filters (columns or nodes) was then used to predict the target binding value for each peptide sequence.

Neural Network Training and Validation.

Neural networks were created and optimized in PyTorch 0.4. From the ~125,000 sequences and measured binding values, 90% of the data was used to train the network and 10% was set aside to validate the trained model's performance unless stated otherwise. To avoid fitting the model to saturated data points (where the binding intensity exceeded the maximum measurable level of the detector) the top ~2% of the data was excluded from the training set (but included in the validation set). The peptide arrays are generally synthesized in such a way that they have a GSG amino acid linker at the C-terminal end. This was removed from all sequences prior to analysis. Peptide binding was fit to $\log_{10}$ (counts+100), where "counts" is the raw fluorescence counts recorded by the fluorescence array scanner and 100 was added to suppress large fluctuations in the log due to noise and to avoid taking the log of zero. The distribution of binding strengths on a log scale is much closer to normal than on a linear scale, facilitating the fitting over the entire dynamic range of the data (100-200 fold).

Figure 35:
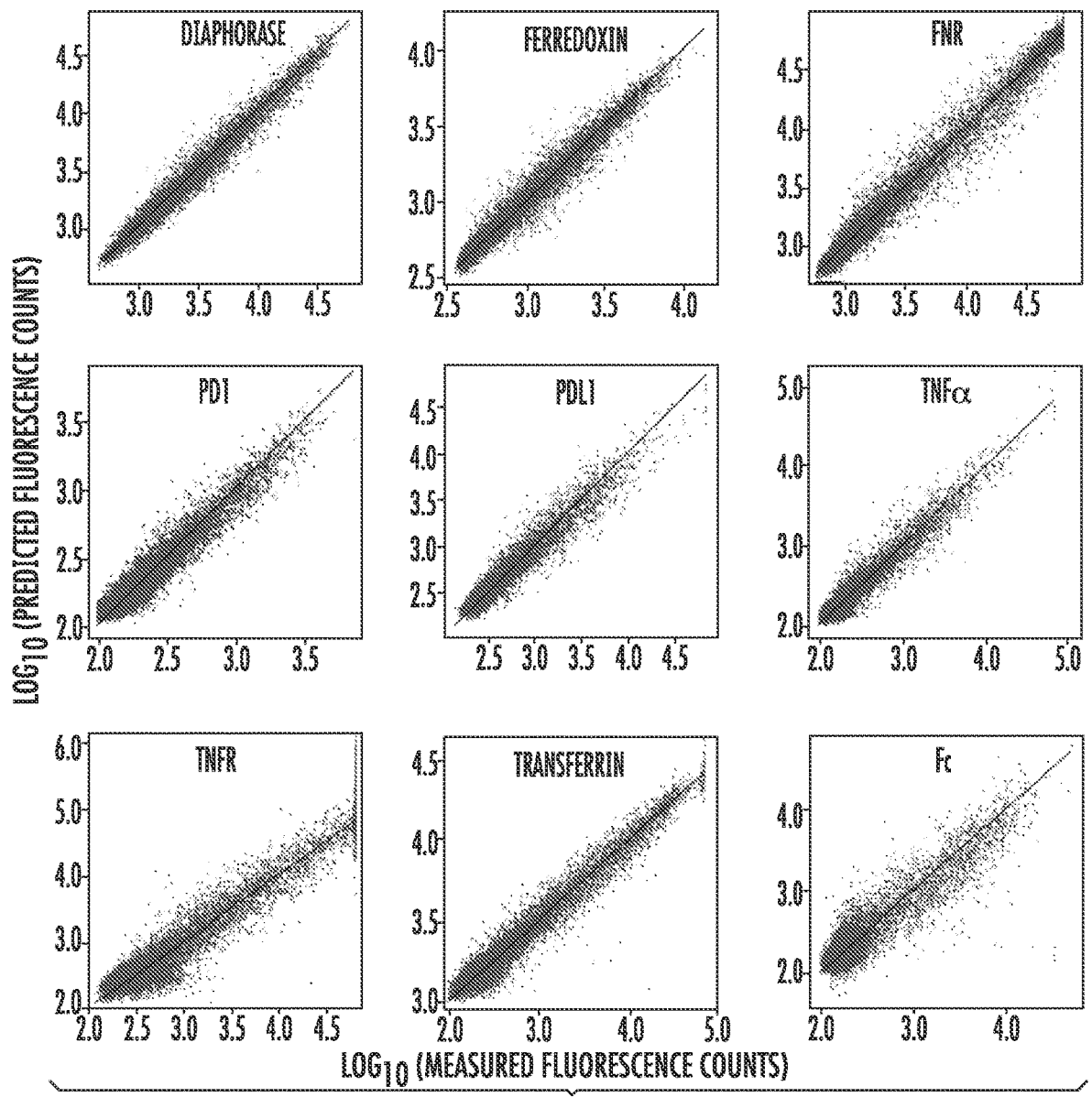
FIG. 35. Representative examples of predicted vs. measured binding values in logarithmic scale for the nine proteins studied in this work. In each case 90% of the unique peptide sequence/binding value pairs on the array were used to train the network and the remainder were used as validation. Only the validation set is shown in the plots above; these are predictions of sequences that were never seen during the training and are effectively random samples from the entire $10^{12}$ sized sequence space. Note that what is plotted is $\log_{10}$ (counts+100) to be consistent with the way the fits were performed.
Figure 37A:
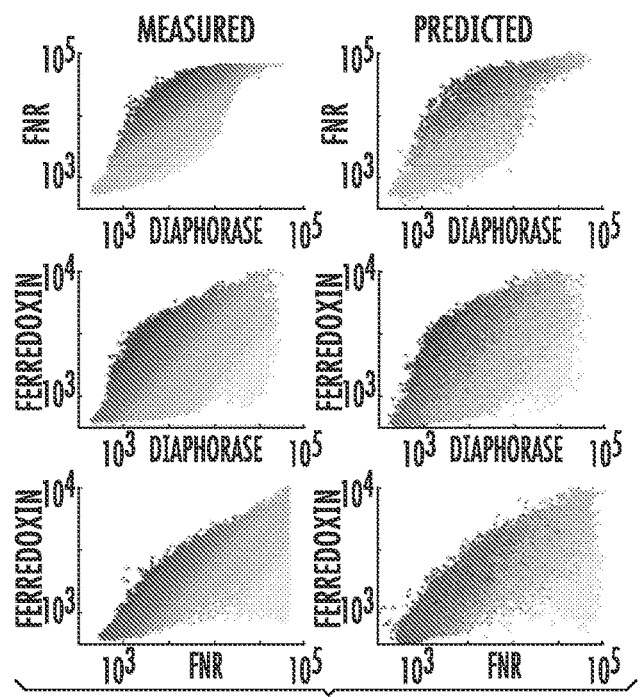
FIG. 37. Specific binding. A) The measured (left side) and predicted (right side) sequence binding values compared between all combinations of two proteins from the set diaphorase, FNR and ferredoxin. B) Similar comparisons between all combinations of PD1, PDL1, TNFαβ and TNFR. See FIG. 28 and associated text for details.
Figure 37B:
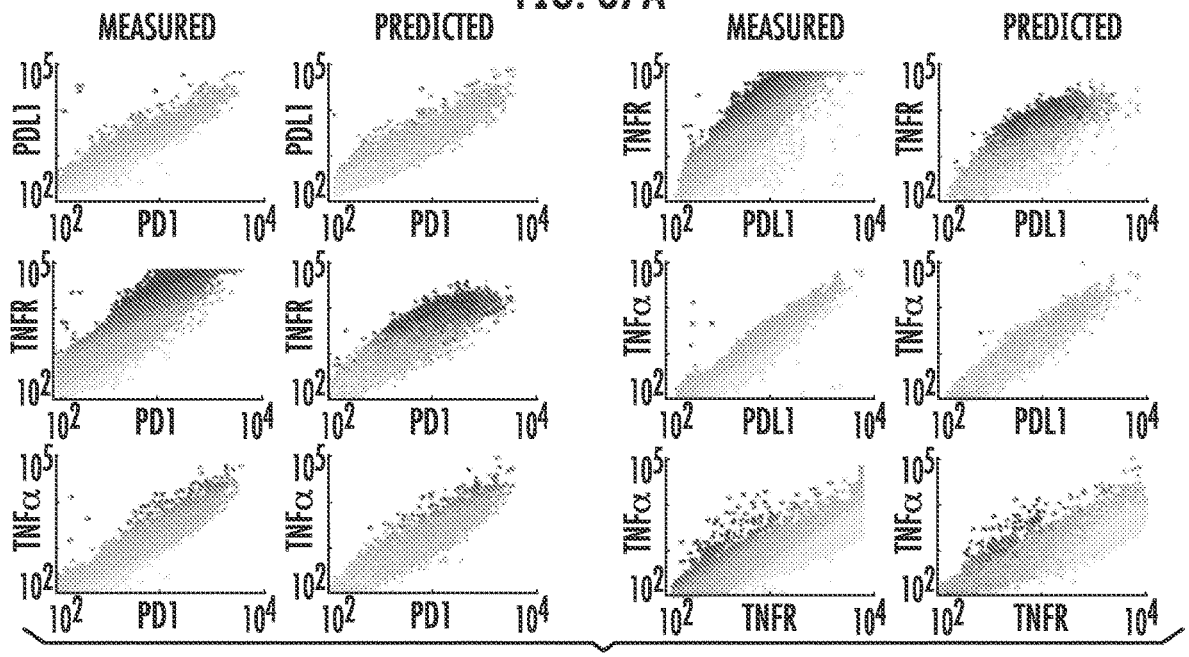

The weights of the neural network were optimized by a mean squared error criterion with an Adam optimizer set to a learning rate of 10'. Training was performed in 50,000 steps for all fits except those in FIG. 31, where 20,000 steps were used. A batch size of 100 sequences at a time was used in all fits. These sequences were not randomly selected, but rather sampled such that all binding values (in log scale) are equally represented in each batch, regardless of the actual distribution of values. This sampling method was found to improve the model's extrapolative performance in regions of very weak and very strong binding where little data exists, at the cost of its ability to interpolate in data-rich regions. No dropout was applied to any of the weights during training. Depending on the situation, the training and validation peptides where randomly chosen between 10 and 100 times and results averaged (The only exceptions are that the scatter plots in FIG. 35 are representative individual runs, and the correlation values in FIG. 37 are averages of three runs).

This machine learning approach is computationally rapid and, as described below, lends itself to chemical interpretation. Note that most of the calculations were performed on stand-alone workstations with 18-20 cores. When done as parallel batches on one of these machines, >50 independent fits per hour can be done.

Results

Peptide Binding Prediction.

FIG. 27A shows the predicted versus measured binding values using the fluorescently labeled enzyme, diaphorase, as the target. The binding values measured for 90% of the sequences on the array (~113,000 peptides) were used to train the model, with the remaining 10% of sequences (test set of ~13,000 peptides) used to cross-validate the model's performance. The Pearson correlation coefficient between predicted and measured values in the test set was 0.985±0.001 (based on 100 runs with randomly selected training and test sets), nearly the same as the correlation between multiple array binding measurements (~0.99). (Note that these correlations are done on log scale data). The fit is thus limited by the signal-to-noise of the experimental measurement. Similar results have been obtained for the nine purified proteins shown in FIG. 27B (data for each protein is given in FIG. 35). The training and test sets are chosen nearly randomly from all possible peptide sequences, implying that sampling only ~$10^5$ sequences is sufficient to accurately describe the target binding over the entire space of $10^{12}$ sequences (The photolithographic method of array synthesis does bias the sequence representation on the array away from purely random to some extent, but it should not affect the results presented here).

Target Specificity.

Figure 28A:
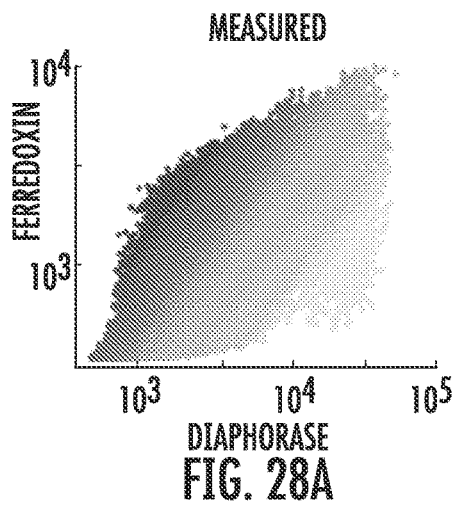
FIG. 28. A neural network was trained on a dataset of 90,000 peptide sequence/binding value pairs for both diaphorase and ferredoxin and the remaining ~36,000 sequence/binding value pairs were predicted (validation set) A) Scatter plot comparison of the measured ferredoxin and diaphorase binding values of the validation set. The color of each point is proportional to the difference between binding values for the two proteins for the sequence represented by that point (dark blue: ferredoxin>diaphorase, yellow: diaphorase>ferredoxin). B) Comparison of the predicted binding values of the validation set for the two proteins. The point associated with a particular sequence in (A) has the same color in (B), allowing one to track whether the points stay in the same positions within the scatter plot. The preservation of the shape and color position between (A) and (B) means that the specificity of binding between the two proteins is captured in the neural network model.
Figure 28B:
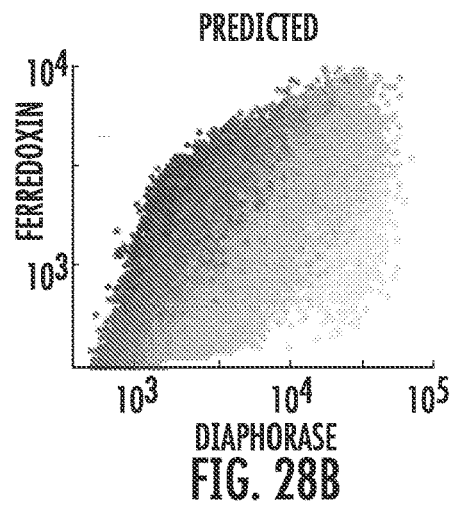

Two sets of proteins listed in FIG. 27B were measured using identical peptide arrays, under the same conditions, at the same time (set 1: diaphorase, ferredoxin, FNR; set2: PD1, PDL1, TNFα, TNFR, Fc). Within one of these sets, one can ask whether there is specific binding (do binding values for specific sequences change significantly between two proteins?). An example is given in FIG. 28. Here binding for the proteins diaphorase and ferredoxin are compared. Each of the datasets was fit using the neural network algorithm described above. For these fits 90,000 sequence/binding pairs were used to train the algorithm and the remaining 36,000 were the validation set. FIG. 28 shows results for only the validation set. FIG. 28A is a scatter plot of the measured values for each of the validation set sequences, comparing ferredoxin to diaphorase. Note that the distribution is very wide (this is a log scale), meaning that the values for a particular sequence can be quite different between the two proteins. The difference between the proteins is color coded. Sequences that bind strongly to ferredoxin relative to diaphorase are more blue. Sequence that bind strongly to diaphorase relative to ferredoxin are more yellow. In FIG. 28B, the predicted binding values for the same sequences are plotted. Importantly, each particular sequence is the same color in the two panels (derived from the measured values), making it possible to see where the sequences that bind strongly to one protein or another on the array appear in the predictions. Note that both the shape and the color distribution are very similar in the two panels. Thus, there is both significant target-specific binding on these arrays, and this specific binding is captured by the model. Analysis of additional protein pairs is given in FIG. 37.

Dependence on Training Set Size.

Figure 36:
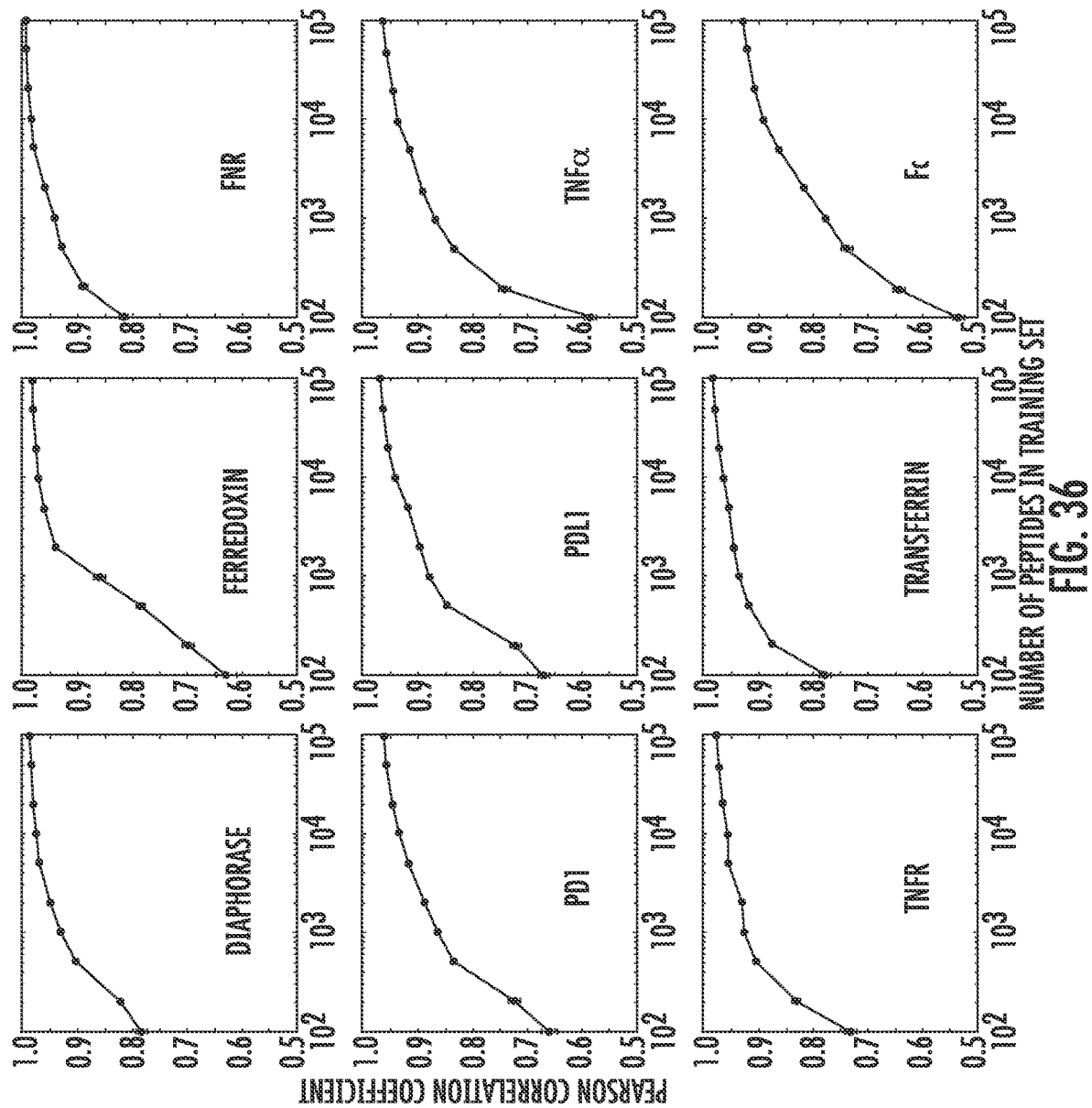
FIG. 36. Correlation coefficient between the predicted and measured binding values plotted as a function of the training set size. As the number of peptides in the training set decreases, the neural network has a stronger tendency to overfit to the training data. Therefore, L1 weight regularization, where the mean of the absolute values of the weights is added as a term to the loss function, was applied during training. The weighting factor for the L1 regularization was optimized for each point in the graph to 0.1, 0.01, 0.001, 0.0001, or 0. Each point is the average of 10 independent training runs with randomly selected training and validation sets. The y-axis is the Pearson correlation coefficient calculated for the validation set comparing the predicted and measured values for those peptide sequences. Error bars are the error of the mean and are only larger than the symbol in the very smallest training sets.

The model performance was determined as a function of training set size between 100 and 100,000 peptides (shown for diaphorase in FIG. 27C). Training with as few as ~1000 peptides gives a correlation coefficient of >0.9 between the predicted and measured values. Similar results were obtained for most of the other proteins tested (FIG. 36). The correlation coefficient appears to be near its maximum by 100,000 peptides in most cases; increasing the sampling by an order of magnitude is unlikely to result in a qualitative model improvement.

Complexity of Amino Acid Representation.

Figure 29A:
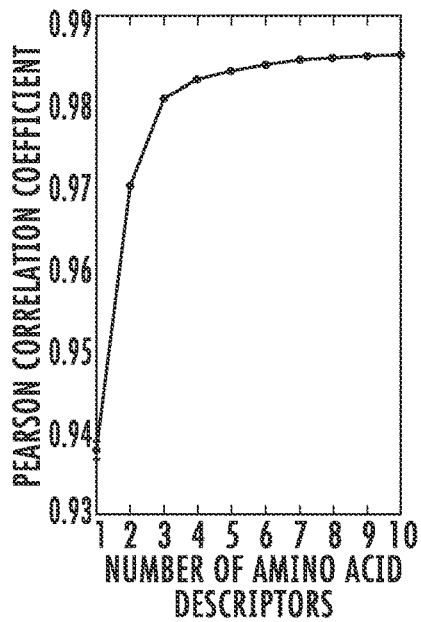
FIG. 29. As in FIG. 1A, 90% of the peptide sequences on an array incubated with diaphorase were used to train a network and 10% were used as the test set. The correlation between the predicted and measured values of the test set is shown vs. the number of amino acid descriptors used to represent each amino acid (average of 100 fits with randomized training sets, error of the mean is shown but generally smaller than the symbol). B) Magnitude-normalized dot products were calculated for each pair of amino acid vector representations creating a similarity matrix for binding to diaphorase. The number of vector descriptors was set to five in this case. The values represent an average of 100 fits with randomized training sets. C) The learned amino acid representations in FIG. 2A were used to fit five different amino acid properties (taken from [1]). The black line represents fits of sets of random numbers as a negative control (average of 100 random sets). For more detail see supplementary materials.
Figure 38:
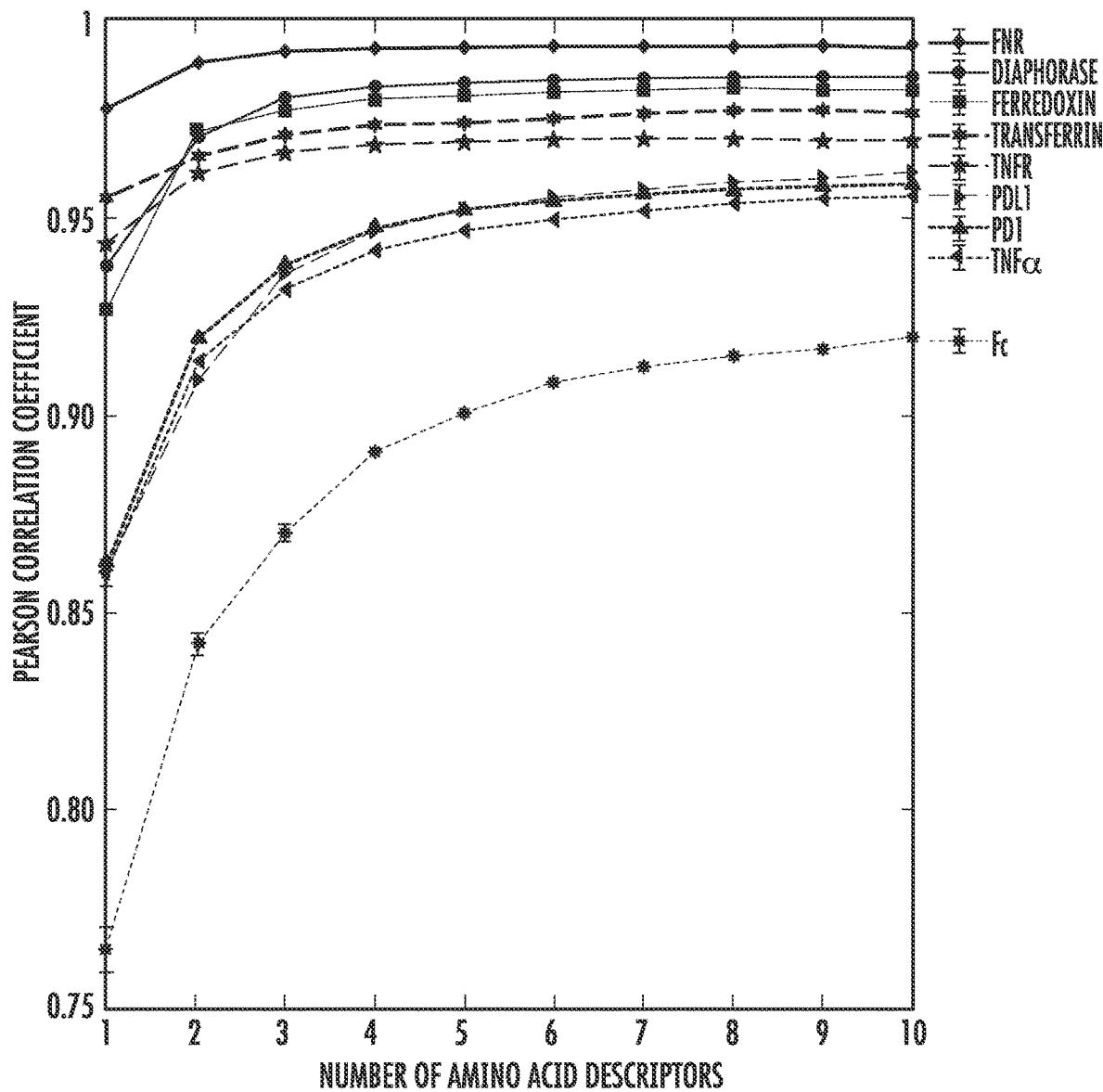
FIG. 38. Correlation coefficient between the predicted and measured binding values vs. the number of amino acid descriptors used in the encoder matrix. Each point is the average of 100 independent training runs and errors shown are errors of the mean (in most cases, the error is smaller than the symbol).

In the analysis above, each amino acid is assigned a vector representation (a set number of descriptors) that is optimized during the fitting process. This encoding acts as an information bottleneck, forcing the neural network to learn a compressed representation of the amino acids; the resulting descriptors presumably contain information about amino acid chemical properties that is necessary for modeling the binding of peptide sequences to that target (e.g. charge, polarity, size). Model performance as a function of the number of descriptors used is shown in FIG. 29A for diaphorase and demonstrates that only a very simple representation of each amino acid is required: using as few as 2 descriptors gives >0.95 correlation, and no appreciable improvement occurs with >7 descriptors. Very similar results are seen for the other proteins (FIG. 38).

Chemistry Learned by the Neural Network

Because the approaches used here involve translating the amino acids into real-valued vector representations, it is possible to therefore reduce amino acid sequences to a series of chemical properties or of values related in some way to combinations of chemical properties. This opens the possibility for not only predicting the function of peptides with different sequences of amino acids, but also the possibility of predicting the function of peptides or heteropolymers that have components (amino acids or other components) that are chemically different from the components used in the training set, but for which the chemical properties are known. This is very powerful, as it expands the set of component-based molecules that can be described vastly.

Figure 29B:
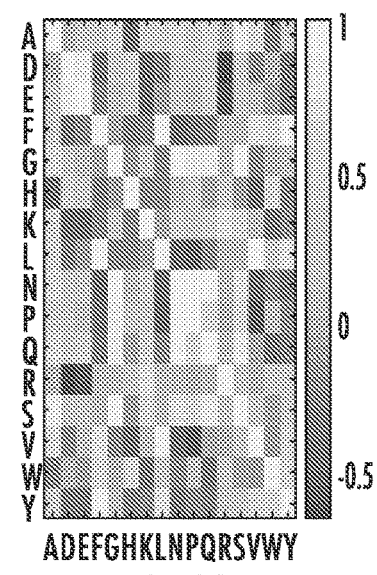
Figure 39:
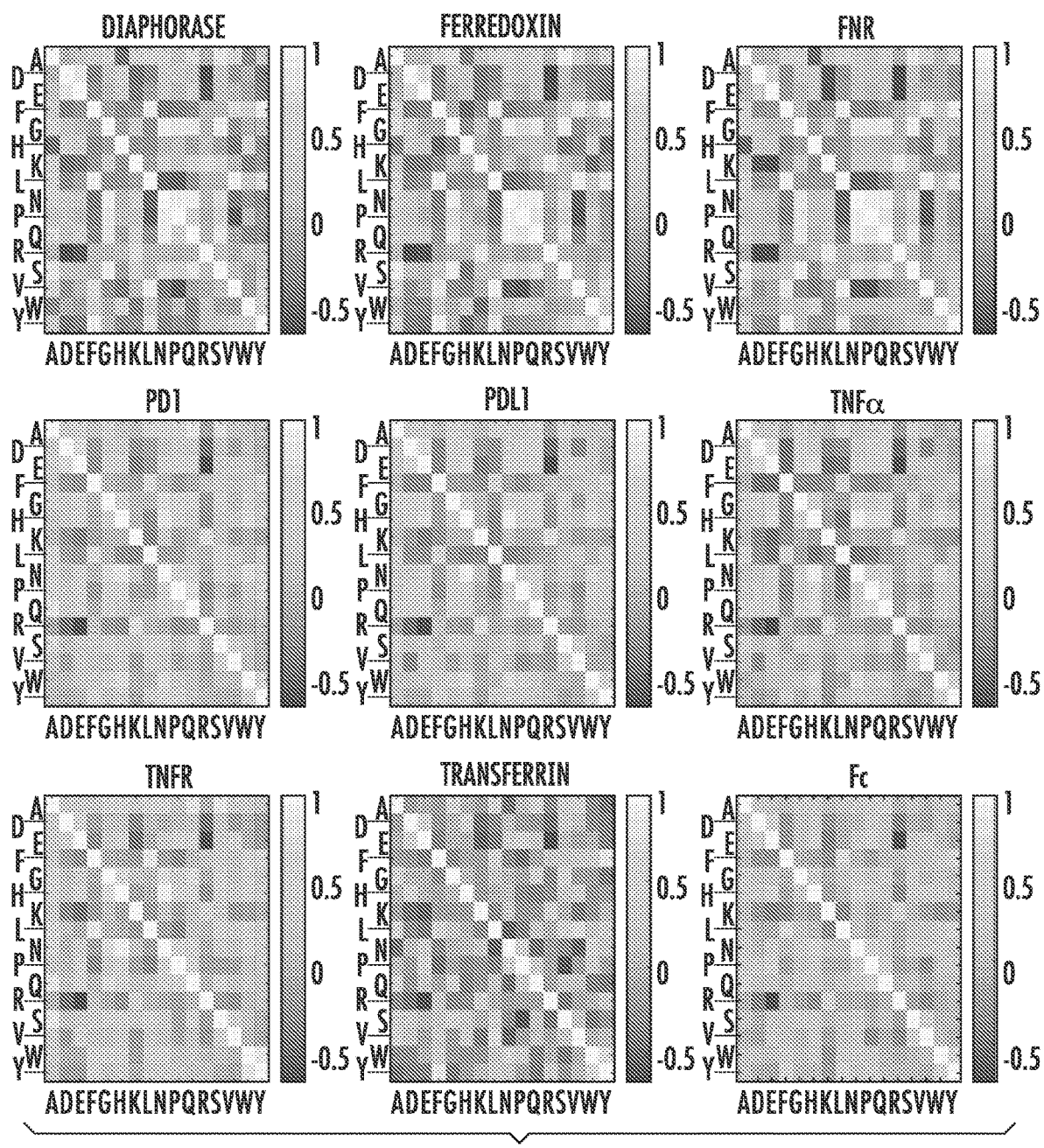
FIG. 39. Heat maps of the similarities between amino acid feature vectors learned by the neural network. Similarity is defined here as the cosine of the angle between the feature vectors (dot product normalized by the vector magnitudes). These similarity matrices were generated as an average of 100 training runs with 5 amino acid descriptors (the angle cosines were averaged).

To better understand how the encoder matrix relates to chemical properties, one can create a target-specific amino acid similarity matrix from the encoder matrix by calculating the orthogonality of the vector representation of each possible amino acid pair (FIG. 29B). Orthogonality is represented as the normalized dot product of the learned vector representations, and given as a heat map. The result generally agrees with chemical intuition, with structurally related amino acids being similar (D&E, N&Q, F&Y, L&V, G&S) and amino acids with a common but opposite characteristic (charge) having a negative relationship (D&E vs. K&R). Most proteins tested give comparable results, but there are significant differences in the target-specific similarity matrices of a few proteins (FIG. 39), with certain expected similarities disappearing (e.g., for transferrin, N and Q vectors are nearly antiparallel). Thus the encoder matrix, if allowed to freely optimize, discovers the chemical similarities between the different amino acids.

Figure 29C:
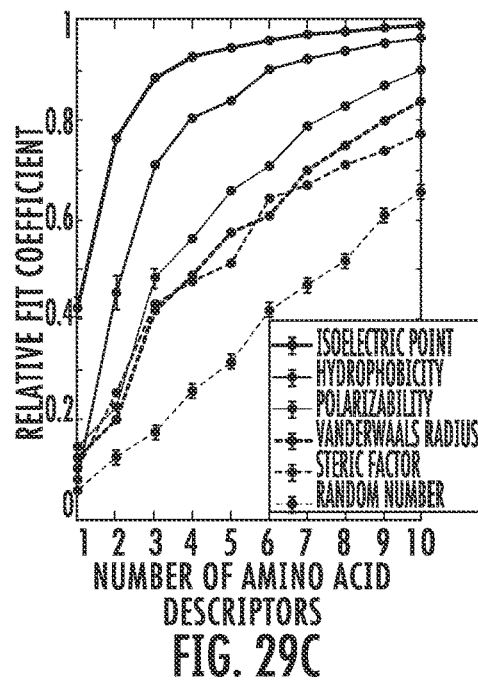
Figure 40:
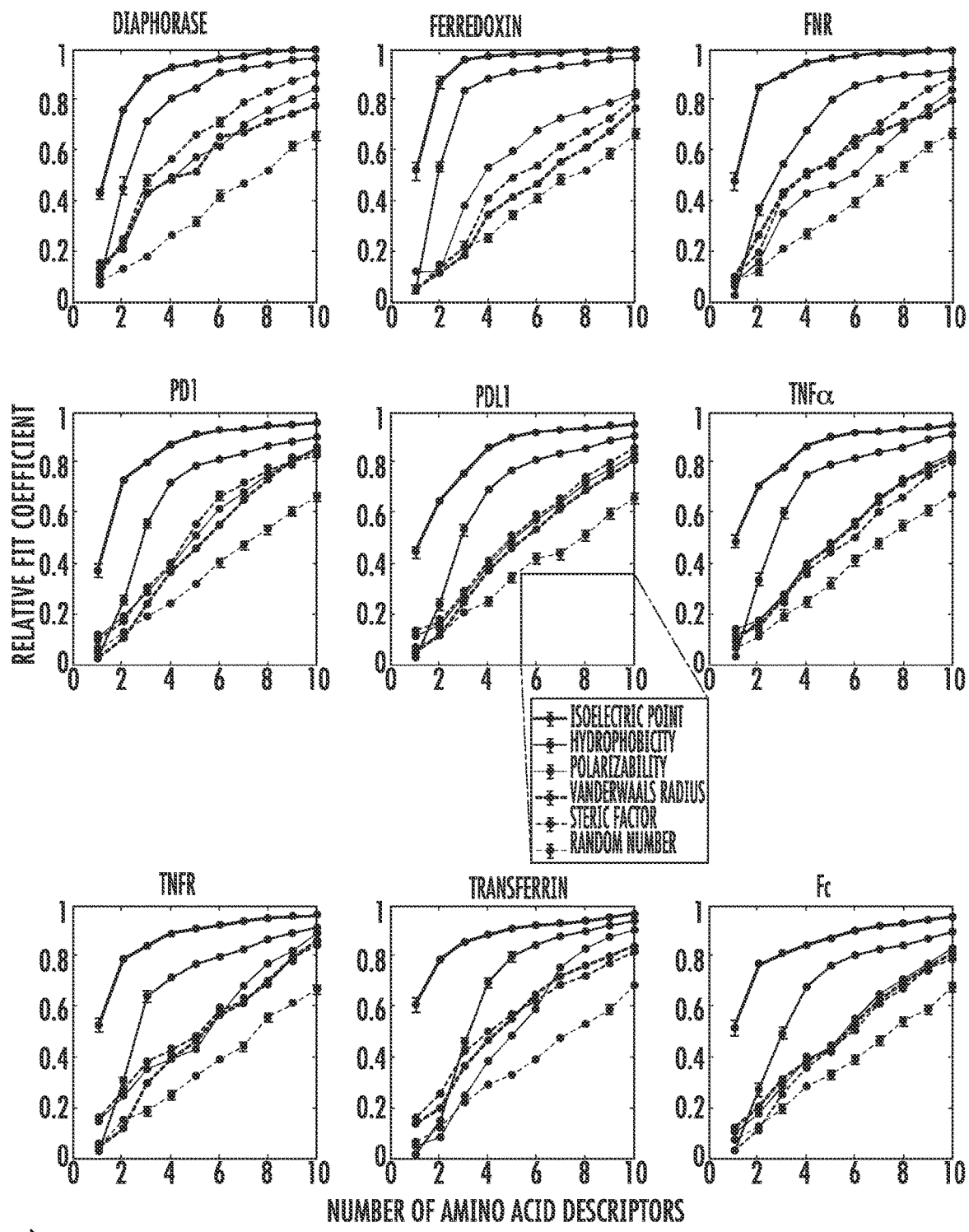
FIG. 40. $R^2$ fit values of the chemistry learned by the neural network fit to the measured chemical properties. This analysis was run for a range of different numbers of amino acid descriptors. For each of 5 chemical properties, a linear fit was performed between the descriptor values and the property: $P_j = c_0 + \Sigma_i c_i d_{i,j}$ where $P_j$ is the property in question for amino acid j, $d_{i,j}$ is the $i^{th}$ descriptor for the $j^{th}$ amino acid and $c_i$ is the associated fitting coefficient for the $i^{th}$ descriptor. The $R^2$ value for the fit is a measure of how much information about a given chemical property is encoded in the amino acid descriptors learned by the neural network. The projection of the encoder matrix onto a set of random numbers is used as a control for over-fitting. Each point is the result of 100 training runs individually fit and then averaged together. Error bars are the error of the mean and are frequently smaller than the symbols.

The chemistry learned by the neural network can be quantified by projecting the learned amino acid feature vectors onto the space of known physical chemical properties. The results are shown in FIG. 29c for diaphorase and in FIG. 40 for the other proteins. Here, five common chemical properties (and a set of random values as a negative control) were fit to a linear combination of the descriptors for all 16 amino acids simultaneously. The plot shows the quality of the fit ($R^2$ coefficient averaged over 100 fits) as a function of the number of descriptors. When only one descriptor is available to represent the amino acids, isoelectric point (charge) is the only chemical property out of those tested contained within the learned representation. Isoelectric point continues to be the most dominant contribution for larger numbers of descriptors, followed by hydrophobicity in order of apparent importance. There are smaller contributions from sterics (graph shape index), the van der Waals term (related to side chain volume), and polarizability. Based on this and the similarity matrix, it is evident that the descriptors that the network chooses for each amino acid contain information about known chemical properties of the amino acids.

The Topology of Peptide-Protein Molecular Recognition Space.

Figure 30C:
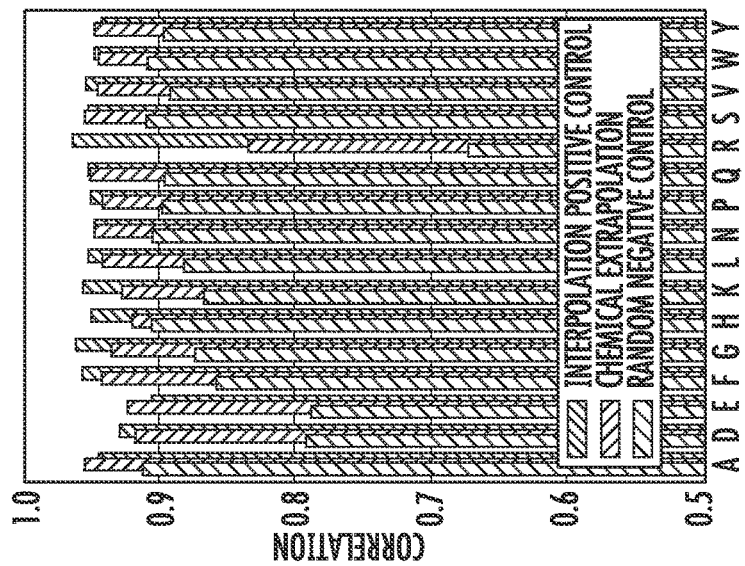
FIG. 30. A) Average autocorrelation of random walks (predicted binding values of 10,000 successive random single mutations) through sequence space starting at 500,000 randomly selected sequences for each protein. B) A model for diaphorase binding data was trained only on sequence/binding value pairs less than 2,000 counts (black) and used to predict binding of sequences with measured values up to 60,000 counts (red). The top 100 predicted sequences are shown in blue and average 40,000 counts. C) Orange bars: Diaphorase sequence/binding data was trained on sequences lacking a particular amino acid, using chemical properties of the amino acids as the descriptors in the encoder matrix; binding of the sequences containing that amino acid are predicted from its chemical properties and the correlation between predicted and measured is shown. Green: Negative control in which random values were used as the fixed properties of the left out amino acid used (100 sets of values averaged; error bars are about 0.01) instead of the literature values. Blue: Positive control in which the neural network was trained using 90% of the sequences that contain the amino acid in question and tested on the remaining 10%. Predicted vs. measured correlation is shown.
Figure 30B:
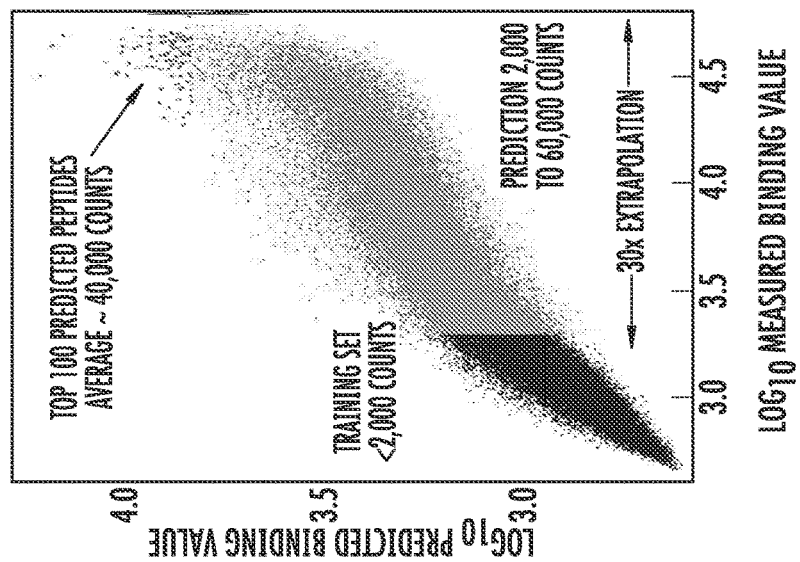
Figure 30A:
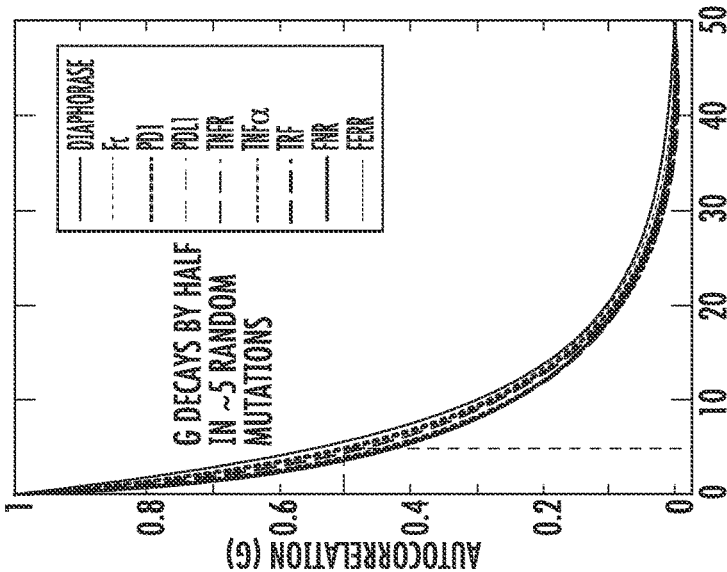
Figure 41:
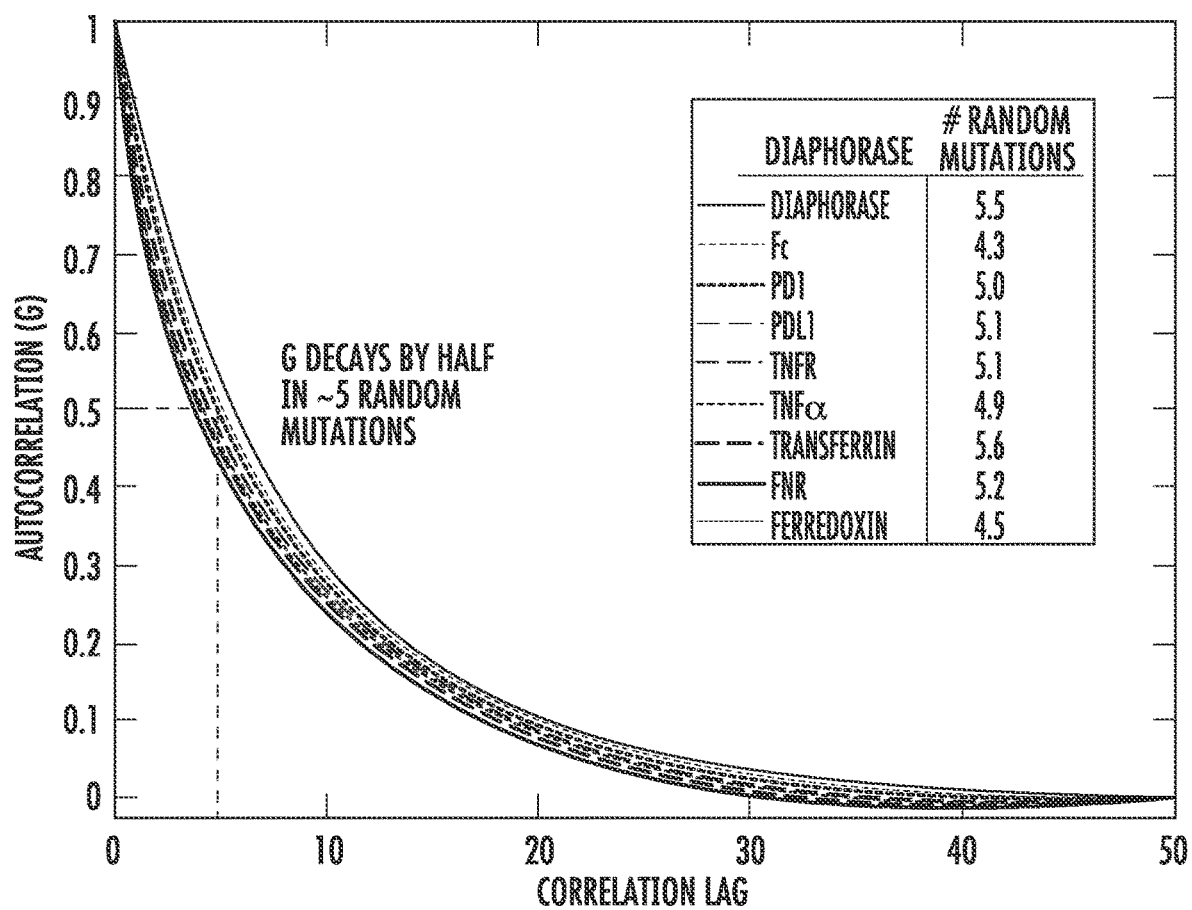
FIG. 41. The autocorrelation curve.

The results described above support the idea that the relationship between peptide sequence and binding is relatively well behaved: a sparse sampling of this space contains sufficient chemical information to accurately predict the binding properties of the entire sequence space. In FIG. 30A, this concept is quantitatively evaluated. In this study, a specific sequence is randomly selected and then a random walk (10,000 random mutations of the sequence) is performed, and at each point in the random walk the predicted binding is calculated. This effectively reduces the topology of the space to one dimension. By then performing autocorrelation of the random walk binding trace, one can learn how many mutations it takes on average to walk off of, or onto, a molecular recognition feature. For each protein, this was repeated 500,000 times using randomly selected starting sequences and averaged. As can be seen in FIG. 30A, the result is remarkably consistent between proteins with 5 random mutations dropping the correlation function by half for a sequence 10 amino acids long. 20-30 mutations take the correlation near zero, more or less irrespective of the protein used (for detailed values see FIG. 41). Thinking about this from an evolutionary perspective, it suggests that a protein segment of about 10 amino acids can vary by a hamming distance of roughly 5 and maintain some of its original molecular recognition properties.

Extrapolating Peptide Predictions

In the examples above, the neural network was used to interpolate the binding values within a library of peptide sequences. It would be even more useful if the algorithm extrapolated accurately outside of the binding values of the original training set. In FIG. 30B, the neural network was trained on a subset weak binding peptide sequences with binding values that are within a factor of 5 of the lowest binding value. For diaphorase, these are sequences with binding signals <2000 counts (FIG. 30B, black points, see FIG. 42 for different ranges of training values). The resulting model is then evaluated on its ability to predict the binding signals of sequences with much stronger binding (FIG. 30B, red/lighter points). For diaphorase, the trained model predicts peptide sequences with binding values up to 30-fold larger than the strongest binding signal of the training set, and the highest 100 predicted values have measured binding signals averaging ~40,000 counts (blue points). Similar results are found for the other 8 proteins (FIG. 43). Overall, the neural network is effective at extrapolating to sequences that show one and two orders of magnitude increase in binding.

In addition to extrapolation in sequence space, it has also been possible to extrapolate to new chemistries. In all the work above, the amino acid descriptors were determined by the neural network. However, if instead the encoder matrix is replaced with measured chemical properties of the amino acids from the literature and not allowed to vary during training, the neural network is forced to learn how to use the chemical properties of the amino acids to predict binding. This is a particularly difficult problem because there are only 16 different amino acids used in the synthesis on the array and it would be very easy to overfit the data (i.e., the range of chemical examples to learn from is limited). Thus, we only used 3 chemical properties per amino acid (isoelectric point, hydrophobicity, and van der Waals radius), and the extrapolation was attempted only for three proteins (Diaphorase, FNR and Ferredoxin). These three proteins were assayed on commercial arrays (HealthTell, Inc.) that were synthesized and assayed under highly optimized conditions, minimizing common amino acid modifications such as oxidation of histidine or tryptophan and providing the highest reproducibility between replicates. Because the literature values of the amino acid chemistry are being used in the fitting, and overfitting is such a concern, high chemical purity and assay reproducibility are essential. In FIG. 30C, the neural network was trained on the subset of peptides lacking one of the amino acids in their sequence, and the model was evaluated on the remaining peptides containing that amino acid and using the chemical properties of that amino acid as input. For example, the third bar set of FIG. 30C is the result for glutamic acid. A neural network was trained on the 57782 sequences in the array that completely lack glutamic acid, using the chemical properties of the other amino acids in the encoder matrix, and then it was tested on its ability to predict binding for the 68268 sequences that contain glutamic acid, using an encoder matrix that includes chemical properties for glutamic acid. Thus, it has the opportunity to learn about chemical properties from the other 15 amino acids and apply that learned information to the peptides containing glutamic acid to predict their binding values (the orange bar is the correlation between predicted and observed).

As a negative control, random values were used for the properties of the amino acid left out of the training (the green bar is an average of 100 random sets). For glutamic acid, the use of the chemical properties of glutamic acid gave rise to a much better prediction that simply using random values (orange vs. green). The positive control involved training and testing on the set of amino acids that contain the particular amino acid (blue bar, 90% used for training). Despite having never been trained to predict the binding properties of the left out amino acid, for glutamic acid, the extrapolation does as well as the positive control. In most cases it does only slightly worse. The cases where it has the most trouble are easy to understand; histidine, lysine, arginine and tryptophan are all amino acids that have unique chemical properties that could not be learned by looking at the other amino acids. Note however that for all amino acids except tryptophan, some chemistry is learned: the extrapolation using the real chemical properties is higher on average than the random value extrapolations (See FIG. 44 for FNR and Ferredoxin).

Iterative Optimization of the Function of a Peptide.

The most striking conclusion of this work is that it is possible to accurately describe the relative target binding of $10^{12}$ peptide sequences based on a very sparse sampling of less than 1 in $10^7$ sequences (FIG. 28). This implies that, on average, molecular recognition features in this space cover many millions of sequences, a conclusion that is consistent with the results from analyzing a random walk in the calculated binding-sequence space showing that the binding properties of a peptide are maintained over a substantial hamming distance (FIG. 30A). Further, it is possible to use these algorithms to perform extrapolation, training on sequences that bind a target only weakly, but predict those that bind 1-2 orders of magnitude more strongly (FIG. 30B). All this suggests that it should be possible to perform computationally guided, iterative optimization of binding by synthesizing a small test set of molecules, modeling them and predicting a higher binding set. The new set is added to the old set and the process repeated.

Figure 31:
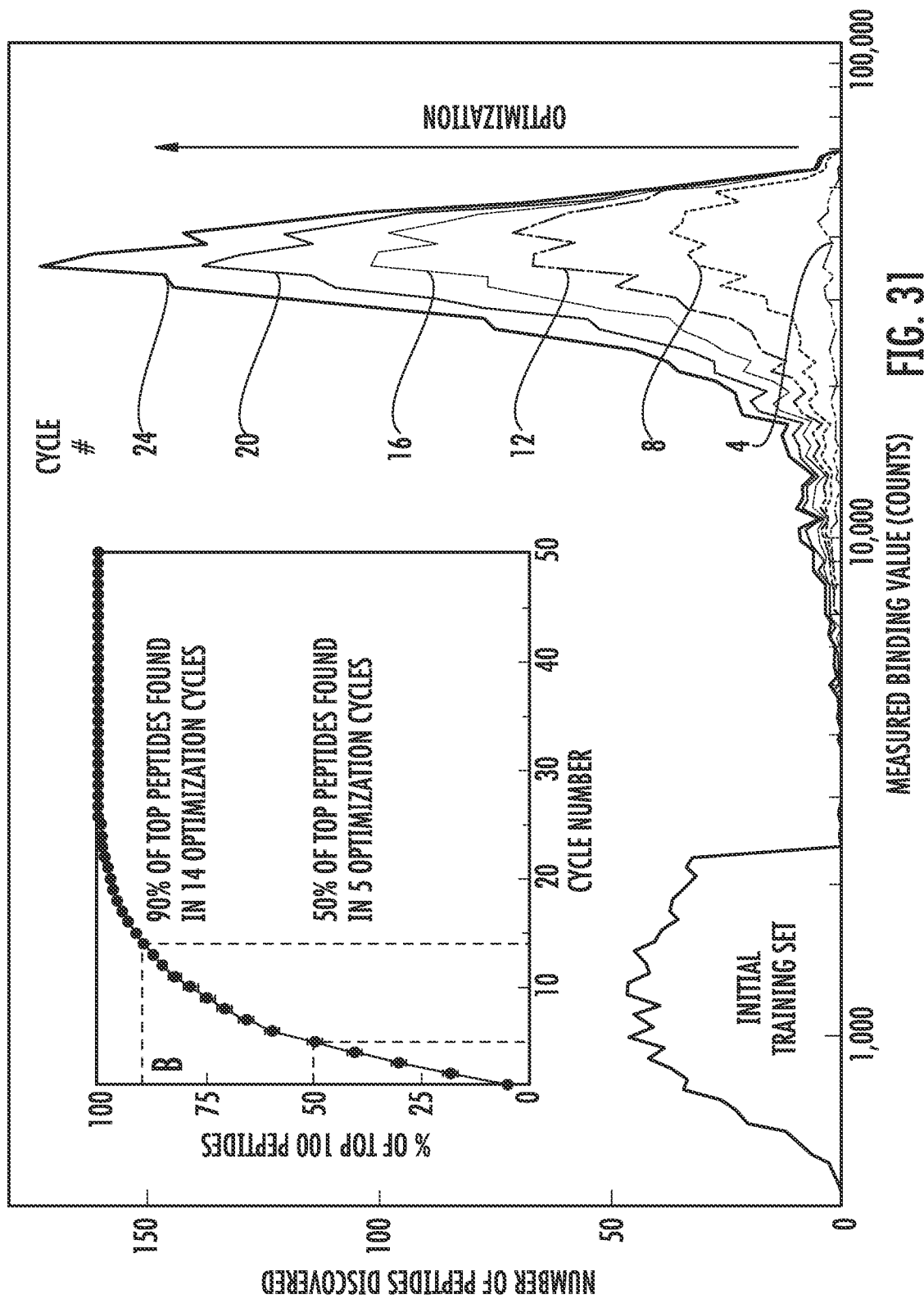
FIG. 31. Distribution of binding strengths as a function of optimization cycle number for diaphorase. 1000 weak binding sequences were used as the initial training set (blue) and each cycle, the 100 strongest binding sequences were predicted and their measured values added to the training (red/purple). Inset: the percent of the 100 strongest binding sequences on the array that were discovered by the iterative process as a function of cycle number for 50 cycles.
Figure 34A:
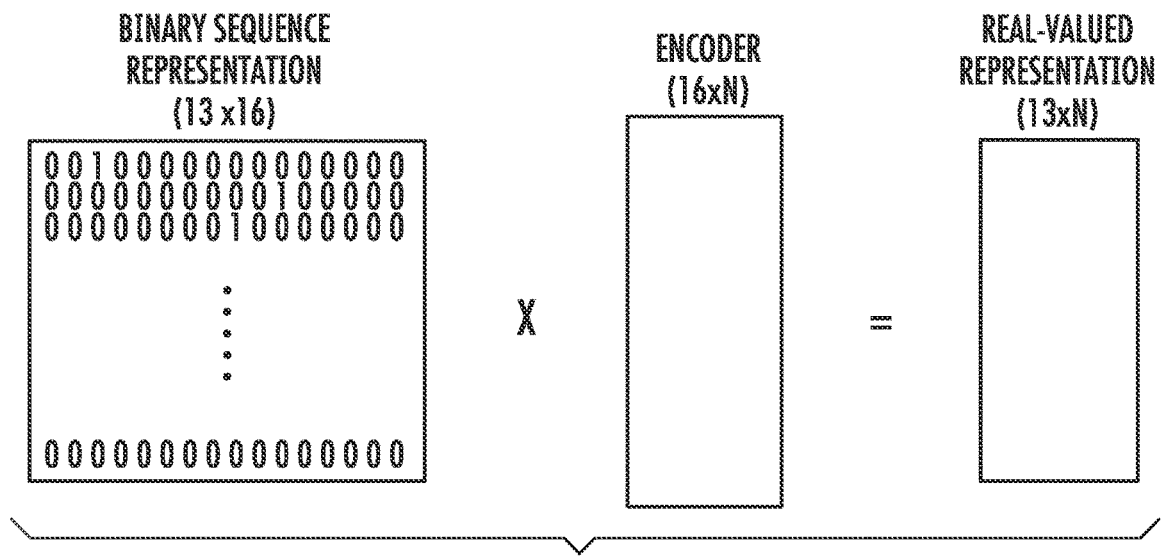
FIG. 34. Neural network architecture for predicting binding value from peptide sequence. (A) The sparse binary representation of the peptide undergoes a linear transformation into the dense real-valued space representation by matrix multiplication with the encoder matrix that utilizes N descriptors in the vector representation of each amino acid. (B) The matrix representation is concatenated row-by-row, resulting in a real-valued space vector representation of the peptide. (C) The real-valued space representation of the peptide is passed through a feedforward neural network with two hidden layers to perform a non-linear prediction of the binding value from the sequence.
Figure 34B:
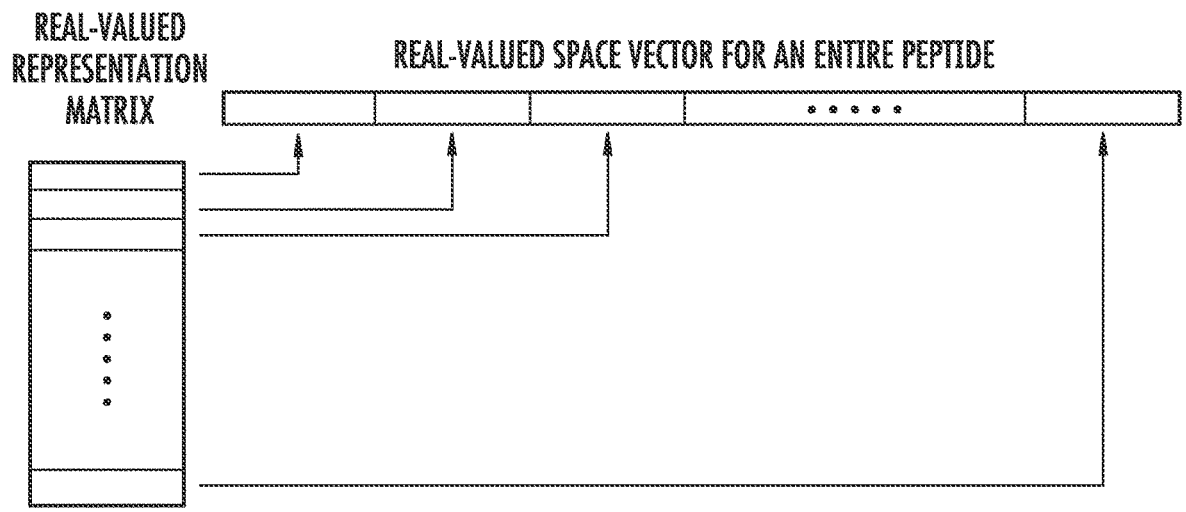
Figure 34C:
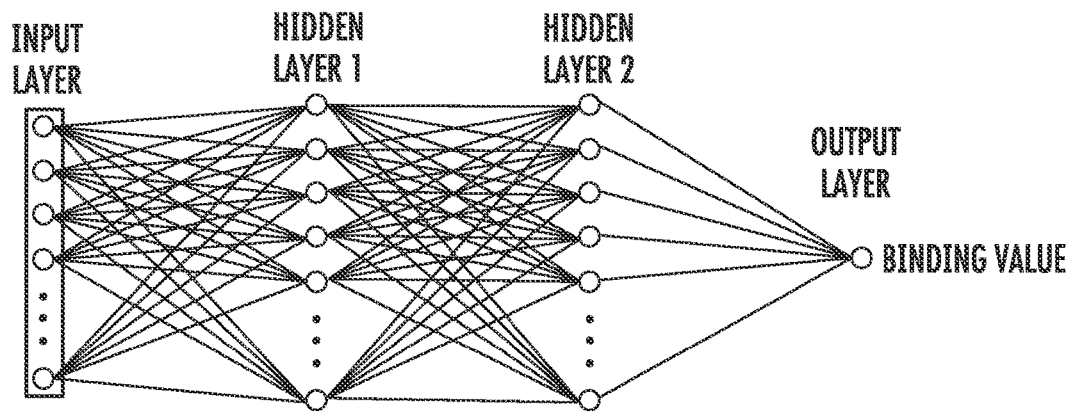

In FIG. 31, this concept was tested by starting with ~1000 weak binding sequences that were randomly selected and used to predict 100 stronger binding sequences from the array. The measured values of these were then added to the training and another 100 strong binding sequences were predicted, etc. As can be seen from the binding distribution vs. cycle number in FIG. 31, the growth in identified molecules was exclusively among the high binders, and after only ten rounds, almost 80 of the top 100 binding molecules in the library had been identified. Similar results were observed for all nine proteins tested, though with varying speeds of optimization (FIG. 45-46). This type of optimization could easily be performed for solution-synthesized molecules (commercial synthesizers are available that synthesize hundreds of molecules a day) and based on more than just molecular recognition levels (e.g., solubility, toxicity in cell assays, off target binding, etc.), providing a computationally accelerated route to molecular optimization. Based on the ability to extrapolate to chemical components not in the original training set (FIG. 30C), it may be possible to optimize not only to new sequences, but sequences that involve different chemical groups using this approach, vastly expanding the space that can be effectively searched to include the hundreds of unnatural amino acids and amino acid modifications. Indeed, there is no reason that an essentially identical approach could not be used for any of a number of molecules that can be built from combinations of parts. While combinatorial chemistry is not a new field, we are now in a much better position to take advantage of it by combining higher throughput synthesis and screening methods with machine learning approaches of the kind discussed here.

Embodiments herein involve computation utilizing devices programmed to process inputs according to the methods described and provide data outputs.

Digital Processing Device

In some embodiments, the systems, platforms, software, networks, and methods described herein include a digital processing device, or use of the same. In further embodiments, the digital processing device includes one or more hardware central processing units (CPUs), i.e., processors that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server, Oracle® Solaris®, Windows Server® and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM).

In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1-30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In some embodiments, the systems, platforms, software, networks, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task, such as those in the algorithms disclosed herein. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS).

In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

While the preferred embodiments of the present disclosure have been illustrated in detail, it should be apparent that modification and adaptations to those embodiments may occur to one skilled in the art without departing from the scope of the present disclosure.

REFERENCES

1. Diehnelt, C. W., *Peptide array based discovery of synthetic antimicrobial peptides*. Front Microbiol, 2013. 4: p. 402.
2. Diehnelt, C. W., et al., Discovery of High-Affinity Protein Binding Ligands-Backwards. Plos One, 2010. 5(5).
3. Domenyuk, V., et al., A Technology for Developing Synbodies with Antibacterial Activity. Plos One, 2013. 8(1).
4. Greving, M. P., et al., High-throughput screening in two dimensions: Binding intensity and off-rate on a peptide microarray. Analytical Biochemistry, 2010. 402(1): p. 93-95.
5. Greving, M. P., et al., Thermodynamic Additivity of Sequence Variations: An Algorithm for Creating High Affinity Peptides Without Large Libraries or Structural Information. Plos One, 2010. 5(11).
6. Gupta, N., et al., *BIOL 183—Synbodies: Progress toward development of synthetic affinity agents*. Abstracts of Papers of the American Chemical Society, 2008. 236.
7. Gupta, N., et al., *Engineering a Synthetic Ligand for Tumor Necrosis Factor-Alpha*. Bioconjugate Chemistry, 2011. 22(8): p. 1473-1478.
8. Gupta, N., et al., *Synthetic ligands (synbodies): Synthetic alternatives to antibodies*. Abstracts of Papers of the American Chemical Society, 2010. 240.
9. Lainson, J. C., et al., Conjugation Approach To Produce a *Staphylococcus aureus* Synbody with Activity in Serum. Bioconjugate Chemistry, 2015. 26(10): p. 2125-2132.
10. Williams, B. A. R., et al., *Creating Protein Affinity Reagents by Combining Peptide Ligands on Synthetic DNA Scaffolds*. Journal of the American Chemical Society, 2009. 131(47): p. 17233-17241.
11. Legutki, J. B. and S. A. Johnston, *Immunosignatures can predict vaccine efficacy*. Proceedings of the National Academy of Sciences of the United States of America, 2013. 110(46): p. 18614-18619.
12. Legutki, J. B., et al., Scalable High-Density Peptide Arrays for Comprehensive Health Monitoring. Nature Communications, 2014. 5: p. 4785.
13. Stafford, P., D. Wrapp, and S. A. Johnston, *General Assessment of Humoral Activity in Healthy Humans*. Molecular & Cellular Proteomics, 2016. 15(5). p. 1610-1621.
14. Singh, S., et al., Humoral Immunity Profiling of Subjects with Myalgic Encephalomyelitis Using a Random Peptide Microarray Differentiates Cases from Controls with High Specificity and Sensitivity. Mol Neurobiol, 2016.

I claim:

1. A method utilizing a computer system programed with one or more algorithms for relating functional data from a library of defined molecules, whose structures consist of combinations of simpler components, to a respective structure of those defined molecules, the method comprising:
   (a) obtaining a data set associated with one or more chemical structures based on a signal derived from interaction of the one or more chemical structures with a chemical or physical phenomenon of interest; and
   (b) applying a model description utilizing the one or more algorithms to the data set to thereby determine a function of a defined molecule in the library according to a value representing the defined molecule's covalent structure, one or more components of that structure, and one or more properties of the components as each relates to the function in question, wherein said one or more algorithms comprises:

$$f_{n(sequence)} = \alpha_0 + \alpha_1 \Sigma_m \Sigma_r \Sigma_k C_{n,m,r} Q_{k,m} A_{k,r} + \alpha_2 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \alpha_3 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \ldots$$

wherein $\alpha_i$ is a multiplier of the term, and $$f_{n(sequence)} = \Sigma_m \Sigma_r \Sigma_k C_{n,m,r} Q_{k,m} A_{k,r}$$

wherein $f_n$ is the function of the nth defined molecule in the library, $C_{n,m,r}$ is a description of the covalent structure of the defined molecule, where n is again the defined molecule in the library, m represents chemical entities that make up the defined molecule, and r represents the positions of a set of structural elements made from those entities, $Q_{k,m}$ represents the assignment of properties to the chemical entities, wherein there are k properties assigned to each of the m chemical entities, and $A_{k,r}$ represents a weighting coefficient assigned to the different functional components of the defined molecule in terms of each of their properties and relates these structures and properties to the measured function.

2. A system programed with one or more algorithms for relating functional data from a library of defined molecules to a respective structure of those defined molecules, wherein the system comprises a specially programmed digital processing device that includes one or more non-transitory computer readable storage media encoded with one or more programs that apply a model description utilizing the one or more algorithms to a data set to thereby determine a function of a defined molecule in the library according to a value representing the defined molecule's covalent structure, one or more components of that structure, and one or more properties of the components as each relates to the function in question, wherein said one or more algorithms comprises:

$$f_{n(sequence)} = \alpha_0 + \alpha_1 \Sigma_m \Sigma_r \Sigma_k C_{n,m,r} Q_{k,m} A_{k,r} + \alpha_2 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \alpha_3 (\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r})(\Sigma_m \Sigma_r \Sigma_k C_{n,m,r} Q_{k,m} A_{k,r}) + \ldots$$

wherein $\alpha_i$ is a multiplier of the term, and $$f_{n(sequence)} = \Sigma_m \Sigma_r \Sigma_k C_{n,m,r} Q_{k,m} A_{k,r}$$

wherein $f_n$ is the function of the nth defined molecule in the library, $C_{n,m,r}$ is a description of the covalent structure of the defined molecule, where n is again the defined molecule in the library, m represents chemical entities that make up the defined molecule, and r represents the positions of a set of structural elements made from those entities, $Q_{k,m}$ represents the assignment of properties to the chemical entities, wherein there are k properties assigned to each of the m chemical entities, and $A_{k,r}$ represents a weighting coefficient assigned to the different functional components of the defined molecule in terms of each of their properties and relates these structures and properties to the measured function.

* * * * *

SEQUENCE LISTING

```
<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Glu Gln Asn Ser Gln Val Asp Gly
1               5

<210> SEQ ID NO 2
<211> LENGTH: 451
<212> TYPE: PRT
<213> ORGANISM: Homo sapiens

<400> SEQUENCE: 2
```

```
Met Arg Glu Cys Ile Ser Ile His Val Gly Gln Ala Gly Val Gln Ile
1               5                   10                  15
Gly Asn Ala Cys Trp Glu Leu Tyr Cys Leu Glu His Gly Ile Gln Pro
                20                  25                  30
Asp Gly Gln Met Pro Ser Asp Lys Thr Ile Gly Gly Asp Asp Ser
            35                  40                  45
Phe Asn Thr Phe Phe Ser Glu Thr Gly Ala Gly Lys His Val Pro Arg
    50                  55                  60
Ala Val Phe Val Asp Leu Glu Pro Thr Val Ile Asp Glu Val Arg Thr
65                  70                  75                  80
Gly Thr Tyr Arg Gln Leu Phe His Pro Glu Gln Leu Ile Thr Gly Lys
                85                  90                  95
Glu Asp Ala Ala Asn Asn Tyr Ala Arg Gly His Tyr Thr Ile Gly Lys
                100                 105                 110
Glu Ile Ile Asp Leu Val Leu Asp Arg Ile Arg Lys Leu Ala Asp Gln
        115                 120                 125
Cys Thr Gly Leu Gln Gly Phe Leu Val Phe His Ser Phe Gly Gly Gly
        130                 135                 140
Thr Gly Ser Gly Phe Thr Ser Leu Leu Met Glu Arg Leu Ser Val Asp
145                 150                 155                 160
Tyr Gly Lys Lys Ser Lys Leu Glu Phe Ser Ile Tyr Pro Ala Pro Gln
                165                 170                 175
Val Ser Thr Ala Val Val Glu Pro Tyr Asn Ser Ile Leu Thr Thr His
            180                 185                 190
Thr Thr Leu Glu His Ser Asp Cys Ala Phe Met Val Asp Asn Glu Ala
        195                 200                 205
Ile Tyr Asp Ile Cys Arg Arg Asn Leu Asp Ile Glu Arg Pro Thr Tyr
        210                 215                 220
Thr Asn Leu Asn Arg Leu Ile Gly Gln Ile Val Ser Ser Ile Thr Ala
225                 230                 235                 240
Ser Leu Arg Phe Asp Gly Ala Leu Asn Val Asp Leu Thr Glu Phe Gln
                245                 250                 255
Thr Asn Leu Val Pro Tyr Pro Arg Ile His Phe Pro Leu Ala Thr Tyr
            260                 265                 270
Ala Pro Val Ile Ser Ala Glu Lys Ala Tyr His Glu Gln Leu Ser Val
        275                 280                 285
Ala Glu Ile Thr Asn Ala Cys Phe Glu Pro Ala Asn Gln Met Val Lys
        290                 295                 300
Cys Asp Pro Arg His Gly Lys Tyr Met Ala Cys Cys Leu Leu Tyr Arg
305                 310                 315                 320
Gly Asp Val Val Pro Lys Asp Val Asn Ala Ala Ile Ala Thr Ile Lys
                325                 330                 335
Thr Lys Arg Thr Ile Gln Phe Val Asp Trp Cys Pro Thr Gly Phe Lys
            340                 345                 350
Val Gly Ile Asn Tyr Gln Pro Pro Thr Val Val Pro Gly Gly Asp Leu
        355                 360                 365
Ala Lys Val Gln Arg Ala Val Cys Met Leu Ser Asn Thr Thr Ala Ile
        370                 375                 380
Ala Glu Ala Trp Ala Arg Leu Asp His Lys Phe Asp Leu Met Tyr Ala
385                 390                 395                 400
Lys Arg Ala Phe Val His Trp Tyr Val Gly Glu Gly Met Glu Glu Gly
                405                 410                 415
```

Glu Phe Ser Glu Ala Arg Glu Asp Met Ala Ala Leu Glu Lys Asp Tyr
            420                 425                 430

Glu Glu Val Gly Val Asp Ser Val Gly Gly Glu Glu Gly
        435                 440                 445

Glu Glu Tyr
    450

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Gln Ala Phe Asp Ser His
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Lys Lys Arg Arg Lys Lys Lys Ser Ser Lys Arg Lys
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Ala Leu Glu Lys Asp Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Arg His Ser Val Val
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Trp Trp Glu Asp Leu Glu Arg Asp Phe
1               5

<210> SEQ ID NO 8
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 8

Pro Trp Trp Asp Asp Trp Glu Arg Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Trp Ser Asp Asp Phe Asp Ser Asp Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Trp Trp Glu Asp Glu Trp Glu Val Pro
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Ser Val Phe Glu Leu Asp Tyr Asp Tyr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Val Tyr Glu Leu Leu Glu Lys Asp Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gln Phe Glu Glu Leu Glu Val Asp Tyr
1               5

<210> SEQ ID NO 14
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 14

Asp Leu Ala Ala Leu Glu Lys Asp Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Val Gly Ser Tyr Asp Ser Phe Asp Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Phe Asp Ser Trp Phe Asp Thr Asn Asn
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Val Pro Ser Tyr Asp Ser Phe Asp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Tyr Asp Ser Phe Asp Thr Phe Ile Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Phe Asp Ser Phe Asp Thr Thr Gly Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Pro Gln His Phe Asp Ser Phe Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Pro Pro Ala Ala Tyr Asp Ser Ser His
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Ser Leu Gln Ala Phe Asp Ser His Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Glu Arg Asp Ser Met Leu Leu Gln Gln
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Glu Ile His Leu Leu Leu Leu Gln Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Ile Asp Ser His Met Leu Leu Gln Gln
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 26

Gly Ala Ser Leu Leu Leu Gln Gln
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Ser Ile Val Thr Leu Leu Leu Gln Gln
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Ala Ala Phe Asp Phe Leu Leu Gln Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

His His Arg Ser Ile Leu Leu Ala Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Phe Arg His Ser Val Val Val Pro Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Leu Leu Met Glu Arg Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct

<400> SEQUENCE: 32
```

His Thr Thr Leu Glu His
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Ala Ala Leu Glu Lys Asp Tyr
1               5

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct

<400> SEQUENCE: 34

Asn Ser Thr Ala Phe His Gln Ala Leu Gln Asp Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Asn Leu Glu Asp Pro Ala Ser Arg Asp Leu Val Val
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Arg Glu Thr Thr Arg Ser Ala Ser Phe Cys Gly Ser
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Glu Pro Ser Gly Ser Gly His Ile Asp His Ser Val
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

```
<210> SEQ ID NO 39
<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Arg Ser Arg Ser Gly Ala Lys Leu Ile Gly Thr Asp
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Cys Val Phe Lys Asp Trp Glu Glu Leu Gly Glu Glu
1               5                   10
```

Also on previous sequence:
```
Asn Thr Ala Glu Ser Arg Leu Val Val Asp Phe Ser
1               5                   10
```

UNITED STATES PATENT AND TRADEMARK OFFICE
CERTIFICATE OF CORRECTION

PATENT NO. : 11,205,139 B2
APPLICATION NO. : 16/637369
DATED : December 21, 2021
INVENTOR(S) : Neal Woodbury Page 1 of 1

It is certified that error appears in the above-identified patent and that said Letters Patent is hereby corrected as shown below:

In the Specification

Column 24, Line 15, "RHS" should be --RHSVV--.

Column 35, Line 34, "Server" should be --Server®--.

Signed and Sealed this
Twenty-sixth Day of April, 2022

Katherine Kelly Vidal
*Director of the United States Patent and Trademark Office*